United States Patent [19]
Houghten et al.

[11] Patent Number: 5,763,193
[45] Date of Patent: Jun. 9, 1998

[54] PERALKYLATED OLIGOPEPTIDE MIXTURES

[75] Inventors: Richard A. Houghten, Solana Beach; John M. Ostresh, Encinitas; Sylvie Blondelle, La Jolla, all of Calif.

[73] Assignee: Torrey Pines Institute for Molecular Studies, San Diego, Calif.

[21] Appl. No.: 577,846

[22] Filed: Dec. 22, 1995

Related U.S. Application Data

[60] Division of Ser. No. 257,782, Jun. 9, 1994, Pat. No. 5,480,971, which is a continuation-in-part of Ser. No. 79,144, Jun. 17, 1993.

[51] Int. Cl.$^6$ ................................................. G01N 33/53
[52] U.S. Cl. .......................... 435/7.1; 435/7.2; 435/7.21; 436/501; 436/518
[58] Field of Search ................................. 435/6, 7.1, 7.2, 435/7.21; 436/501, 518

[56] References Cited

U.S. PATENT DOCUMENTS

| | | | |
|---|---|---|---|
| 4,631,211 | 12/1986 | Houghton | 428/35 |
| 4,708,871 | 11/1987 | Geysen | 424/88 |
| 4,833,092 | 5/1989 | Geysen | 436/501 |
| 5,010,175 | 4/1991 | Rutter et al. | 530/334 |
| 5,182,366 | 1/1993 | Huebner et al. | 530/334 |
| 5,202,418 | 4/1993 | Lebl et al. | 530/334 |
| 5,294,392 | 3/1994 | Geysen | 436/518 |

FOREIGN PATENT DOCUMENTS

| | | |
|---|---|---|
| WO 84/03506 | 9/1984 | WIPO. |
| WO 84/03564 | 9/1984 | WIPO. |
| 9200091 | 1/1992 | WIPO. |
| WO 92/00091 | 1/1992 | WIPO. |
| WO 92/09300 | 6/1992 | WIPO. |

OTHER PUBLICATIONS

Merrifield et al., *J. Amer. Chem. Soc.*, 85:2149–2154 (1963).
Houghten, *Proc. Natl. Acad. Sci.*, 82:5131–5135 (1985).
Houghten et al., *Biotechniques*, 4(6), 522–528 (1986).
Geysen et al., *Proc. Natl. Acad. Sci. U.S.A.*, 81:3998–4002 (1984).
Geysen et al., *Proc. Natl. Acad. Sci. U.S.A.*, 82:178–182 (1985).
Geysen et al., in *Synthetic Peptides as Antigens*, 130–149 (1986).
Geysen et al., *J. Immunol. Meth.*, 102:259–274 (1987).
Schoofs et al., *J. Immunol.*, 140:611–616 (1988).
Furka et al., (1988, 14th International Congress of Biochemistry, vol. 5, Abstract FR:–013).
Furka et al., *Int. J. Peptide Protein Res.*, 37:487–493 (1991).
Devlin et al., *Science*, 249:404–405 (1990).
Scott et al., *Science*, 249:386–390 (1990).
Fodor et al., *Science*, 251:767–773 (1991).
Lam et al., *Letters to Nature*, 354:82–84 (1991).
Houghten et al., *Nature*, 354:84 (1991).
Furka et al., Xth International Symposium on Medicinal Chemistry, Budapest, Abstract 288, p. 68 (1988).
Houghten et al., *Peptides*, Smith and Rivier, eds., Proceedings of the Twelfth American Peptide Symposium, ESCOM, Leiden, pp. 560–561 (1992).
Houghten et al., *Innovation and Perspectives in Solid Synthesis: Peptides, Polypeptides and Oligoonucleodies*, R. Epton, ed., Intercept. Ltd., Andover pp. 237–239 (1992).
Pinilla et al., *BioTechniques*, 13:901–905 (1992).
Houghten, et al., *BioTechniques*, 13:412–421 (1992).
Pinilla et al., *Vaccines 92*, Synthetic Peptide Combinatorial Libraries: The Screeing of Tens of Millions of Peptides for Basic Research and Drug Discovery, pp. 25–28 (1992).
Appel et al., *Immunomethods*, 1:17–23 (1992).
Simon et al., *Proc. Natl. Acad. Sci., USA.* 89:9367–9371 (1972).
Plattner et al., *Drug Discovery Technologies*, Clark et al., Eds., Ellis Harwood Ltd. (1990) pp. 92–126.
Das et al., *Biochem. Biophys. Res. Comm.*, 29(2):211–215 (1967).
Neugebauer, "A Guide to the Properties and Uses of Detergents in Biology and Biochemistry" CALBIOCHEM Corp. (1988).
Ostresh et al., *Proc. Natl. Acad. Sci., U.S.A.*, (PNAS) 91:11138–11142 (1994).
William Broad and Nicholas Wade, *Betrayers of the Faith*, Simon and Schuster, New York (1982) p. 54.
Johnathan R. Cole and Stephen Cole, *The Ortega Hypothesis*, Science, 178:368–375 (1972).
Lowe, *Chemical Society Reviews*, 24(5):309–317 (1995).
Thompson et al., *Chem. Rev.*, 96:555–600 (1996).
Plattne et al "Obstacles to Drug Development from Peptide Leads" in *Drug Discovery Technologies* Clark et al Ed., Ellis Harwood Ltd. (1990) pp. 92–126.
Das et al Biochem and Biophys Res. Comm. 29 #2 pp. 211–215 (1967) "N-methylation of N-aryl Oligopeptides".

*Primary Examiner*—Lora M. Green
*Attorney, Agent, or Firm*—Welsh & Katz, Ltd.

[57] ABSTRACT

Linear $C_1$–$C_7$-alkyl peralkylated oligopeptide sets of molecules are disclosed, as are their methods of synthesis and use in acceptor binding assays. Each molecule or chain of a set contains the same number of two to about ten substituted $C_1$–$C_7$-alkyl peralkylated amino acid residues, and the member chains of a set are present in equimolar amounts. The chains of a set contain one or more predetermined peralkylated amino acid residues at one or more predetermined positions of the peralkylated oligopeptide chain. The set contains equimolar amounts of at least six different peralkylated amino acid residues at one or more of the same predetermined positions of the peralkylated oligopeptide chain. Libraries of such sets, processes for their use and solid support-linked peralkylated sets are also contemplated, as are specific permethylated oligopeptides.

14 Claims, No Drawings

SEQUENCE LISTING ( 1 ) GENERAL INFORMATION:

( i i i ) NUMBER OF SEQUENCES: 38

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated peptide."

( x i ) SEQUENCE DESCRIPTION: SEQ ID NO:1:

Ala  Gly  Gly  Phe  Leu
    1                     5

( 2 ) INFORMATION FOR SEQ ID NO:2:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1..5
   ( D ) OTHER INFORMATION: /note= "This is a peralkylated peptide."

( x i ) SEQUENCE DESCRIPTION: SEQ ID NO:2:

Cys Gly Gly Phe Leu
1               5

( 2 ) INFORMATION FOR SEQ ID NO:3:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1..5
   ( D ) OTHER INFORMATION: /note= "This is a peralkylated peptide."

( x i ) SEQUENCE DESCRIPTION: SEQ ID NO:3:

Asp Gly Gly Phe Leu
1               5

( 2 ) INFORMATION FOR SEQ ID NO:4:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1..5
   ( D ) OTHER INFORMATION: /note= "This is a peralkylated peptide."

( x i ) SEQUENCE DESCRIPTION: SEQ ID NO:4:

Glu Gly Gly Phe Leu
1               5

( 2 ) INFORMATION FOR SEQ ID NO:5:

( i ) SEQUENCE CHARACTERISTICS:
   ( A ) LENGTH: 5 amino acids
   ( B ) TYPE: amino acid
   ( D ) TOPOLOGY: linear ( i i ) MOLECULE TYPE: peptide ( i x ) FEATURE:
   ( A ) NAME/KEY: Peptide
   ( B ) LOCATION: 1..5
   ( D ) OTHER INFORMATION: /note= "This is a peralkylated peptide."

( x i ) SEQUENCE DESCRIPTION: SEQ ID NO:5:

Phe Gly Gly Phe Leu

```
       1               5
```

(2) INFORMATION FOR SEQ ID NO:6:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "This is a peralkylated peptide."

(xi) SEQUENCE DESCRIPTION: SEQ ID NO:6:

```
Gly  Gly  Gly  Phe  Leu
 1                    5
```

(2) INFORMATION FOR SEQ ID NO:7:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "This is a peralkylated peptide."

(xi) SEQUENCE DESCRIPTION: SEQ ID NO:7:

```
His  Gly  Gly  Phe  Leu
 1                    5
```

(2) INFORMATION FOR SEQ ID NO:8:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "This is a peralkylated peptide."

(xi) SEQUENCE DESCRIPTION: SEQ ID NO:8:

```
Ile  Gly  Gly  Phe  Leu
 1                    5
```

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "This is a peralkylated peptide."

( x i ) SEQUENCE DESCRIPTION: SEQ ID NO:9:

Lys Gly Gly Phe Leu
1               5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated
          peptide."

( x i ) SEQUENCE DESCRIPTION: SEQ ID NO:10:

Leu Gly Gly Phe Leu
1               5

( 2 ) INFORMATION FOR SEQ ID NO:11:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= "Xaa represents methionine
          sulfoxide."

( i x ) FEATURE:
        ( A ) NAME/KEY: Peptide
        ( B ) LOCATION: 1..5
        ( D ) OTHER INFORMATION: /note= "This is a peralkylated
          peptide."

( x i ) SEQUENCE DESCRIPTION: SEQ ID NO:11:

Xaa Gly Gly Phe Leu
1               5

( 2 ) INFORMATION FOR SEQ ID NO:12:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated
          peptide."

( x i ) SEQUENCE DESCRIPTION: SEQ ID NO:12:

Asn Gly Gly Phe Leu
1               5

( 2 ) INFORMATION FOR SEQ ID NO:13:

( i ) SEQUENCE CHARACTERISTICS:
        ( A ) LENGTH: 5 amino acids (B) TYPE: amino acid
(D) TOPOLOGY: linear (ii) MOLECULE TYPE: peptide (ix) FEATURE:
 (A) NAME/KEY: Modified-site
 (B) LOCATION: 1..5
 (D) OTHER INFORMATION: /note= "This is a peralkylated peptide."

(xi) SEQUENCE DESCRIPTION: SEQ ID NO:13:

Pro Gly Gly Phe Leu
1               5

(2) INFORMATION FOR SEQ ID NO:14:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (ix) FEATURE:
 (A) NAME/KEY: Peptide
 (B) LOCATION: 1..5
 (D) OTHER INFORMATION: /note= "This is a peralkylated peptide."

(xi) SEQUENCE DESCRIPTION: SEQ ID NO:14:

Gln Gly Gly Phe Leu
1               5

(2) INFORMATION FOR SEQ ID NO:15:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (ix) FEATURE:
 (A) NAME/KEY: Peptide
 (B) LOCATION: 1..5
 (D) OTHER INFORMATION: /note= "This is a peralkylated peptide."

(xi) SEQUENCE DESCRIPTION: SEQ ID NO:15:

Arg Gly Gly Phe Leu
1               5

(2) INFORMATION FOR SEQ ID NO:16:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (ix) FEATURE:
 (A) NAME/KEY: Peptide
 (B) LOCATION: 1..5
 (D) OTHER INFORMATION: /note= "This is a peralkylated peptide."

(xi) SEQUENCE DESCRIPTION: SEQ ID NO:16:

Ser Gly Gly Phe Leu
1               5

( 2 ) INFORMATION FOR SEQ ID NO:17:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated peptide."

( x i ) SEQUENCE DESCRIPTION: SEQ ID NO:17:

Thr   Gly   Gly   Phe   Leu
    1                               5

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated peptide."

( x i ) SEQUENCE DESCRIPTION: SEQ ID NO:18:

Val   Gly   Gly   Phe   Leu
    1                               5

( 2 ) INFORMATION FOR SEQ ID NO:19:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated peptide."

( x i ) SEQUENCE DESCRIPTION: SEQ ID NO:19:

Trp   Gly   Gly   Phe   Leu
    1                               5

( 2 ) INFORMATION FOR SEQ ID NO:20:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a peralkylated peptide."

( x i ) SEQUENCE DESCRIPTION: SEQ ID NO:20:

```
        Tyr  Gly  Gly  Phe  Leu
        1                   5
```

(2) INFORMATION FOR SEQ ID NO:21:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..4
        (D) OTHER INFORMATION: /note= "This is a permethylated peptide."

(xi) SEQUENCE DESCRIPTION: SEQ ID NO:21:

```
        Phe  Phe  Phe  Phe
        1
```

(2) INFORMATION FOR SEQ ID NO:22:

(i) SEQUENCE CHARACTERISTICS:
        (A) LENGTH: 5 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..5
        (D) OTHER INFORMATION: /note= "This is a permethylated peptide."

(xi) SEQUENCE DESCRIPTION: SEQ ID NO:22:

```
        Phe  Phe  Phe  Phe  Phe
        1                   5
```

(2) INFORMATION FOR SEQ ID NO:23:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "This is a permethylated peptide."

(xi) SEQUENCE DESCRIPTION: SEQ ID NO:23:

```
        Phe  Phe  Phe  Phe  Phe  Phe
        1                   5
```

(2) INFORMATION FOR SEQ ID NO:24:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /note= "This is a permethylated peptide."

( x i ) SEQUENCE DESCRIPTION: SEQ ID NO:24:

Phe Phe Phe Phe Phe Phe Phe
1               5

( 2 ) INFORMATION FOR SEQ ID NO:25:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..8
    ( D ) OTHER INFORMATION: /note= "This is a permethylated
          peptide."

( x i ) SEQUENCE DESCRIPTION: SEQ ID NO:25:

Phe Phe Phe Phe Phe Phe Phe Phe
1               5

( 2 ) INFORMATION FOR SEQ ID NO:26:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note= "This is a permethylated
          peptide."

( x i ) SEQUENCE DESCRIPTION: SEQ ID NO:26:

Leu Phe Ile Phe Phe Phe
1               5

( 2 ) INFORMATION FOR SEQ ID NO:27:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note= "This is a permethylated
          peptide."

( x i ) SEQUENCE DESCRIPTION: SEQ ID NO:27:

Phe Phe Ile Phe Phe Phe
1               5

( 2 ) INFORMATION FOR SEQ ID NO:28:

( i ) SEQUENCE CHARACTERISTICS:
    ( A ) LENGTH: 6 amino acids
    ( B ) TYPE: amino acid
    ( D ) TOPOLOGY: linear ( i i ) MOLECULE TYPE: peptide ( i x ) FEATURE:
    ( A ) NAME/KEY: Peptide
    ( B ) LOCATION: 1..6
    ( D ) OTHER INFORMATION: /note= "This is a permethylated peptide."

( x i ) SEQUENCE DESCRIPTION: SEQ ID NO:28:

Leu Phe Phe Phe Phe Phe
1                        5

( 2 ) INFORMATION FOR SEQ ID NO:29:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note= "This is a permethylated peptide."

( x i ) SEQUENCE DESCRIPTION: SEQ ID NO:29:

Phe Phe Phe Phe His Phe
1                        5

( 2 ) INFORMATION FOR SEQ ID NO:30:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note= "This is a permethylated peptide."

( x i ) SEQUENCE DESCRIPTION: SEQ ID NO:30:

Leu Phe Ile Phe Phe His
1                        5

( 2 ) INFORMATION FOR SEQ ID NO:31:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..6
        ( D ) OTHER INFORMATION: /note= "This is a permethylated peptide."

( x i ) SEQUENCE DESCRIPTION: SEQ ID NO:31:

Leu Phe Phe Phe His Phe
1                        5

( 2 ) INFORMATION FOR SEQ ID NO:32:

( i ) SEQUENCE CHARACTERISTICS:
        ( A ) LENGTH: 6 amino acids
        ( B ) TYPE: amino acid (D) TOPOLOGY: linear (ii) MOLECULE TYPE: peptide (ix) FEATURE:
    (A) NAME/KEY: Peptide
    (B) LOCATION: 1..6
    (D) OTHER INFORMATION: /note= "This is a permethylated peptide."

(xi) SEQUENCE DESCRIPTION: SEQ ID NO:32:

Leu Phe Ile Phe His Phe
1               5

(2) INFORMATION FOR SEQ ID NO:33:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "This is a permethylated peptide."

(xi) SEQUENCE DESCRIPTION: SEQ ID NO:33:

Leu Phe Phe Phe Phe His
1               5

(2) INFORMATION FOR SEQ ID NO:34:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "This is a permethylated peptide."

(xi) SEQUENCE DESCRIPTION: SEQ ID NO:34:

Phe Phe Ile Phe Phe His
1               5

(2) INFORMATION FOR SEQ ID NO:35:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /note= "This is a permethylated peptide. Xaa in the first position can be either trimethyl ammonium Leu or trimethyl ammonium Phe; Xaa in the third position can be either His or Phe; Xaa in the fifth position can be either Ile or Phe; and, Xaa in the sixth position can be either methyl carboxyamido His or methyl carboxyamido Phe. At least one of Xaa in the fifth or sixth position is Phe."

(xi) SEQUENCE DESCRIPTION: SEQ ID NO:35:

```
Xaa  Phe  Xaa  Phe  Xaa  Xaa
 1              5
```

( 2 ) INFORMATION FOR SEQ ID NO:36:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..4
        ( D ) OTHER INFORMATION: /note= "This is a permethylated peptide."

( x i ) SEQUENCE DESCRIPTION: SEQ ID NO:36:

```
Gly  Gly  Phe  Leu
 1
```

( 2 ) INFORMATION FOR SEQ ID NO:37:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This is a permethylated peptide."

( x i ) SEQUENCE DESCRIPTION: SEQ ID NO:37:

```
Ala  Gly  Gly  Phe  Leu
 1                    5
```

( 2 ) INFORMATION FOR SEQ ID NO:38:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i x ) FEATURE:
        ( A ) NAME/KEY: Peptide
        ( B ) LOCATION: 1..5
        ( D ) OTHER INFORMATION: /note= "This a permethylated peptide."

( x i ) SEQUENCE DESCRIPTION: SEQ ID NO:38:

```
Arg  Gly  Gly  Phe  Leu
 1                    5
```

PERALKYLATED OLIGOPEPTIDE MIXTURES

CROSS-REFERENCE TO RELATED APPLICATION

This is a division of application Ser. No. 08/257,782, filed Jun. 9, 1994, now U.S. Pat. No. 5,480,971, which is a continuation-in-part of application Ser. No. 08/079,144, filed Jun. 17, 1993, whose disclosures are incorporated by reference.

TECHNICAL FIELD

The present invention relates to the synthesis and use of peptide-like mixtures. More particularly, the invention relates to the synthesis and use of a mixture of peralkylated peptides whose peptide bond amido nitrogen atoms are alkylated as can be reactive hydrogens on side chains and a N-terminal amino group, when present, and a C-terminal carboxyl group.

BACKGROUND AND RELATED ART

Over the last several years, developments in peptide synthesis technology have resulted in automated synthesis of peptides accomplished through the use of solid phase synthesis methods. The solid phase synthesis chemistry that made this technology possible was first described in Merrifield et al. *J. Amer. Chem. Soc.*, 85:2149–2154 (1963). The "Merrifield method" has for the most part remained largely unchanged and is used in nearly all automated peptide synthesizers available today.

In brief, the Merrifield method involves synthesis of a peptide chain on solid support resin particles. These particles typically are comprised of polystyrene cross-linked with divinyl benzene to form porous beads that are insoluble in both water and various organic solvents used in the synthesis protocol. The resin particles contain a fixed amount of amino- or hydroxylmethyl aromatic moiety that serves as the linkage point for the first amino acid in the peptide.

Attachment of the first amino acid entails chemically reacting its carboxyl-terminal (C-terminal) end with derivatized resin to form the carboxyl-terminal end of the oligopeptide. The alpha-amino end of the amino acid is typically blocked with a t-butoxy-carbonyl group (t-BOC) or with a 9-fluorenylmethyloxycarbonyl (Fmoc) group to prevent the amino group that could otherwise react from participating in the coupling reaction. The side chain groups of the amino acids, if reactive, are also blocked (or protected) by various benzyl-derived protecting groups in the form of ethers, thioethers, esters, and carbamates, and t-butyl-derived blockers for Fmoc syntheses.

The next step and subsequent repetitive cycles involve deblocking the amino-terminal (N-terminal) resin-bound amino acid (or terminal residue of the peptide chain) to remove the alpha-amino blocking group, followed by chemical addition (coupling) of the next blocked amino acid. This process is repeated for however many cycles are necessary to synthesize the entire peptide chain of interest. After each of the coupling and deblocking steps, the resin-bound peptide is thoroughly washed to remove any residual reactants before proceeding to the next. The solid support particles facilitate removal of reagents at any given step as the resin and resin-bound peptide can be readily filtered and washed while being held in a column or device with porous openings such as a filter.

Synthesized peptides are released from the resin by acid catalysis (typically with hydrofluoric acid or trifluoroacetic acid), which cleaves the peptide from the resin leaving an amide or carboxyl group on its C-terminal amino acid. Acidolytic cleavage also serves to remove the protecting groups from the side chains of the amino acids in the synthesized peptide. Finished peptides can then be purified by any one of a variety of chromatography methods.

Though most peptides are synthesized with the above described procedure using automated instruments, a recent advance in the solid phase method by R. A. Houghten allows for synthesis of multiple independent peptides simultaneously through manually performed means. The "Simultaneous Multiple Peptide Synthesis" ("SMPS") process is described in U.S. Pat. No. 4,631,211 (1986); Houghten, *Proc. Natl. Acad. Sci.*, 82:5131–5135 (1985); Houghten et al., *Int. J. Peptide Protein Res.*, 27:673–678 (1986); Houghten et al., *Biotechniques*, 4, 6, 522–528 (1986), and Houghten, U.S. Pat. No. 4,631,211, whose disclosures are incorporated by reference.

Illustratively, the SMPS process employs porous containers such as plastic mesh bags to hold the solid support synthesis resin. A Merrifield-type solid-phase procedure is carried out with the resin-containing bags grouped together appropriately at any given step for addition of the same, desired amino acid residue. The bags are then washed, separated and regrouped for addition of subsequent same or different amino acid residues until peptides of the intended length and sequence have been synthesized on the separate resins within each respective bag.

That method allows multiple, but separate, peptides to be synthesized at one time, since the peptide-linked resins are maintained in their separate bags throughout the process. The SMPS method has been used to synthesize as many as 200 separate peptides by a single technician in as little as two weeks, a rate vastly exceeding the output of most automated peptide synthesizers.

A robotic device for automated multiple peptide synthesis has been recently commercialized. The device performs the sequential steps of multiple, separate solid phase peptide synthesis through iterative mechanical-intensive means. This instrument can synthesize up to 96 separate peptides at one time, but is limited at present by the quantity of its peptide yield.

The interest in obtaining biologically active peptides for pharmaceutical, diagnostic and other uses would make desirable a procedure designed to find a mixture of peptides or a single peptide within a mixture with optimal activity for a target application. Screening mixtures of peptides enables the researcher to greatly simplify the search for useful therapeutic or diagnostic peptide compounds. Mixtures containing hundreds of thousands or more peptides are readily screened since many biochemical, biological and small animal assays are sensitive enough to detect activity of compounds that have been diluted down to the nanogram or even picogram per milliliter range, the concentration range at which naturally occurring biological signals such as peptides and proteins operate.

Almost all of the broad diversity of biologically relevant ligand-receptor (or affector-acceptor) interactions occur in the presence of a complex milieu of other substances (i.e., proteins make up approximately 5–10 percent of plasma, e.g. albumin 1–3 percent, antibodies 2–5 percent-salts, lipids/fats, etc.). This is true for virtually all biologically active compounds because most are commonly present, and active, at nanomolar and lower concentrations. These compounds are also, in most instances, produced distant from their affection sites.

That a small peptide (or other molecule) can readily "find" an acceptor system, bind to it, and affect a necessary biological function prior to being cleared from the circulation or degraded suggests that a single specific peptide sequence can be present in a very wide diversity, and concentration, of other individual peptides and still be recognized by its particular acceptor system (antibody, cellular receptor, etc.). If one could devise a means to prepare and screen a synthetic combinatorial library of peptides, then the normal exquisite selectivity of biological affector/ acceptor systems could be used to screen through vast numbers of synthetic oligopeptides.

Of interest in screening very large numbers of peptides is work by Geysen et al., which deals with methods for synthesizing peptides with specific sequences of amino acids and then using those peptides to identify reactions with various receptors. See U.S. Pat. Nos. 4,708,871, 4,833,092 and 5,194,392; P.C.T. Publications Nos. WO 84/03506 and WO 84/03564; Geysen et al., *Proc. Natl. Acad. Sci. U.S.A.*, 81:3998–4002 (1984); Geysen et al., *Proc. Natl. Acad. Sci. U.S.A.*, 82:178–182 (1985); Geysen et al., in *Synthetic Peptides as Antigens*, 130–149 (1986); Geysen et al., *J. Immunol.*

Meth., 102:259–274 (1987); and Schoofs et al., *J. Immunol.*, 140:611–616 (1988).

In U.S. Pat. No. 5,194,392, Geysen describes a method for determining so-called "mimotopes". A mimotope is defined as a catamer (a polymer of precisely defined sequence formed by the condensation of a precise number of small molecules), which in at least one of its conformations has a surface region with the equivalent molecule topology to the epitope of which it is a mimic. An epitope is defined as the surface of an antigenic molecule which is delineated by the area of interaction with an antibody molecule.

The mimotopes are synthesized on a series of solid polymer (e.g. polyethylene with a coating of grafted polyacrylic acid) rods having a diameter of about 4 mm and a length of about 50 mm. A spacer formed by reaction of the ε-amino group of t-BOC-lysine methyl ester and then t-BOC-alanine was added to the grafted polyacrylic acid resins, followed by removal of the t-BOC group to provide an amino group to be used to begin the syntheses.

A mixture of blocked (N-protected) amino acids containing different amounts of each of the blocked (N-protected) twenty amino acids to be used was dissolved in dimethyl formamide and then coupled to the rods. That first coupling was repeated three times using conventional solid phase synthesis techniques. Twenty amino acid residues were individually next added to different rods so that twenty rod-linked 5-mer peptide sequences were prepared. Each sequence had a single, known amino acid residue at the amino-terminus and an alleged equimolar mixture of amino acid residues at each of the four other positions of the chain. Each of those twenty rod-linked peptides was then individually reacted with each of the twenty amino acid residues to form 400 (20×20) rod-linked 6-mer peptides having the two amino-terminal positions defined and the four remaining positions as mixtures. Two more positions of alleged equimolar mixtures of amino acids were then added, and the terminal amine acetylated to form N-acetyl 8-mers linked to the rods whose first two amino acid positions were undefined (mixtures), followed by two defined positions, followed by four undefined positions (mixtures), followed by the spacer and then the supporting rods.

The 400 rod-linked N-acetyl 8-mer peptide mixture preparations were then screened in an ELISA assay using a monoclonal antibody to a desired antigenic protein. The 8-mers having the preferential binding to the antibody were identified. Two sets of further 8-mers that contained the identified best-binding 2-mer sequences within those 8-mers were prepared.

A first set contained mixed amino acids at the three C-terminal positions, followed toward the N-terminus, by a position containing each of the twenty amino acids made by twenty separate couplings, the identified 2-mer sequences, two further mixtures at the next two positions, and an N-terminal acetyl group. The second group contained mixed amino acids at the four C-terminal positions, the identified 2-mer sequences, a position made by separate couplings of each of the twenty amino acids, mixed amino acids as the terminal residues and an N-terminal acetyl group.

Each of those rod-linked N-acetyl 8-mers was again screened in an ELISA with the monoclonal antibody. The preferential binding sequences for each group were identified, and thus 4-mer, preferential-binding sequences were identified.

The above process of separately adding each of the amino acids on either side of identified preferential-binding sequences was repeated until an optimum binding sequence was identified.

The above method, although elegant, suffers from several disadvantages as to peptides. First, owing to the small size of each rod used, relatively small amounts of each peptide is produced. Second, each assay is carried out using the rod-linked peptides, rather than the free peptides in solution. Third, even though specific amounts of each blocked amino acid are used to prepare the mixed amino acid residues at the desired positions, there is no way of ascertaining that an equimolar amount of each residue is truly present at those positions.

Indeed, U.S. Pat. No. 5,194,392 contains a table of specific amounts of each N-protected amino acid to use to provide alleged equimolarity. The prosecution history of that patent provides a revised table with different amounts of N-protected amino acids for use.

Rutter et al. U.S. Pat. No. 5,010,175 discloses the preparation of peptide mixtures that are said to contain equimolar amounts of each reacted amino acid at predetermined positions of the peptide chain. Those mixtures are also said to contain each peptide in retrievable and analyzable amounts and are constructed by reacting mixtures of activated amino acids in concentrations based on the relative coupling constants of those activated amino acids.

The mixture of amino acids used for syntheses of peptides having equimolar amounts of each residue is prepared by adjusting the concentration of each amino acid in the reaction solution based on its relative coupling constant. Those relative coupling constants were determined by completely reacting the twenty naturally occurring resin-linked amino acids with each of the same twenty amino acids. The separate 400 resulting dipeptides were severed from their resins and the amount of each amino acid that coupled was determined.

Upon determining those 400 amounts, the 400 corresponding relative rate constants were determined. The concentrations of the reactants were than adjusted to obtain equimolarity of coupling using an algorithm said to be not straightforward to calculate so that the affects of the previously bonded residue (acceptor) on the incoming amino acid can be taken into account.

In practice, acceptors of similar reactivities are reacted with appropriate mixtures of amino acids to achieve the desired results. The concentrations of reactants amino acids are then adjusted based on the condensation results obtained. Acceptors of differing coupling rates were said to be used in separate reaction mixtures.

U.S. Pat. No. 5,010,175 describes preparation of several pentapeptides said to have a single residue at one or more positions and mixtures of four residues at other positions. The mixed positions were reported to contain their mixed residues at equimolarity plus-or-minus (±) about 20 to about 24 percent.

A study using a mixture of the N-protected naturally occurring amino acids was also reported. The amounts of N-protected amino acids used were based on their relative rate determinations, and adjusted to approximate first-order kinetics by having each amino acid in at least 10-fold excess over its final product. Relative rates were determined by averaging values from the 400 separate reactions and additional data not provided. A table of amounts of each of the twenty N-protected naturally occurring amino acids said to provide equimolarity when used as a mixture is also provided in this patent.

In addition, Furka et al., (1988, 14th International Congress of Biochemistry, Volume 5, Abstract FR:013) and (1988, Xth International Symposium on Medicinal Chemistry, Budapest, Abstract 288, p. 168) described the synthesis of nine tetrapeptides each of which contained a single residue at each of the amino- and carboxy-termini and mixtures of three residues at each position therebetween. These mixture positions were obtained by physically mixing resins reacted with single amino acids. The abstract further asserts that those authors' experiments indicated that a mixture containing up to 180 pentapeptides could be easily synthesized in a single run. No biological assays were reported. More recently, Furka et al., Int. J. Peptide Protein Res., 37:487–493 (1991) reported on the synthesis of mixtures of 27 tetrapeptides and 180 pentapeptides prepared by physically mixing reacted resin-linked peptides. Those peptides were synthesized with one or mixtures of three or four residues at each position along the chain. No biological results using those relatively simple mixtures were reported.

More recently, Huebner et al. U.S. Pat. No. 5,182,366 described substantially the same process. Huebner et al. data provided for a mixture of tetramers having a glycine at position 2 from the amino- (N-) terminus and each of five different amino acid residues at positions 1, 3 and 4 from the N-terminus indicated that each of the residues at positions 1, 3 and 4 were present in substantially equimolar amounts and that glycine was present in its predicted amount. Similar data were also provided for twenty-five groups of pentamers, each of which had two known residues at the amino-termini and mixtures of five residues each at the remaining positions. No data were presented as to biological activity or actually obtaining any selected peptide from the prepared mixtures.

A similar approach was also reported by Lam et al., Letters to Nature, 354:82–84 (1991). Those workers reported the preparation of millions of bead-linked peptides, each bead being said to contain a single peptide. The peptide-linked beads were reacted with a fluorescent- or enzyme-labeled acceptor. The beads bound by the acceptor were noted by the label and were physically removed. The sequence of the bound peptide was analyzed.

Recent reports (Devlin et al., Science, 249:404–405[1990] and Scott et al., Science, 249:386–390[1990]) have described the use of recombinant DNA and bacterial expression to create highly complex mixtures of peptides. More recently, Fodor et al., Science, 251:767–773 (1991), described the solid phase synthesis of thousands of peptides or nucleotides on glass microscope slides treated with aminopropyltriethoxysilane to provide amine functional groups. Predetermined amino acids were then coupled to predefined areas of the slides by the use of photomasks. The photolabile protecting group NVOC (nitroveratryloxycarbonyl) was used as the amino-terminal protecting group.

By using irradiation, a photolabile protecting group and masking, Fodor et al. reported preparation of an array of 1024 different peptides coupled to the slide in ten steps. Immunoreaction with a fluorescent-labeled monoclonal antibody was assayed with epifluorescence microscopy.

This elegant method is also limited by the small amount of peptide or oligonucleotide produced, by use of the synthesized peptide or nucleotide affixed to the slide, and also by the resolution of the photomasks. This method is also less useful where the epitope bound by the antibody is unknown because all of the possible sequences are not prepared.

The primary limitation of the above new approaches for the circumvention of individual screening of millions of individual peptides by the use of a combinatorial library is the inability of the peptides generated in those systems to interact in a "normal" manner with acceptor sites, analogous to natural interaction processes (i.e., free in solution at a concentration relevant to the receptors, antibody binding sites, enzyme binding pockets, or the like being studied without the exclusion of a large percentage of the possible combinatorial library), as well as the difficulties inherent in locating one or more active peptides. Secondarily, the expression vector systems do not readily permit the incorporation of the D-forms of the natural amino acids or the wide variety of unnatural amine acids which would be of interest in the study or development of such interactions.

Houghten et al., Letters to Nature, 354:84–86 (1991) reported use of physical mixtures in a somewhat different approach from those of Furka et al., Huebner et al. and Lam et al., supra, by using solutions of free, rather than support-coupled, peptide libraries or sets that overcomes several of the problems inherent in the above art. Here, 324 exemplary hexamer mixtures that contained more than 34 million peptides were first prepared whose N-terminal two positions were predetermined residues, whereas the C-terminal positions of the sets were equimolar amounts of eighteen of the twenty natural (gene-coded) L-amino acid residues. Binding studies were carried out using those 324 mixtures to determine which few provided optimal binding to a chosen receptor such as a monoclonal antibody or live bacterial cells. That study determined the two N-terminal optimal binding residues.

Another eighteen sets were then prepared keeping the optimal first two optimal binding residues, varying the third position among the eighteen L-amino acids used, and keeping the C-terminal three positions as equimolar mixtures. Binding studies were again carried out and an optimal third position residue was determined. This general procedure was reported until the entire hexamer sequence was determined.

Similar studies are also reported in Pinilla et al. Vaccines 92, Cold Spring Harbor Laboratory Press, Cold Spring Harbor, pages 25-27 (1992); Appel et al., Immunomethods, 1:17–23 (1992); Houghten et al., BioTechniques, 13:412–421 (1992); Houghten et al., in Innovation and Perspectives in Solid Phase Syntheses: Peptides, Polypeptides and Oligonucleotides, R. Epton (ed.), Intercept, Ltd., Andover, pages 237–239 (1992); Houghten et al., in

*Peptides*, J. A. Smith and J. E. Rivier (eds.), Proceedings of the Twelfth American Peptide Symposium, ESCOM, Leiden, pages 560–561 (1992); and WO 92/09300 published Jun. 11, 1992.

A still different approach was reported in Pinilla et al., *BioTechniques*, 13:901–905 (1992). In that report, a total of 108 free hexamer peptide mixture sets were prepared. Those sets contained one of eighteen amino acid residues at each of the six positions of the hexamer chains, with the other five positions being occupied by equimolar amounts of those same eighteen residues. Again, over 34 million different peptides were represented by those 108 sets (6 positions×18 residues/position).

Each of the sets was assayed for binding to a monoclonal antibody as receptor. The residue aposach position that provided best binding results for that position provided a peptide sequence that was identical to the known epitope for that monoclonal. This process also provided sequences for other peptides that were bound almost as well by the monoclonal.

The above work with and implications from use of oligopeptides notwithstanding, oligopeptide life times in in vivo systems where the peptide is introduced by injection or inhalation are typically quite short due to hydrolysis and other degradative mechanisms that depend on the peptide bond. Hydrolysis, both by enzymes and stomach acids, can also limit peroral administration of otherwise active oligopeptides.

The availability of a wide variety of clearly identified, hydrolytically stable peptides or peptide-like molecules in relatively limited mixtures would greatly facilitate the search for optimal molecules for any particular therapeutic end use application.

It would therefore be of considerable interest to have a method for the synthesis of mixtures of peptide-like molecules that are stable to enzymatic hydrolysis and in which individual amino acid residue positions can be specifically defined, such that a comprehensive array of molecules is available to researchers for the identification of one or more of the optimal molecules for reaction with receptors (acceptors) of interest, from which one can derive optimum therapeutic materials for treatment of various organism dysfunctions. The disclosure that follows discusses one such group of peptide-like molecules that are more stable to enzymatic hydrolysis than are peptides themselves.

BRIEF SUMMARY OF THE INVENTION

One aspect of the invention contemplates a set of linear peralkylated oligopeptides comprising a mixture of equimolar amounts of linear $C_1$–$C_7$-alkyl peralkylated oligopeptide chain members containing the same number of about two to about ten peralkylated amino acid residues in each oligopeptide chain. Each of the peralkylated amino acid residues except proline has its peptidyl amido nitrogen atom alkylated with a $C_1$–$C_7$-alkyl group. Amino acid side chains and the N-terminal amine group, if present, can also be alkylated so that each alkylated peptide in the mixture can be viewed as a peralkylated oligopeptide. Removal of alkyl ester groups from alkylated carboxylic acid side chains to form carboxyl groups is also contemplated. The members of the set have one or more predetermined, known peralkylated amino acid residues at the same one or more predetermined positions of the oligopeptide chain, and the library has equimolar amounts of at least six different peralkylated amino acid residues at one or more of the same other positions of the peralkylated oligopeptide chain. The amino-terminus of each oligopeptide is a quaternary $C_1$–$C_7$-alkylammonium group, an amino group, an N—$C_1$–$C_7$-alkylamino group or an N—$C_1$–$C_7$-alkyl-N—$C_1$–$C_{18}$ hydrocarboyl or a pyroglutamoyl group. The carboxy-terminus is a $C_1$–$C_7$-alkyl carboxylic acid ester, mono- or di-N—$C_1$–$C_7$-alkylcarboxamide or a carboxyl group. A $C_1$–$C_7$-alkyl group at the N- or C-terminus is a $C_1$–$C_7$-alkyl group that can be the same or different from the other $C_1$–$C_7$-alkyl groups present in each molecule.

The one or more peralkylated amino acid residues at the same one or more predetermined positions of the peralkylated oligopeptide chain are preferably at a predetermined position that is adjacent to one terminus, and more preferably that one terminus is the amino-terminus. The first two peralkylated amino acid residues at the same one or more predetermined positions are adjacent to the amino-terminus in another preferred embodiment. The equimolar amounts of peralkylated amino acid residues are at one or more positions that are adjacent to one terminus in another preferred embodiment, and more preferably, the one terminus is the carboxy-terminus.

A set of peralkylated oligopeptide chains preferably contains five to about eight peralkylated amino acid residues in each chain. A plurality of sets of sets (a library) of peralkylated oligopeptides are also contemplated. One such library contains sets in which only one position is occupied by a predetermined peralkylated amino acid residue, whereas the other positions of each set are occupied by equimolar mixtures of peralkylated amino acid residues. The number of such sets in a library is equal to the number of positions in the oligopeptide chain (the length of the peralkylated peptide) multiplied by the number of peralkylated amino acid residues at each position of the chain. These libraries are sometimes referred to as positional libraries.

Another aspect of the invention contemplates a process for determining the sequence of a peralkylated oligopeptide that preferentially binds to an acceptor. Such a process comprises the steps of:

(a) providing a library of sets of linear $C_1$–$C_7$-alkyl peralkylated oligopeptides in which each set comprises a mixture of equimolar amounts of peralkylated oligopeptide member chains containing the same number of two to about ten peralkylated amino acid residues in each peralkylated oligopeptide chain. The member chains of each set have one or more of at least six different predetermined peralkylated amino acid residues at one or more predetermined positions of the peralkylated oligopeptide chain, and each set has an equimolar amount of at least six different peralkylated amino acid residues at the same one or more other positions of the peralkylated oligopeptide chain. The amino-terminus of each of the peralkylated oligopeptides in the set is a quaternary alkylammonium, amino, N-alkylamino, $C_1$–$C_{18}$ hydrocarboylalkylamido or pyroglutamoyl group, and the carboxy-terminus is an alkylamido, alkylcarboxylate or carboxyl group. A $C_1$–$C_7$-alkyl group at the N- or C-terminus is a $C_1$–$C_7$-alkyl group that can be the same or different from the other $C_1$–$C_7$-alkyl groups present in each molecule. The sets of the library differ in that the one or more predetermined peralkylated amino acid residues present at the one or more predetermined chain positions within each set are different between the sets.

(b) Each set from that library of sets is separately admixed with the acceptor in an aqueous medium at a set concentration of about 0.1 milligrams per liter to about 100 grams per liter. The binding of each set to the acceptor is separately assayed. A set exhibiting preferential, specific binding relative to the other sets is determined, thereby identifying a peralkylated amino acid residue that provided preferential binding at said one or more predetermined positions.

(c) A second library of sets of linear peralkylated oligopeptides is provided in which each set comprises a mixture of equimolar amounts of $C_1$–$C_7$-alkyl peralkylated oligopeptide member chains containing the same number of two to about ten peralkylated amino acid residues in each chain as the chains of the first-named plurality of sets. The member chains of each second library of sets contain the one or more peralkylated amino acid residues of the first-named set identified as exhibiting preferential, specific binding in the same one or more predetermined chain positions as the first-named sets. The member chains of the second sets have a predetermined one of the at least six different peralkylated amino acid residues at another predetermined position of the peralkylated oligopeptide chain different from the one or more positions of the identified peralkylated amino acid residue(s) of the first-named plurality of sets. Each of the second library of sets (a) has equimolar amounts of at least six different peralkylated amino acid residues of the first-named sets at the same one or more positions of the peralkylated oligopeptide chain not occupied by the one or more identified peralkylated amino acid residues or the predetermined peralkylated amino acid residues, (b) has one fewer peralkylated amino acid residue positions occupied by equimolar amounts of at least six different peralkylated amino acid residues, and (c) has the same first and second termini as the peralkylated oligopeptides of said first-named set.

(d) Each set of the second library of sets is separately admixed with the acceptor in an aqueous medium at a set concentration of about 0.1 milligrams per liter to about 100 grams per liter. The binding of each set to the acceptor is separately assayed. A second set exhibiting preferential, specific binding is determined, thereby identifying a peralkylated amino acid residue that provides preferential binding at the other predetermined position in the peralkylated oligopeptide chain;

(e) Steps (c) and (d) are repeated using zero through seven further libraries of sets of peralkylated oligopeptides instead of the second library of sets. Each further library of sets of peralkylated oligopeptides comprises a mixture of equimolar amounts of member linear peralkylated oligopeptide chains containing the same number of two to about ten peralkylated amino acid residues in each peralkylated oligopeptide chain as the chains of the first-named library of sets. The member chains of each further library of sets contain the peralkylated amino acid residues in the oligopeptide chain positions that exhibited preferential, specific binding in a library of sets used immediately before and a predetermined one of the at least six different peralkylated amino acid residues at another predetermined position of the alkylated chain different from the positions of the identified peralkylated amino acid residues of the library of sets used immediately before. Each of the further library of sets has equimolar amounts of the at least six different peralkylated amino acid residues of the first-named sets at the same one or more positions of the peralkylated oligopeptide chain not occupied by the identified peralkylated amino acid residues or the predetermined peralkylated amino acid residues, and has the same first and second termini as the peralkylated oligopeptide of the first-named library set.

(f) At least six peralkylated oligopeptide chains are provided in which each chain contains the same number of two to about ten peralkylated amino acid residues in each peralkylated oligopeptide chain as the chains of the first-named library of sets. Each peralkylated oligopeptide chain contains the identified peralkylated amino acid residues in the peralkylated oligopeptide chain positions that exhibited preferential, specific binding in step (e), a predetermined one of the at least six different peralkylated amino acid residues at another predetermined position in the peralkylated chain different from the positions of the identified substituent reduced amino acid side chains used in step (e), and has the same N- and C-termini as the sets of the first-named library of sets.

(g) Each of the at least six peralkylated oligopeptides of (f) is separately admixed with the acceptor in an aqueous medium at a substituted peralkylated oligopeptide concentration of about 0.1 milligrams to about 100 grams per liter. The binding of each peralkylated oligopeptide is separately assayed. The peralkylated oligopeptide exhibiting preferential, specific binding is determined, thereby determining the sequence of a linear peralkylated oligopeptide that preferentially binds to the acceptor.

The before-discussed preferences as to the sets hold where the sets are used in an above assay. In addition, it is preferred that the identified and predetermined substituent peralkylated amino acid residues are adjacent to each other. More preferably, the predetermined one or more of at least six peralkylated amino acid residues at one or more predetermined positions of (a) include a terminal residue position of the peralkylated oligopeptide chain.

It is also preferred that the first-named peralkylated oligopeptide chains contain about 5 to about 8 peralkylated residues. It is further preferred that at least ten different peralkylated acid residues are utilized instead of at least six.

In one preferred process, the acceptor is a cellular receptor. More preferably, the cellular receptor is present in a bacterium or yeast cell cultured in a growth medium.

Yet another embodiment is another process for determining the sequence of a peralkylated oligopeptide that preferentially binds to an acceptor. This process comprises the steps of:

(a) providing separate libraries or pluralities of sets of linear peralkylated oligopeptides. Each set of those libraries comprises a mixture of equimolar amounts of $C_1$–$C_7$-alkyl peralkylated oligopeptide chains containing the same number of two to about ten peralkylated amino acid residues in each chain. Each peralkylated oligopeptide chain has a single one of at least six different predetermined peralkylated amino acid residues at a single predetermined position of the peralkylated oligopeptide chain, and each set has equimolar amounts of each of the at least six different peralkylated amino acid residues at the other positions of the peralkylated oligopeptide chain. Each set differs from the other sets in the identity and chain position of the single predetermined peralkylated amino acid residue present at the predetermined position within the set. The amino-terminus of each of the peralkylated oligopeptides in the set is a quaternary alkylammonium group, an amino group, an N-alkylamino group, an N-alkyl-N—$C_1$–$C_{18}$ hydrocarboyl group or a pyroglutamoyl group, and the carboxy-terminus is a mono- or di-alkylcarboxamide, alkylcarboxylate or carboxyl group. A $C_1$–$C_7$-alkyl group at the N- or C-terminus is a $C_1$–$C_7$-alkyl group that can be the same or different from the other $C_1$–$C_7$-alkyl groups present in each molecule.

(b) Each set is separately admixed with the acceptor in an aqueous medium at a set concentration of about 0.1 milligrams per liter to about 100 grams per liter, and the binding of each set to the acceptor is separately assayed. The peralkylated amino acid residue that exhibited preferential, specific binding at each position of the peralkylated oligopeptide chain provides the sequence of a peralkylated oligopeptide that preferentially binds to the acceptor, or one or more peralkylated residues that are important to that binding.

The before-discussed preferences for the sets also hold here. In addition, it is preferred that the single, predetermined positions of the library of sets, taken as a group, are adjacent to each other in the peralkylated oligopeptide chain. Each peralkylated chain also preferably contains about 5 to about 8 peralkylated amino acid residues.

It is also preferred that the single predetermined peralkylated amino acid residue of each peralkylated oligopeptide chain is one of at least ten different peralkylated amino acid residues, and the same at least ten different peralkylated amino acid residues are present in equimolar amounts at the other peralkylated oligopeptide positions of each set.

Also contemplated is a set of linear $C_1$–$C_7$-alkyl peralkylated oligopeptides as described before that is linked to a solid support, such as a solid phase synthesis resin. The peralkylated oligopeptides are individually linked the solid support by a selectively severable bond such as an amide or ester bond.

Specific permethylated oligopeptides are also contemplated. One group of permethylated oligopeptides has the formula $Xaa_1PheXaa_3PheXaa_5Xaa_6$ (SEQ ID NO:35)

wherein $Xaa_1$ at the first position is an α-trimethylammonium Leu or Phe residue;

$Xaa_3$ at the third position is His or Phe;

$Xaa_5$ at the fifth position is Ile or Phe; and $Xaa_6$ at the sixth position is a C-terminal N-methylcarboxamido His or Phe, with the proviso that at least one of $Xaa_5$ or Xaa6 is Phe.

Another contemplated permethylated oligopeptide is a permethylated α-N-terminal trimethylammonium C-terminal N-methylamido oligophenylalanine having 5 through 8 Phe residues.

The present invention has several benefits and advantages.

One salient benefit is that its use can enable one to find a new class of antimicrobial agent that is unlike any previously studied and against which microbes have no defenses.

Another benefit is that the permethylated oligopeptides prepared by peralkylation of a solid support-linked peptide undergoes substantially no racemization during the permethylation step.

An advantage of the invention is that the peralkylated oligopeptides are resistant to cleavage by proteolytic enzymes such as trypsin and chymotrypsin.

Another advantage of the invention is that peralkylated oligopeptides that are quite toxic to certain Gram positive bacteria cause substantially no hemolysis of human blood at antimicrobial concentrations.

Still further benefits and advantages of the invention will be apparent to those skilled in the art from the discussion that follows.

DETAILED DESCRIPTION OF THE INVENTION

Introduction

Peptides are one of a number of fundamental classes of biologically relevant effector molecules. Acceptor systems for peptides include: antibodies, enzymes, membrane-bound and internal cellular receptors. Biologically important peptides include bradykinin, oxytocin, α-endorphins, insulin, and the like. Drug discovery involving peptides invariably requires the synthesis and testing of hundreds to thousands of analogs of the original biologically active sequences. In order to understand a given peptide's structure activity relationships, very large numbers of peptide analogs are needed in all of these areas.

The diversity of the combinatorial possibilities of even the 20 natural amino acids makes usually-used synthesis methods sorely limited in the task of screening for optimal peptide antigens, peptide ligands for biologically relevant acceptor systems, enzyme inhibitors, antimicrobials, and the like [i.e., there are 64,000,000 possible six residue peptides ($20^6$), 1,280,000,000 possible seven residue peptides ($20^7$), and the like]. Although the usually-used methods for single peptide syntheses have greatly facilitated studies with synthetic peptides, and are available commercially either on a custom basis or for use in kit form, they permit only a very small fraction of possible oligopeptides (composed of either natural or unnatural amino acids) to be prepared.

Equimolar amounts of each component making up the library (or member set) to be studied could be expected to ensure the necessary selectivity of the interactions of the desired peralkylated oligopeptide in the mixture to be used (i.e., the "needle in the haystack"-finding the correct peralkylated hexapeptide in the 64,000,000 possible combinations of the 20 natural amino acid side chains would be analogous to finding a single steel needle in 63,999,999 copper needles). As an insight into the extreme selection criterion involved in such a system, it is helpful if one considers that a single six-letter word would have to be readily found in the presence of 63,999,999 other six-letter words (63,999,999 six-letter words would fill approximately 50,000 pages of text of the size found in a usual scientific journal).

The present invention relates to oligomeric peptide-like molecules that have peralkylated amino acid residues. The peptide-like molecules of this invention are $C_1$–$C_7$-alkyl peralkylated oligopeptides. The present invention relates generally to linear peralkylated oligopeptides that contain 2 to about 10 peralkylated amino acid residues.

Mixtures of linear $C_1$–$C_7$-alkyl peralkylated oligopeptides are particularly contemplated herein, and a mixture that contains one or more predetermined peralkylated amino acids at one or more predetermined positions of the peralkylated oligopeptide chain with the remaining one or more positions occupied by described equimolar mixtures of peralkylated residues are referred to as a peralkylated oligopeptide set. Such a mixture or set is preferably prepared by peralkylation of a corresponding mixture of oligopeptides.

A plurality of related peralkylated oligopeptide sets constitute a library of sets. The member sets of a library of sets, also referred to simply as a library, have the same length and termini, and have the same number chain positions occupied by equimolar mixtures of the same at least six different peralkylated amino acid residues. The member sets differ from each other in (a) the position of the one or more predetermined peralkylated amino acid residue, (b) the identity of the one or more predetermined peralkylated amino acid residue, or (c) both the position and identify of the one or more predetermined peralkylated amino acid residue.

One exemplary library of 400 sets of hexamers has the N-terminal first two positions occupied by each of the 20 peralkylated naturally occurring (gene coded) amino acid residues, and the C-terminal four residue positions occupied by equimolar mixtures of at least six peralkylated naturally occurring amino acid residues. Another library is itself a library of six libraries of hexamers, and contains a total of 120 member sets. A first member library contains twenty member sets in which position 1 from the N-terminus is occupied by each of the peralkylated twenty naturally occurring amino acids, with the remaining five positions occupied by mixtures. Another library of twenty member sets has position 2 occupied by each of those peralkylated residues and the remaining positions occupied by mixtures. Similar twenty-member set libraries are contemplated in which each of the remaining five positions is occupied by one of those 20 peralkylated residues and the remaining positions are equimolar mixtures of those peralkylated residues.

A contemplated $C_1$–$C_7$-alkyl peralkylated oligopeptide of a set is alkylated at each position of a precursor oligopeptide that bore an active hydrogen. Consequently, each set is also peralkylated, as is a library of sets.

The side chains of many amino acids are unchanged on peralkylation so that, for example, the methyl side chain of an alanine amino acid residue in an oligopeptide is a methyl side chain of a peralkylated oligopeptide. Hydroxyl group-containing side chains are usually protected from alkylation but can be alkylated if desired. Amino acid residue side chains containing carboxyl, amido, guanidino, mercapto, amino, and aza-substitutions contain active hydrogens, and are not inert to the contemplated, preferred peralkylation process. As such, the side chains of aspartic and glutamic acids, asparagine and glutamine, and the guanidino group-containing side chain of arginine are not contemplated.

Rather, all atoms with an active hydrogen atom are alkylated. Thus, the N-terminal α-amino group, when present as such, is formed into a quaternary $C_1$–$C_7$-alkylammonium group, whereas when an N-terminal $C_1$–$C_{18}$ acyl (hydrocarboyl) group such as acetyl is present, an N-acyl-N-alkylamino, $C_1$–$C_{18}$ hydrocarboylalkylamido group is formed. An N-alkyl-N-pyroglutamoyl group is formed where an N-pyroglutamoyl group was present. Similarly, each of the amido groups, except that of a proline (prolyl) that forms a secondary amido peptidyl bond, is alkylated to the greatest extent possible so that the terminal amido groups of Gln and Asn become dialkylated. Side chain blocking groups used during synthesis are usually removed so that carboxyls of Asp and Glu become alkyl carboxylate esters and Cys forms an alkyl thio ether. The aza nitrogens of His and Trp become N-alkylated and the amino and guanidino groups of Lys and Arg become quaternary, alkylammonium groups. The benzyl protecting groups of Ser and Thr are typically not removed, and Met is preferably used as the sulfoxide, which is also stable to alkylation, and can be maintained in a peralkylated set, or reduced, as desired.

Where a precursor oligopeptide is synthesized with its C-terminal residue bonded to a benzhydrylamine (BHA) or methylbenzhydrylamine (MBHA) resin as solid support, the C-terminal residue becomes a mono-alkylated carboxamide if alkylation is done prior to cleavage from the resin and a di-alkylated amide if alkylation is carried out after resin cleavage. Where the C-terminal residue is linked to the solid synthesis support via an ester bond, a C-terminal alkyl carboxylate ester is formed. Reaction of a peralkylated oligopeptide set containing a C-terminal ester group with a mono- or di-$C_1$–$C_7$-alkyl amine forms the corresponding C-terminal $C_1$–$C_7$-alkyl carboxamide. Reaction of a peralkylated oligopeptide or peralkylated oligopeptide set that contains one or more alkyl carboxylate ester groups with an aqueous base such as sodium hydroxide transforms the ester into a carboxyl group. That carboxyl group can thereafter be re-esterified with the same or a different $C_1$–$C_7$-alkyl group using usual esterification techniques.

It is also noted that treatment of a $C_1$–$C_7$-alkyl peralkylated oligopeptide or set of $C_1$–$C_7$-alkyl peralkylated oligopeptides that contain an N-terminal $C_1$–$C_{18}$ acyl group, and particularly an N-benzoyl group with acid, under acidic conditions causes the amino-terminal residue to be removed, leaving an N-alkylamine as the amino-terminal group of the peralkylated oligopeptide or set that is one residue shorter than its precursor set. Thus, where an N-terminal $C_1$–$C_{18}$ acyl group is desired in the peralkylated oligopeptide, that group is added after cleavage from the solid support.

The contemplated sets of linear peralkylated oligopeptides are preferably prepared from corresponding sets or mixtures of oligopeptides by $C_1$–$C_7$-alkyl peralkylation of the mixture. An individual linear peralkylated oligopeptide is preferably also prepared from a corresponding individual oligopeptide. As a consequence, in the description below, the invention will be described in a preferred embodiment in which the linear peralkylated oligopeptides are prepared from precursor oligopeptides that do or can contain most or all of the twenty naturally occurring amino acid residues. It will be understood, however, that the invention can be used with at least six different amino acid residues, and more than twenty different residues.

For instance, an oligopeptide can include the naturally occurring 20 amino acids, one or both isomers of ornithine, norleucine, hydroxyproline, β-alanine and the other $C_4$–$C_6$ amino acids such as γ-aminobutyric and ε-aminocaproic acids and the D-stereoisomers of the naturally occurring twenty amino acids, so that use of about fifty protected D- and L-amino acids is contemplated for synthesis. Precursor oligopeptide sets and oligopeptide mixture pools (discussed hereinafter) that contain all D-amino acid residues and mixtures of both D- and L-forms are contemplated for use in preparing corresponding linear peralkylated oligopeptides and linear peralkylated oligopeptide sets. Consequently, as used herein, the term "amino acid" will, unless otherwise stated, be intended to include not only the naturally occurring (genetically coded) L-amino acids but also their D-stereoisomers and unnatural amino acids. The phrases "amino acid derivative", "protected amino acid derivative" or the like are used herein for a protected amino acid added as a reactant, whereas the phrase "amino acid residue", "residue" or the like is used herein for a reacted protected amino acid that is a portion of an oligopeptide chain.

Further, the terms "peptide" and "oligopeptide" are considered to be synonymous (as is commonly recognized) and each term can be used interchangeably as the context requires. The word "polypeptide" is used for chains containing more than ten amino acid residues. All oligopeptide and polypeptide formulas or sequences shown herein are written from left to right and in the direction from amino-terminus to carboxy-terminus.

The abbreviations used herein for derivatives and residues of the twenty natural amino acids are reproduced in the following Table of Correspondence:

TABLE OF CORRESPONDENCE

| Abbreviation | | |
|---|---|---|
| 1-Letter | 3-Letter | Amino Acid |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |
| X | Xaa | another residue, or one of several residues |

The word "predetermined" is used in two contexts herein, and has a similar meaning in each context.

A "predetermined" amino acid residue is a single residue whose identity is known or specifically defined, e.g., alanine, glycine, tyrosine, etc., as compared to being a mixture of residues. A linear peralkylated oligopeptide or set thereof similarly contains a before-defined peralkylated amino acid side chain whose identity is known or specifically defined.

A "predetermined position" in an oligopeptide mixture sequence or chain is a position, from and including the amino-terminal residue as position 1, occupied by a predetermined amino acid residue or of a mixture of residues, and which position is known and specifically identified. A linear peralkylated oligopeptide similarly contains a peralkylated amino acid residue at a particular position in the chain and, a set of such peralkylated oligopeptides also contains a mixture of peralkylated amino acid residues at other known or specified position(s) in the chain.

The letter "O" is used herein to indicate a predetermined, but unspecified single amino acid residue or the peralkylated amino acid residue of a peralkylated oligopeptide. Subscripted letters "O", e.g., $O_1$, $O_2$, $O_3$ ... $O_n$ etc. indicate a predetermined amino acid residue or peralkylated amino acid residue that is predetermined (specified) and at the same position (1, 2, 3 ... n) among a set of oligopeptide mixtures, solid support-coupled oligopeptide mixtures, in a peralkylated oligopeptide or set, that is free or solid support-coupled. Thus, a subscripted letter "O" such as $O_1$ is used where a particular amino acid residue or peralkylated amino acid residue is intended such as alanine or leucine, whereas an unsubscripted letter "O" is used to mean that each of the plurality of residues or peralkylated residues is present at a given position, but that that residue or peralkylated residue is not specified, but is a single residue. Subscripted numbers need not start at the amino-terminus for any given mixture.

The letter "X" is used to indicate that a position in an oligopeptide set or peralkylated oligopeptide set formula occupied by that letter is an equimolar mixture of each of at least six amino acid residues coupled or peralkylated residues, and preferably ten or more such residues or peralkylated residues, and more preferably about 15 to about 20.

The letter "B" is used to indicate a solid support used in the syntheses described herein, such as a particulate resin.

A peralkylated oligopeptide "corresponds" to a precursor oligopeptide when the former is the peralkylated form of the latter, and vice versa. In addition, an illustrated peralkylated oligopeptide sequence will be usually prefaced by the word "PerA" to further distinguish a peralkylated oligopeptide from its corresponding oligopeptide. The prefix "PerM" is used for a preferred permethylated oligopeptide.

For example, a trimer oligopeptide pool linked to a solid support whose first position is defined and whose second and third positions are mixtures can be represented as $O_1$XX—B. Similarly, a set of preferred linear peralkylated oligopeptides having six peralkylated residues whose second and third positions contain predetermined peralkylated amino acid residues, whose remaining positions are occupied by mixtures of peralkylated residues, whose N-terminal nitrogen atom is bonded to three alkyl groups such as methyl and whose C-terminus is an N-alkyl group such as N-methyl can be depicted as PerA-N(CH$_3$)$_3$—X$_1$O$_2$O$_3$XXX—NH(CH$_3$).

A contemplated linear peralkylated oligopeptide set contains at least one (one or more) predetermined peralkylated amino acid residues at at least one (one or more) predetermined oligopeptide chain position and mixtures of at least six peralkylated amino acid residues used for synthesis at at least one (one or more) other position of the peralkylated oligopeptide chain. At least six different peralkylated amino acid residues are present at the mixed positions and one of those same six peralkylated residues is preferably the at least one predetermined peralkylated residue for a given set with an exception discussed hereinafter. In preferred practice at least ten different peralkylated amino acid residues are used, and more preferably still, about 15 to about 20 peralkylated amino acid residues are used at the mixture positions and each can constitute the single, predetermined peralkylated residue at the at least one predetermined position.

Thus, the peralkylated residue of that at least one predetermined position can be one of at least six, preferably at least ten or more preferably about 15 to about 20 peralkylated residues. That at least one peralkylated residue is usually referred to herein as "a predetermined peralkylated amino acid residue", whereas in other instances that peralkylated residue is described as "one of at least six peralkylated amino acid residues" or the like.

Synthesis Processes

Overview

The preparation of a set of linear peralkylated oligopeptides having a predetermined $C_1$–$C_7$-alkyl peralkylated residue at at least one position and equimolar amounts of at least six other desired peralkylated residues at at least one other position preferably begins with the preparation of a corresponding oligopeptide set that is thereafter peralklyated. Equimolarity being of importance for the peralkylated residues of the mixture positions, synthesis of the corresponding oligopeptide set is of importance.

Two general approaches to such syntheses are preferred. One is referred to as the physical mixture process and the other is referred to as the chemical mixture process. Both approaches utilize a solid phase support such as a benzyhydrylamine (BHA) or methylbenzhydrylamine (MBHA) resin commonly used in solid phase peptide syntheses, as are discussed hereinbelow.

The physical mixture process utilized is that described in Houghten et al., *Letters to Nature*, 354:84–86 (1991); Pinnila et al., *Vaccines 92*, Cold Spring Harbor Laboratory Press, Cold Spring Harbor, pages 25–27 (1992); Appel et al., *Immunomethods*, 1:17–23 (1992); and WO 92/09300 published Jun. 11, 1992. These synthetic processes are also similar to the processes disclosed in Furka et al., *Int. J. Peptide Protein Res.*, 37:487–493 (1991), Huebner et al. U.S. Pat. No. 5,182,366, incorporated by reference, and Lam et al., *Letters to Nature*, 355:82–84 (1991).

The latter two processes and that used for preparing precursor oligopeptide sets herein differ in concept. In both Lam et al. and Huebner et al., the desired peptide is selected by its binding or reaction, recovered and then its sequence is determined. Furka et al. teach no reactions with their mixtures. The present precursor oligopeptide sets are prepared with one or more known, predetermined residues at one or more known, predetermined positions along the chain so that all one need do is determine which oligopeptide of known sequence bound to the acceptor used. That same concept is used for the ultimately produced peralkylated oligopeptides.

A chemical mixture synthesis of a precursor oligopeptide set can be one of those described in Rutter et al. U.S. Pat. No. 5,010,175 or Geysen U.S. Pat. No. 5,194,392, whose disclosures are incorporated by reference, or as described in the previously noted published papers of which Geysen is an author.

Both Rutter et al. and Geysen report using N-t-BOC protecting groups for their chemical mixture syntheses. Each of those patents provides an exemplary mixture of N-t-BOC-blocked amino acid derivatives for use in synthesis of equimolar amounts of amino acid residues.

It is noted that the present invention is not limited to use of N-t-BOC blocking groups for synthesis of precursor oligopeptide sets. This is the case whether the physical or chemical mixture approaches are utilized. Thus, any blocking group can be utilized. Table 1, below, provides mole ratios of blocked amino acids that can be used for a chemical mixture synthesis using Fmoc blocking group chemistry.

TABLE 1*

| Amino Acid | Mole Ratio |
| --- | --- |
| Ala | 0.22 |
| ASP(tBU ester) | 0.47 |
| G1U(tBU ester) | 0.62 |
| Phe | 0.35 |
| Gly | 0.20 |
| His (Tr) | 0.72 |
| Ile | 2.51 |
| Lys (tBoc) | 0.59 |
| Leu | 0.48 |
| Met | 0.34 |
| Asn | 1.65 |
| Pro | 0.20 |
| Gln | 2.03 |
| Arg (Mtr) | 1.98 |
| Ser(tBu ether) | 0.80 |
| Thr(tBu ether) | 2.18 |
| Val | 1.85 |
| Tyr(tBu ether) | 0.81 |
| Trp | 0.99 |

*Parenthesized designations in the left column are protecting groups. tBu = t-butyl; Tr = trityl; tBoc = t-butyloxycarbonyl; Mtr = 4-methoxy-2,3,6-trimethylbenzenesulfonyl.

Substantial equimolarity in the mixture positions is typically within the limits of weighing accuracy using the physical mixture synthetic process because single amino acids are reacted in large excess and reactions are driven to completion. The chemical mixture process does not provide exact equimolarity as does the physical mixture process described before. For example, U.S. Pat. No. 5,010,175 reported variation from equimolarity in the range of 0.20–0.32 moles and an average of 0.25±0.04, with each amino acid being no more than 0.8 to 1.28 times the desired result. Deviations from equimolarity from that obtained with the physical mixture method of up to about 35 percent have been observed with no adverse effect. Regardless of the deviations from exact equimolarity observed from use of the chemical mixture method, the various oligopeptides required to obtain enhanced binding by a corresponding peralkylated oligopeptide are present in large enough quantities to be useful in the assay methods discussed hereinafter.

It is thus seen that both physical and chemical mixture synthetic processes for preparing a desired precursor oligopeptide set are well known in the art. In addition, Examples 1, 2 and 3 herein discuss and illustrate exemplary syntheses using both types of syntheses.

It is noted that cysteine and tryptophan are frequently omitted from precursor oligopeptide sets and corresponding linear peralkylated oligopeptide sets because of side reactions that can occur from their use. It has been found, however, that use of an N-formyl blocking group on tryptophan can alleviate much of the difficulty in synthesis when that residue is incorporated into an oligopeptide chain.

It is further noted that one can use a wide range of solid supports for a contemplated synthesis of an oligopeptide set. Usually used cross-linked styrene beads having benzhydrylamine groups are a preferred solid support. However, many other solid supports as are disclosed in U.S. Pat. No. 4,631,211 can also be utilized, as can a cellulosic support such as cotton as is described in Lebl et al. U.S. Pat. No. 5,202,418, both of whose disclosures are incorporated by reference.

C. Termini and Coupling

In preferred practice, each oligopeptide is coupled to the solid support during synthesis by a selectively severable covalent bond, such as an ester or an amide bond. An ultimately produced oligopeptide mixture set can be cleaved (separated or severed) from the solid support, recovered and thereafter peralkylated to form a free linear peralkylated oligopeptide set, or the alkylation can be carried out while the oligopeptide is coupled to the solid support (oligopeptide mixture pool) to form a solid support-coupled linear peralkylated oligopeptide mixture set.

As noted earlier, each peralkylated oligopeptide contains a chain of two to about ten peralkylated residues, and more preferably about five to about eight peralkylated residues so that a precursor oligopeptide set member contains a chain having two to about ten reacted amino acid residue repeating units. More preferably, each precursor oligopeptide contains a chain of about five to about eight reacted amino acid residues.

A $C_1$–$C_{18}$ straight or branched chain acyl (hydrocarboyl) or pyroglutamoyl group is often bonded to the N-terminus a-amine of an oligopeptide so that after deblocking, alkylation and cleavage from the solid support, each member chain of a peralkylated oligopeptide set contains a $C_1$–$C_{18}$ straight or branched chain hydrocarboyl or pyroglutamoyl group. An acetyl group, a $C_2$ acyl group, is preferred and is often referred to herein as "Ac". Other exemplary $C_1$–$C_{18}$ acyl groups include formyl, propionyl, butyryl, 2-methylpropionyl, hexanoyl, benzoyl, octanoyl, lauroyl, palmitoyl, oleoyl and stearoyl. Hydrogen can also be present at the amino-terminus α-amine of the precursor chains so that a quaternary $C_1$–$C_7$-alkyl ammonium group results at the N-terminus after peralkylation and cleavage from the solid support.

When the N-terminal α-amine is present as a tri-$C_1$–$C_7$-alkylammonium group, an anionic counterion is of course present. The counterion chosen is typically univalent to avoid cross-linking and precipitation of the peralkylated oligopeptide. Where a halide alkylating agent is used such as methyl iodide, benzyl bromide or allyl bromide, that halide is the initial counterion for the formed tri-$C_1$–$C_7$-alkyl ammonium group. Cleavage of the peralkylated peptide from the solid support with HF can replace the initial counterion with a fluoride ion. Any pharmaceutically acceptable counterion can be used such as a halide; i.e., fluoride, chloride, bromide or iodide, nitrate or a $C_1$–$C_6$ carboxylate such as formate, acetate, trifluoroacetate, propional, isobutyrate, hexanoate or the like. A single, desired counterion species can be provided by passage of the deblocked, severed, peralkylated oligopeptide set through an anion exchange resin having the desired counterion as the exchangeable anion.

A $C_1$–$C_{18}$ acyl or pyroglutamoyl group is added by reaction of a corresponding anhydride such as acetic anhydride, acid halide such as octanoyl chloride, by reaction of a suitable activated ester such as N-hydroxysuccinimidyl benzoate or using the free carboxyl group and a carbodiimide such as DCC. An acyl group is usually added to a solid support-coupled oligopeptide upon removal of the selectively removable blocking (protecting) group, e.g. N-t-BOC or N-Fmoc, from the N-terminal a-amino group.

In those embodiments in which it is desired to have a free N-terminal a-amino group on each member of a peralkylated oligopeptide mixture set, a trityl (triphenylmethyl) group is preferably used to block the N-terminal amine prior to the peralkylation step. Once peralkylation is completed, the trityl group is removed by standard techniques such as treatment with an acid such as trifluoroacetic acid (TFA; 2 percent) in dichloromethane (DCM; 98 percent).

Where a single $C_1$–$C_7$-alkyl group is desired on the N-terminal amine, a solid support-linked free N-terminal amine-containing peralkylated oligopeptide mixture pool, prepared using a trityl group as above, is often first reacted with an excess, e.g., about two-fold, of 4,4'-dimethoxydiphenyl methylchloride (DodCl) following the procedures of Kaljuste et al., *Int. J. Peptide Protein Res.*, 42:118–124 (1993) to form a Dod-protected N-terminal amine. A $C_1$–$C_7$-alkyl aldehyde or ketone can then be used to reductively alkylate the Dod-protected N-terminal amine using a reducing agent such as sodium cyanoborohydride. The Dod-protecting group is thereafter removed as with 55 percent TFA in dichloromethane.

A Dod-protected N-terminal amine is used where monoalkylation is desired and the alkylating aldehyde or ketone is relatively small and unhindered as where formaldehyde or acetaldehyde is used. Monoalkylation using bulkier alkylating agents such as benzaldehyde does not require use of a Dod-protecting group, and is accomplished by direct reductive alkylation of the free N-terminal α-amine. Reductive alkylation of the free N-terminal α-amine with small, unhindered alkylating agents provides N,N-dialkylation. Alkylations between the two extremes can be achieved with a minimal amount of experimentation as to reaction conditions and reagents that is well within the level of ordinary skill in this art.

Exemplary $C_1$–$C_7$ aldehydes and ketones that can be utilized in this reductive alkylation include formaldehyde, acetaldehyde, acetone, butanal, methyl ethyl ketone, methyl butyl ketone and benzaldehyde. The $C_1$–$C_7$ aldehyde or ketone utilized in this step need not form the same $C_1$–$C_7$-alkyl group as resulted from the peralkylation step. Preferably, the single N-terminal alkyl group and that present after peralkylation are the same.

Where an oligopeptide mixture pool is coupled to the solid support by an ester group formed from the C-terminal residue via a direct bond or an intermediary linker such as a PAM group, and a C-terminal N-alkyl amide is desired in the peralkylated oligopeptide set, the oligopeptide set can be severed from the solid support by aminolysis using ammonia, and the resulting C-terminal amide becomes dialkylated when the peptide is alkylated after cleavage. Normal cleavage of an ester group-bonded oligopeptide from the solid support using HF results in a C-terminal carboxyl group. However, such esters cleave during sodium hydride treatment resulting in the carboxyl group being alkylated during the peralkylation step. The resulting ester can be cleaved with a base such as sodium hydroxide to form the corresponding carboxylate group that can be neutralized to form a free carboxyl group. That carboxyl group can also be alkylated by standard procedures to form a $C_1$–$C_7$-alkyl ester whose alkyl group is different from that of the peralkylated oligopeptide member chains. Cleavage of an amide-bonded oligopeptide from a benzhydrylamine resin solid support with HF prior to peralkylation results in the formation of a C-terminal N,N-dialkyl amide group after alkylation, whereas cleavage after peralkylation results in formation of a C-terminal N-alkyl amide group.

Syntheses of precursor oligopeptide sets is preferably carried out using foraminous (porous) containers that are described in U.S. Pat. No. 4,631,211, whose disclosures are incorporated by reference. Another useful synthetic technique, particularly for use in the chemical mixture process, is the process described in Lebl et al. U.S. Pat. No. 5,202,418, whose disclosures are incorporated herein by reference.

Various useful solid supports, methods of their use, reagents for linking the growing oligopeptide to the support, cleaving an oligopeptide from the support and the like are well known to workers skilled in this art such that further exemplification is unnecessary. Further such exemplifications can, however, be found in U.S. Pat. No. 4,631,211 and in WO 92/09300, published Jun. 11, 1992, whose disclosures are incorporated by reference.

D. Oligopeptide Peralkylation

A contemplated peralkylated oligopeptide set is alkylated at each amido nitrogen of the peptide backbone and side chain group at which an active hydrogen atom is present. An oligopeptide set is peralkylated with a reagent that provides a $C_1$–$C_7$-alkyl group. A precursor oligopeptide set is preferably peralkylated after preparation. A peralkylated oligopeptide set can also be prepared using appropriate peralkylated amino acid derivatives, but such a process is not convenient.

Contemplated $C_1$–$C_7$-alkyl groups with which an oligopeptide set is alkylated include hydrocarbyl and substituted hydrocarbyl alkyl groups. Exemplary hydrocarbyl groups include methyl, which is preferred, ethyl, propyl, iso-propyl, sec-butyl, cyclopentyl, hexyl, heptyl and benzyl, which can also be viewed as a phenyl-substituted methyl group or aralkyl group.

Substituted $C_1$–$C_7$-alkyl groups include alkyl carboxamide whose amido nitrogen atoms are themselves substituted with zero, one or two of the same $C_1$–$C_3$ hydrocarbyl alkyl groups, alkyl hydroxyl and alkyl carboxylate groups. Exemplary of such substituted alkyl groups are methylcarboxamide [—CH$_2$C(O)NH$_2$], 2-hydroxyethyl [—CH$_2$CH$_2$OH], 2-hydroxypropyl [—C$_2$CH(OH)CH$_3$] and 3-carboxypropyl [—CH$_2$CH$_2$CH$_2$CO$_2^-$]. As noted above, a benzyl group can also be viewed as a phenylmethyl group and can thus be viewed as a substituted alkyl group. The hydroxyl substituent is typically blocked with a trialkylsilyl group such as trimethylsilyl that can be removed after alkylation with tetrabutylammonium fluoride. A carboxyl-substituted alkyl group is preferably reacted as its alkali metal salt such as the sodium or potassium salt.

The peralkylation reaction can be carried out in a number of reaction conditions of non-nucleophilic strong base, solvent, temperature and concentrations of base and alkylating agent. The peralkylation reaction is a nucleophilic reaction so a polar, aprotic solvent such as dimethyl sulfoxide (DMSO), dimethyl formamide (DMF) or hexamethylphosphoramide (HMPA) is preferably used, DMSO being preferred. Minor amounts of the other aprotic solvents such as dioxane and tetrahydrofuran (THF) can also be present. The peralkylating agent is a before-described substituted or unsubstituted $C_1$–$C_7$-alkyl group that also includes an appropriate leaving group that is displaced during the reaction such as chloride, bromide, iodide, methylsulfonate or trifluoromethylsulfonate.

A ratio of about 50 to about 500 ml of DMSO or other solvent per gram of peptide-linked resin is preferably utilized. More preferably, this range is about 100 to about 250 ml/g, with the preferred solvent DMSO.

The alkylating agent is typically used in a large molar excess over the moles of active hydrogens present in the peptide to help assure peralkylation. The alkylating agent is typically used in about 10- to about 100-fold molar excess over the moles of peptide active hydrogen (potential alkylation sites), and preferably at about a 20- to about 80-fold, and more preferably, about 25- to about 40-fold, molar excess.

The non-nucleophilic strong base is preferably an alkali metal hydride such as sodium or potassium hydride. More preferably, the milder but still strong non-nucleophilic base lithium t-butoxide is used. The base must be of sufficient base strength to remove an active hydrogen from a peptidyl amide bond. An alkali metal hydride or t-butoxide ion has that required base strength and use of either minimizes side product formation as compared with other strong bases.

The non-nucleophilic strong base is used in large excess over the moles of possible peptide alkylation sites (active hydrogens). An about 5- to about 100-fold excess of base is typically used with an about 10- to about 30-fold excess being preferred. One preferred non-nucleophilic strong base is sodium hydride that is preferably used at about 0.25 molar in DMSO. The more preferred lithium t-butoxide in THF is used at about 0.5 molar.

In usual practice, the solid support-coupled precursor peptide is suspended in the solvent and admixed with the non-nucleophilic base for a time period of about 4 to about 24 hours prior to addition of the alkylating agent. A time period of about 16 to about 18 hours at ambient room temperature is typically used. This time period can be shortened to about 15–30 minutes with lithium t-butoxide as base.

The peralkylation reaction can be run at temperatures of below zero degrees C., such as at the temperature of a dry ice/acetone bath, to about the solvent boiling point, with lower temperatures requiring more time than higher temperatures. Peralkylation at ambient room temperature has been found to be quite effective and convenient and is thus preferred. The reaction is carried out under anhydrous conditions and preferably in an inert atmosphere such as under nitrogen or argon; i.e., in the absence of oxygen.

Methylation of peptide backbone nitrogen atoms has been shown to occur within about one minute, with N-terminal amines taking longer to permethylate. Thus, methylation reaction time is another way to prepare permethylated oligopeptide mixture sets having other than quaternary ammonium N-terminal groups. Mono- and dialkylamino N-terminal residues have been observed at a level that is generally less than about 15 percent.

As noted elsewhere, it is preferred to carry out the peralkylation while the oligopeptide set is linked to the solid support. Using the peptide synthesis techniques disclosed in U.S. Pat. No. 4,631,211 that utilized foraminous containers for the syntheses, several solid support-linked oligopeptide sets can be peralkylated at one time, each within its own foraminous container. It is believed that the present invention embodies the first report of permethylation of a peptide while that peptide is bonded to a solid support.

For peralkylation carried out with sodium hydride, the base, alkylating agent and peptide are typically present together in the reaction mixture. Using lithium t-butoxide in THF, the base and peptide are admixed and reacted, and then substantially all of the t-butoxide-containing liquid phase (as much as possible, e.g. about 75–95 percent) is removed. The alkylating agent in DMSO is thereafter admixed and reacted.

Once the peralkylation is complete, the excess non-nucleophilic strong base is washed away and neutralized by washing with DMSO, followed by DMF and dichloromethane, and the support-linked peralkylated peptide set (mixture pool) is then dried. Another washing protocol uses three washes with DMF, two with isopropyl alcohol (IPA), three with DCM and one with methanol (MeOH) prior to drying. The peralkylated oligopeptide sets can then be individually cleaved from the solid supports to provide free peralkylated oligopeptide sets, if desired, or a solid support-linked (-coupled) peralkylated oligopeptide set can be used without cleavage from the support.

Alkylation reactions involve the addition of a substituted or unsubstituted alkyl group to an atom such as carbon, oxygen, nitrogen or sulfur. Carbon alkylations are not contemplated here. As contemplated here, oxygen, nitrogen or sulfur atoms bonded to active hydrogen atoms; i.e., hydrogen atoms sufficiently acidic to be removed with a strong, non-nucleophilic base, are completely alkylated.

Thus, each peptide bond amide group is alkylated. The N-terminal a-amino group is quaternized if free, monoalkylated if present as an acyl amide or a Dod derivative, or unreacted if blocked as a cyclic imide such as succinimide, maleimide or phthalimide that is subsequently reacted with hydrazine or blocked with a trityl group.

Alkylation of amino acid residue side chains is a function of the blocking groups used during synthesis of the precursor oligopeptide chains. Thus, the non-reactive side chains that do not use blocking groups such as those of glycine, alanine, isoleucine, leucine, phenylalanine and proline are not alkylated. The amido side chains of asparagine and glutamine normally do not require blocking groups, but contain two active hydrogens on each side chain amide and are each dialkylated.

Using the usually used blocking groups in a N-t-BOC synthesis as exemplary, the following outlines the results of a contemplated peralkylation on various amino acid side chains.

Benzyl ether protecting groups of serine and threonine are stable to alkylation as is methionine sulfoxide so that those side chains are not alkylated where alkylation is carried out prior to deblocking. Methionine sulfoxide can be used as is, or reduced for use.

The formyl group preferably used to block the aza nitrogen of tryptophan is lost during alkylation so that an N-alkyl tryptophan (N-alkyl indole ring) is formed. The dinitrophenyl blocking group of the one blocked aza nitrogen of histidine is lost so that an N-alkyl histidine (N-alkylimidazole ring) results. The usually used β- and γ-benzyl ester blocking groups of aspartic and glutamic acids are lost during alkylation so those amino acid residues become alkylcarboxylate esters.

The usually used p-toluenesulfonyl, o-chlorobenzyloxycarbonyl and m-bromobenzyloxycarbonyl blocking groups of arginine, lysine and tyrosine are lost during peralkylation. The arginine and lysine residue side chains become quaternary alkylammonium groups, whereas the tyrosine hydroxyl becomes O-alkylated. After initial formation of a lysine quaternary ammonium group, some degradation can occur. Use of a cyclic imido blocking group on the ε-amino group of lysine followed by reaction with hydrazine can provide a free, unalkylated amine as such an imido nitrogen atom contains no active hydrogens.

Where cysteine is used, which is not preferred, the usually used p-methoxybenzyl blocking group is partly removed, leading to a mixture of alkylated and unalkylated mercaptyl groups after deblocking.

It is also noted that a contemplated set can include residues that are not peralkylated. Such residues can be added after a support-coupled mixture pool of peptides except that N-terminal residue is peralkylated using known peptide synthesis techniques for adding individual residues or mixtures of residues. The non-peralkylated residue is at one terminus or the other, depending upon the direction of peptide synthesis. Inasmuch as C-terminal to N-terminal synthesis is preferred, the non-peralkylated residues are preferably occupy the N-terminal positions.

The use of up to six non-peralkylated residues is contemplated. A total peptide length of two (zero non-peralkylated residues) to sixteen residues is contemplated. Preferably, only the N-terminal residue is not peralkylated.

Peralkylated Oligopeptide Sets and Libraries of Sets

One aspect of the present invention contemplates a set of linear peralkylated oligopeptide chains that comprises a mixture of equimolar amounts of linear peralkylated oligopeptide chain members, each member having an amino- and a carboxy-terminus, and containing the same number of two to about ten peralkylated amino acid residues in each chain. The members of the set have one or more (at least one) predetermined peralkylated amino acid residues at the same one or more predetermined positions of the peralkylated oligopeptide chain. A set also has equimolar amounts of peralkylated amino acid that contain at least six different peralkylated amino acid residues, preferably including the peralkylated residue at the at least one predetermined position, at one or more (at least one) of the same other positions of the peralkylated oligopeptide chain. The amino-terminus of each of the peralkylated oligopeptides in the set is quaternary alkylammonium, amino, N-alkylamino or a $C_1$–$C_{18}$ hydrocarboylalkylamido group, and the carboxy-terminus is a mono- or di-alkylamido, alkylcarboxylate or carboxyl group. A $C_1$–$C_7$-alkyl group at the, N- or C-terminus is a $C_1$–$C_7$-alkyl group that can be the same or different from the other $C_1$–$C_7$-alkyl groups present in each molecule.

A free peralkylated oligopeptide set is preferably prepared from a corresponding set of oligopeptides. A contemplated peralkylated oligopeptide set can also be solid support-bound and can be prepared from a complex mixture pool of solid support-coupled oligopeptides. For that reason, exemplary predecessor oligopeptide sets will first be discussed, with that discussion being followed by a discussion of the corresponding peralkylated oligopeptide sets, using the support-severed (free) oligopeptide sets and peralkylated oligopeptide sets as illustrative.

A complex mixture pool of solid support-coupled precursor oligopeptides, once deprotected and cleaved or severed from the solid support, is referred to herein as an oligopeptide set, an oligopeptide mixture set, by a similar phrase, or more simply as a "set". Being severed from the solid support, a precursor oligopeptide set is unsupported, and because of its method of synthesis, such a set is linear.

A precursor oligopeptide mixture set comprises a mixture of equimolar amounts of oligopeptide chains that contain the same number of amino acid residues in each chain; i.e., have the same chain length of 2 to about 10 residues, and more preferably about 5 to about 8 residues. A corresponding linear peralkylated oligopeptide set is similarly a mixture of peralkylated peptides of the same length, having the same number of 2 to about 10 peralkylated residues, and preferably 5 to about 8 peralkylated residues. The amino-terminus of each of the peralkylated oligopeptides in the set is quaternary alkylammonium, amino, N-alkylamino, a $C_1$–$C_{18}$ hydrocarboylalkylamido or a pyroglutamoyl group, and the carboxy-terminus is a mono- or di-alkylamido, alkylcarboxylate or a carboxyl group. A $C_1$–$C_7$-alkyl group at the N- or C-terminus is a $C_1$–$C_7$-alkyl group that can be the same or different from the other $C_1$–$C_7$-alkyl groups present in each molecule.

A precursor oligopeptide set has one or more (at least one) predetermined (specifically defined) amino acid residues at the same one or more (at least one) predetermined (specifically defined) positions of the oligopeptide chain and equimolar amounts of at least six different amino acid residues, more preferably at least ten different residues, and most preferably about 15 to about 20 different amino acid residues, at one or more (at least one) predetermined (specifically defined) other positions of the chain, the one or more predetermined residues preferably being one of the at least six different residues present in equimolar amounts. When more than one predetermined amino acid residue is present at more than one predetermined position of the chain, those residues can be the same of different. A corresponding peralkylated oligopeptide set has one or more (at least one) predetermined peralkylated amino acid residue at the same one or more (at least one) predetermined position of the peralkylated oligopeptide chain, and equimolar amounts of at least six different peralkylated amino acid residues at one or more (at least one) predetermined positions of the chain.

The number of amino acid residues for the equimolar mixture positions, and thus the number of different sets, is at least six, and more preferably about ten. Most preferably, that number is about 15 to about 20. The same is the case for peralkylated amino acid residues in a peralkylated set. It is often preferred to use 18 (t-BOC-synthesized) or 19 (Fmoc-synthesized) sets for each library; i.e., the naturally occurring 20 amino acids are used except cysteine that tends to cross-link and tryptophan that is difficult to couple and can also cross-link. However, tryptophan is often used at a predetermined terminal position as the at least one predetermined amino acid residue of a set even though it is not one of the residues utilized at equimolar mixtures positions.

In addition, where it is desired to use tryptophan in a precursor oligopeptide set or library, the tryptophan can be added to a growing solid phase-linked oligopeptide by the use of $N_\alpha$-t-BOC-N-formyl tryptophan that is available from Bachem, Inc., Torrence, Calif. Use of the formyl group protects against the adverse side reactions discussed before.

Where alkylation is carried out after cleavage from the solid-support, the N-formyl group can be removed during the usual side chain deprotecting step by the addition of a mercaptan-containing reagent such as ethanedithiol during the "low HF" deprotection reaction discussed herein. The N-formyl group can also be maintained during the side chain deprotection step by omission of the mercaptan-containing reagent during that step in which case that N-formyl group is replaced by an alkyl group on alkylation. Where a precursor oligopeptide set is alkylated while still bound to the solid support, the N-formyl group is replaced and the aza nitrogen atom of the indole ring is alkylated.

A preferred precursor oligopeptide mixture set contains the one or more predetermined residues at one or more predetermined positions that include a chain terminus, most preferably the N-terminus. Such a set also includes an equimolar amount of at least six different amino acid residues at one or more predetermined chain positions, and more preferably those chain positions are adjacent to one another. In particularly preferred practice, those adjacent equimolar mixture positions are at a terminus of the oligopeptide chain, and most preferably, that terminus is the C-terminus. Preferably, the same mixture of residues is present at each predetermined position.

In other embodiments, the N-terminal two precursor residues are predetermined residues within the set, the N-terminal three residues are predetermined, or the N-terminal four residues are predetermined when a set is six residues long or longer with the other positions being occupied by equimolar mixtures of residues. Thus, one or more predetermined chain positions at the precursor N-terminus are occupied by predetermined residues and one or more chain positions at the C-terminus are occupied by an equimolar mixture of residues.

In a corresponding linear peralkylated oligopeptide set, it is preferred that the one or more (at least one) peralkylated amino acid residue is (are) at the N-terminus, with the equimolar peralkylated residue mixture positions preferably including the C-terminus. It is also preferred that equimolar peralkylated residue positions be adjacent to each other.

For a precursor set six residues long or longer, an exemplary oligopeptide mixture set contains equimolar amounts of at least six different amino acid residues at the carboxy-terminal 1, 2, 3, 4 or 5 positions of the oligopeptide chain (i.e., positions 2, 3, 4, 5 and 6 from the amino-terminus of a 6-mer), as specifically defined position(s). At least one other position and preferably more than one other position of the chain of such a precursor oligopeptide mixture set is occupied by a predetermined amino acid residue whose identity is the same at an analogous position within the chain for each set, and those predetermined amino acid residues are most preferably at an amino-terminal position of the chain, including the amino-terminus of the chain. It is to be understood that although the identity of each predetermined residue at a given position in the chain is the same within each set, each such chain position can be occupied by the same or a different residue as between sets.

Exemplary precursor oligopeptide mixture sets include a dipeptide having one position predetermined and the other a mixture; a tripeptide having two positions occupied by predetermined residues and the other a mixture, or vice versa; a tetrapeptide having one predetermined position, e.g. position 1, and three mixture positions; a 5-mer whose first position is defined (predetermined) and whose remaining positions are occupied by mixtures; a 5-mer whose first and fifth positions are defined and whose second, third and fourth positions are occupied by mixtures; a 6-mer whose first two positions are predetermined and whose last four are occupied by mixtures; a hexamer whose first three positions are predetermined and whose last three are occupied by mixtures; a 7-mer whose first position and positions 4–7 are mixtures and whose second and third positions are predetermined; a 7-mer whose first, third and fourth positions are predetermined and whose remaining positions are mixtures; an 8-mer whose third and fourth positions are predetermined and whose remaining positions are occupied by mixtures of residues; an 8-mer whose first four positions are predetermined and whose last four positions are each mixtures; a 9-mer whose fourth and fifth positions are predetermined, and whose remaining positions are mixtures; a 10-mer whose positions 3–7 are predetermined, and whose remaining positions are occupied by mixtures; a 10-mer whose first position is predetermined, with the remaining positions occupied by mixtures; a 10-mer whose positions 7–9 are predetermined, with the remaining positions occupied by mixtures and the like where each mixture is an equimolar mixture of a plurality of coupled amino acid residues that includes at least 6, and more preferably at least about 10, and most preferably about 15 to about 20, different amino acid residues as discussed previously.

Corresponding linear peralkylated oligopeptide sets are contemplated for each of the above sets.

Precursor oligopeptide mixture sets that contain two chain positions of predetermined amino acid residues and four or more positions of equimolar mixtures along the chain are among those preferred. For 6-mers, those sets have the configurations of predetermined, single amino acid and equimolar mixtures shown below:

| Predetermined Positions | Mixture Positions |
|---|---|
| 1,2 | 3–6 |
| 2,3 | 1,4–6 |
| 3,4 | 1,2,5,6 |
| 4,5 | 1–3,6 |
| 5,6 | 1–4 |
| 1,3 | 2,4–6 |
| 1,4 | 2,3,5,6 |
| 1,5 | 2–4,6 |
| 1,6 | 2–5 |
| 2,4 | 1,3,5,6 |
| 2,5 | 1,3,4,6 |
| 2,6 | 1,3–5 |
| 3,5 | 1,2,4,6 |
| 3,6 | 1,2,4,5 |
| 4,6 | 1–3,5 |

Each of those positional configurations defines 400 mixture sets when the twenty natural amino acids are used. It is preferred that the predetermined residues, O, be adjacent to each other in the chain.

Precursor oligopeptide mixture sets containing three predetermined positions along the chain and three or more equimolar mixture positions are also preferred. Six-mer sets for those preferred sets have the configurations of predetermined, single amino acid and mixtures shown below:

| Predetermined Positions | Mixture Positions |
|---|---|
| 1–3 | 4–6 |
| 2–4 | 1,5,6 |
| 3–5 | 1,2,6 |
| 4–6 | 1–3 |
| 1,2,4 | 3,5,6 |
| 1,2,5 | 2,3,6 |
| 1,2,6 | 3–5 |
| 1,3,4 | 2,5,6 |
| 1,4,5 | 2,3,6 |

| Predetermined Positions | Mixture Positions |
| --- | --- |
| 1,5,6 | 2–3 |
| 1,3,5 | 2,4,6 |
| 1,3,6 | 2,4,5 |
| 2,3,5 | 1,4,6 |
| 2,3,6 | 1,4,5 |
| 3,5,6 | 1,2,4 |

Each of the above positional configurations defines 8000 oligopeptide mixture sets when the twenty natural amino acid residues occupy a predetermined position in the chain. It is preferred that the three predetermined positions be adjacent in the chain.

Using the twenty natural amino acids as exemplary, a precursor 6-mer (hexapeptide) mixture set having only the first position occupied by a predetermined residue has twenty member sets each of which contains 3.2 million member oligopeptides. A precursor set having the first two positions occupied by predetermined residues includes 400 member sets each of which includes 160,000 member oligopeptides.

The discussion as to precursor oligopeptide sets should be taken to apply to corresponding sets of linear peralkylated oligopeptides, including the above-discussed preferences as they apply to corresponding peralkylated sets.

In another particularly preferred embodiment, each precursor set comprises equimolar amounts of linear oligopeptide chains containing the same number of two to about ten amino acid residues in each chain. Each set, and its members, have only one, single, predetermined amino acid residue e.g. Ala, D-Val, Ser, etc., at a singly predetermined position of the oligopeptide chain, e.g. positions 1, 2, 3 . . . 10 from the amino-terminus.

Thus, each of the plurality of precursor sets has equimolar amounts of the same at least six different amino acid residues at the positions other than that of the single, predetermined amino acid present at the predetermined chain position, and that single residue is preferably one of the same at least six different amino acid residues. Each of the plurality of sets differs from the other sets by the single, predetermined amino acid at the predetermined chain position.

Using a 6-mer corresponding oligopeptide as exemplary, the positions of predetermined, single residue and positions of equimolar mixtures of residues are shown below.

| Predetermined Positions | Mixture Positions |
| --- | --- |
| 1 | 2, 3, 4, 5, 6 |
| 2 | 1, 3, 4, 5, 6 |
| 3 | 1, 2, 4, 5, 6 |
| 4 | 1, 2, 3, 5, 6 |
| 5 | 1, 2, 3, 4, 6 |
| 6 | 1, 2, 3, 4, 5 |

There is thus one set of precursor peptides for each of the single, predetermined amino acid residue at position 1. Because at least six amino acid residues are used in the mixture positions and each of those is also preferably used at position 1, the number of the plurality of position-1 sets is six. The same is true for each of the other positions. The sets defined by the position of the single, predetermined amino acid residues can be referred to as positional sets.

These positional sets of 6-mers can also be referred to as 5× sets because of their five mixture positions. Where the peptides are five residues long or have four mixture positions, the sets can be referred to as 4× sets, and so on.

Because there are six positions in the 6-mer, the number of libraries of precursor sets for the above group of positional sets is 6 times 6 or 36. There are, however, $6^6$ or 46,656 total oligopeptides represented by that library of sets. Use of 20 amino acid residues for the mixture positions of a 6-mer provides 6 times 20 or 120 positional sets, and a total of 64,000,000 individual oligopeptides.

The single, predetermined amino acid at the predetermined chain position is utilized in the equimolar mixture of amino acid residues present at those other positions. If that single, predetermined residue is not present in the mixture positions, the binding assay results of a library of peralkylated oligopeptides as to that residue lose some meaning as to that residue.

Corresponding linear peralkylated oligopeptide positional sets have a single predetermined peralkylated amino acid residue at a single predetermined repeating unit position with equimolar amounts of at least six different peralkylated amino acid residues at the other repeating unit positions of the chain. Each of the peralkylated sets differs from the other peralkylated sets by the predetermined peralkylated amino acid residue at the predetermined chain position.

It should be apparent from the foregoing discussion that a plurality of sets of linear peralkylated oligopeptide sets is also contemplated. Such pluralities of sets are referred to as libraries of sets. Each peralkylated oligopeptide member of each set of the library has one or more predetermined peralkylated amino acid residues at one or more predetermined positions of the peralkylated oligopeptide chain, the same termini and the same sequence of equimolar amounts of at least six different peralkylated amino acid residues at one or more predetermined positions in the peralkylated oligopeptide chain. The sets of peralkylated oligopeptide sets of the library differ in that at least one predetermined peralkylated residue present at a predetermined position within each set is different between the sets.

Exemplary libraries of sets are those corresponding to the previously discussed 400 oligopeptide sets whose first two peralkylated oligopeptide positions are each occupied by one of the twenty naturally occurring peralkylated amino acid residues, and the remaining positions 3–6 are occupied by equimolar mixtures. Each member of those 400 libraries has two predetermined peralkylated amino acid side chains ($O_1$ and $O_2$) at one or more predetermined positions (e.g., the N-terminal first two positions) and equimolar amounts of the at least six different peralkylated residues at one or more predetermined positions (e.g., the four C-terminal positions).

Another exemplary 6-mer set of peralkylated oligopeptide sets has the N-terminal first two positions occupied by predetermined peralkylated residues and the remaining positions occupied by mixtures of peralkylated residues. Similar sets of sets have positions 1–3 occupied by specific, predetermined peralkylated residues, the fourth position occupied by one of the peralkylated amino acid residues used in the study, and positions 5 and 6 occupied by mixtures of peralkylated residues. Another set of sets has the first four positions defined, the fifth occupied by each of the peralkylated amino acid residues used, and the sixth position a mixture.

Thus, the above library of sets is comprised of member sets each of which is comprised of a mixture of equimolar amounts of linear peralkylated oligopeptide chains containing the same number of peralkylated residues in each peralkylated oligopeptide chain; i.e., here each set has a sequence length of six repeating units. The members of each set have one to four N-terminal positions occupied by the same, single, predetermined peralkylated amino acid residue (the $O_1$, $O_2$, $O_3$ etc. positions) and four to one respective C-terminal positions occupied by equimolar amounts of at least six different peralkylated amino acid residues utilized (the equimolar mixture positions, X). The single position remaining in each set is the position between those enumerated above, and is occupied by one each of the peralkylated amino acid residues utilized at that position.

The number of sets within a library of sets is determined by the number of different peralkylated amino acid residues utilized at the above, single remaining position. Thus, where the peralkylated twenty naturally occurring amino acid residues are used, each set contains 20 mixtures. The number of individual peralkylated oligopeptides in each mixture of a set is determined by multiplying the numbers of peralkylated amino acid residues used at each equimolar mixture position.

The linear peralkylated oligopeptide positional sets of exemplary 6-mer sets (obtained by alkylation of the previously discussed corresponding 120 6-mer oligopeptide sets) each of which contains one predetermined position and five mixture positions are also contemplated, and illustrate particularly preferred library of peralkylated oligopeptide sets. Here, again, each set contains a sequence length of six repeating units. One position in each set is occupied by one of at least six of the predetermined peralkylated amino acid residues utilized for that position. The remaining five positions of each set are occupied by equal molar amounts of at least six different peralkylated amino acid residues. Again, the number of members of each set is determined by the number of predetermined peralkylated residues utilized, and the number of peralkylated oligopeptides in each set is determined by multiplying the numbers of peralkylated residues utilized at each equimolar mixture position.

The previously discussed mixtures having equimolar amounts of at least six different peralkylated amino acid residues occupying the four C-terminal positions also constitute a library of sets. Here, the sets contain a sequence length of five to ten peralkylated residues. The N-terminal peralkylated residue in each set is occupied by each one of the predetermined peralkylated amino acid residues utilized at that position (O). The repeating unit sequence between the enumerated N-terminus and four C-terminal positions is the same in each library from a C-terminal direction to an N-terminal direction.

Still further sets of peralkylated oligopeptides will be apparent to the skilled worker from the previous discussion and need not be gone into further here.

It is presently impossible to assay a mixture the complexity of those described herein. However, by using the synthetic methods discussed before, a skilled worker can construct a mixed precursor oligopeptide set, which upon hydrolysis and amino acid analysis has molar ratios of each amino acid to each other in the range of about 0.5 to about 1.5; i.e., the molar ratio of one amino acid residue to any other residue is 1:1±about 0.5, more preferably, this ratio is 1:1±about 0.25, which ratios carry through to the linear peralkylated oligopeptides.

Each chain of a set is also present in an equimolar amount and is of the same length (contains the same number of peralkylated residues) compared to the other chains present in the set. This equimolarity is also impossible to measure directly. However, by carrying out each reaction to completion and maintaining the previously discussed equimolarity, one can prepare chains that are of the same length and are present in equimolar amounts.

A precursor solid support-linked (-coupled) oligopeptide mixture set can also be directly alkylated to form a solid support-linked peralkylated oligopeptide set using a before-discussed reduction procedure. Alkylation while the peptide is linked to the support facilitates purification of the resulting set from unwanted reaction products.

Such a support-linked set can then be used in an assay as discussed hereinafter for binding to a soluble reactor such as an antibody or an external cellular receptor such as ELAM-1, but is not as useful for general assays for cellular receptors as is a free set.

It can also be useful for a peralkylated oligopeptide set to include a label. A radioactive label such as $^3$H can be used as part of an N-terminal acyl group of each member peralkylated oligopeptide.

Other contemplated labels include chromophores such as the 2,4-dinitrophenyl or 4-nitrophenyl groups and fluorescent molecules such as a dansyl group that can be coupled to an N-terminal amino group of a peralkylated oligopeptide using dansyl chloride (5-dimethylamino-1-naphthalenesulfonyl chloride).

A 2,4-dinitrophenyl or 4-nitrophenyl group can be coupled to an N-terminal amino group of a peralkylated oligopeptide set by means of an appropriate halogen derivative such as a chloro or fluoro group. The resulting nitrophenyl aniline derivatives have a yellow to yellow/orange color that can be readily observed.

It is also contemplated that a photoreactive label be coupled to a peralkylated oligopeptide set, particularly at the N-terminus. Exemplary photoreactive labels include the 4-azidobenzoyl and 4-azidosalicyl groups that are present as N-terminal amides prepared by reaction of the N-hydroxysuccinimide ester of either group with the free, N-terminal amino group. Each of the esters is available from Sigma Chemical Co., St. Louis, Mo.

Assay Processes and Peralkylated Oligopeptides

The present invention also contemplates a process for determining the sequence of a linear peralkylated oligopeptide ligand that preferentially (optimally) and specifically binds to an acceptor (receptor). Such a process can be carried out with the sets coupled to the sold support used for synthesis or with those sets not coupled to the solid support used for synthesis.

In accordance with one such process,
(a) a library of sets of linear peralkylated oligopeptides is provided in which each set comprises a mixture of equimolar amounts of linear $C_1$–$C_7$-alkyl peralkylated oligopeptide member chains containing the same number of two to about ten peralkylated amino acid residues in each peralkylated oligopeptide chain. Each peralkylated amino acid residue except proline has its peptidyl amino nitrogen atom alkylated with a $C_1$–$C_7$-alkyl group. As discussed previously, the member chains of each set have one or more (at least one) of at least six different predetermined peralkylated amino acid residues at one or more (at least one) predetermined positions of the peralkylated oligopeptide chain, and each set has equimolar amounts of at least six different peralkylated amino acid residues at the same one or more (at least one) other positions of the peralkylated oligopeptide chain. Preferably, the same at least six peralkylated residues are used at the mixture positions and the predetermined position. However, in some instances, the one or more predetermined positions of these sets are occupied by peralkylated residues not used in the mixture positions. The amino-terminus of each of the peralkylated oligopeptides in the set is quaternary alkylammonium, amino, N-alkylamino or a $C_1$–$C_{18}$ hydrocarboylalkylamido group, and the carboxy-terminus is mono- or di-alkylamido, alkylcarboxylate or carboxyl group. A $C_1$–$C_7$-alkyl group at the N- or C-terminus is a $C_1$–$C_7$-alkyl group that can be the same or different from the other $C_1$–$C_7$-alkyl groups present in each molecule. The sets of the library differ in that the one or more (at least one) predetermined peralkylated amino acid residues present at the one or more (at least one) predetermined chain positions within each set is different between the sets.

(b) Each set from the library of sets is separately admixed with the acceptor in an aqueous medium at a set concentration of about 0.1 milligrams (mg) per liter to about 100 grams per liter, and preferably about 1 milligram per liter to about 100 grams per liter, and more preferably about 100 milligrams per liter to about 20 grams per liter. The binding of each set to the acceptor is separately assayed, and the one or more sets of the plurality of sets that exhibits optimal or preferential, specific binding compared to the other sets assayed is determined, thereby identifying the one or more peralkylated residues that provide optimal or preferential binding at that one or more predetermined positions.

(c) A second library of sets of linear peralkylated oligopeptides is provided in which each set comprises a mixture of equimolar amounts of member $C_1$–$C_7$-alkyl linear peralkylated oligopeptide chains containing the same number of two to about ten peralkylated residues in each peralkylated oligopeptide chain (having the same chain length) as the chains of first-named library of sets. Each peralkylated amino acid residue except proline has its peptidyl amino nitrogen atom alkylated with a $C_1$–$C_7$-alkyl group. The members of each second library of sets contain the one or more peralkylated residues of the first library of sets identified as exhibiting optimal or preferential, specific binding in the one or more predetermined chain positions occupied in the first-named sets, and have one of at least six different predetermined peralkylated amino acid residues at another preferably adjacent predetermined position of the peralkylated oligopeptide chain different from the position of the one or more predetermined positions of the first-named library of sets. Each of the second library of sets has equimolar amounts of the same at least six different peralkylated amino acid residues as the first-named sets at the same one or more other positions of the alkylated oligopeptide chain not occupied by the one or more identified or predetermined peralkylated residues. The amino- and carboxy-termini of the peralkylated oligopeptides of the second library of sets are the same as those of the first-named sets. The second library of sets thus differ from the first library of sets in that at least two chain positions within the second set library are identified and predetermined (defined), and that second set library contains one fewer mixture positions than does the first set library.

(d) Each set from the second library of sets (of step c) is separately admixed with the acceptor in an aqueous medium at a concentration of about 0.1 milligrams per liter to about 100 grams per liter and preferably about 1 milligram per liter to about 100 grams per liter. The binding of each second library set to the acceptor is separately assayed and the one or more sets of the second library of sets that exhibits optimal or preferential, specific binding compared to the other sets assayed is determined, as discussed before, so that another peralkylated residue that provides optimal or preferential binding is determined.

(e) Steps (c) and (d) can be repeated with further, e.g., third, fourth, fifth, etc., libraries of sets until the desired number of set libraries, e.g. two through seven, (typically at least three for a 3-mer) have been assayed, each of those set libraries differing from the immediately previous library by having one more defined (predetermined) position occupied by one of at least six predetermined peralkylated residues, and one fewer predetermined repeating unit position occupied by equimolar amounts of at least six peralkylated residues. The repeats of steps (c) and (d) can alternatively be repeated until the last library assayed did not exhibit an increase in preferential, specific binding compared to the library assayed in the immediately preceding repeated assay. If that is the case, the sequence can be determined. Typically, however, the process continues, and individual peralkylated oligopeptides are prepared and assayed as discussed hereinafter. For example, the particular position assayed can be a position of redundancy within a longer sequence whose other as yet undefined positions, once defined, are needed for binding. A better binding or otherwise synthetically convenient residue is then used at the position where preferential binding was not exhibited.

Each of those further libraries of sets of linear peralkylated oligopeptides of (e) comprises a mixture of equimolar amounts of member linear $C_1$–$C_7$-alkyl peralkylated oligopeptide chains containing the same number of two to about ten peralkylated amino acid residues in each peralkylated oligopeptide chain as the chains of the first-named library of sets. Each peralkylated amino acid residue except proline has its peptidyl amino nitrogen atom alkylated with a $C_1$–$C_7$-alkyl group. The member chains of each further library of sets contain the peralkylated amino acid residues in the peralkylated oligopeptide chain positions that exhibited preferential, specific binding in a library of sets used immediately before and also one of at least six different predetermined peralkylated amino acid residues at another preferably adjacent predetermined position of the peralkylated oligopeptide chain that is different from the positions of the identified peralkylated amino acid residues of the library of sets used immediately before. Thus, each subsequent library of sets contains each of the previously identified peralkylated residues in the peralkylated oligopeptide chain position that exhibited preferential, specific binding, as well as a preferably adjacent predetermined peralkylated residue at a position in the peralkylated oligopeptide chain previously occupied by an equimolar mixture position. Each of those further library member sets also has the same termini as the first-named sets and has equimolar amounts of the at least six different peralkylated amino acid residues of said first-named sets at the same one or more positions of the peralkylated oligopeptide chain not occupied by the identified peralkylated amino acid residues or the predetermined peralkylated amino acid residues.

As noted previously, it is preferred that the one or more predetermined positions of the libraries of (a) are at one or the other terminus of the peralkylated oligopeptide chain, more preferably the N-terminus. It is also preferred that each new predetermined position in subsequently used sets be in a position adjacent to the position whose peralkylated amino acid residue was identified in the immediately previous assay. Thus, as each of steps (c) and (d) is repeated with new libraries of sets, one more position in the sequence becomes identified, and the sets contain one fewer mixture position.

In usual practice, once the preferential or optimal, specific binding peralkylated residues for all but the last position have been determined, at least six individual linear peralkylated oligopeptide chains are provided. These molecules contain the same number of $C_1$–$C_7$-alkyl peralkylated residues and same termini as did the chains of the first-named library of sets, and contain the peralkylated amino acid residues in the sequence determined by the above assays; i.e., the molecules contain each of the identified peralkylated residues at its position that exhibited preferential binding in the previous assays, and one each of the at least six peralkylated amino acid residues used at the final position. These at least six peralkylated oligopeptides are separately admixed with the acceptor and assayed for preferential or optimal, specific binding as discussed before. Determination of the peralkylated residue that exhibits preferential, specific binding as compared to the other peralkylated residues assayed from the results of this group of assays provides the last peralkylated residue of the sequence and thereby a preferential binding sequence for the linear peralkylated oligopeptide.

In usual practice, a peralkylated oligopeptide length; i.e., number of peralkylated residues in the chain, is selected and a complete sequence of a preferential, specific binding peralkylated oligopeptide is determined. In some instances, as noted before, preferential, specific binding does not increase when a further library is assayed; i.e., as additional known peralkylated residues are used in place of mixtures of peralkylated residues. In the latter case, the preferential, specific binding sequence is thus determined and it is unnecessary to utilize the at least six individual peralkylated oligopeptides as discussed above. If preferential, specific binding increases when each further library is used and assayed, the individual peralkylated oligopeptides discussed above are prepared and used.

The above assay process is particularly useful with sets prepared from the before-discussed 400 corresponding 6-mer oligopeptide sets in which two positions are of known sequence. Thus, after the first assay, the two N-terminal preferential, specific binding peralkylated residues are determined. In step (d), the third position is scanned for preferential, specific binding. This process is continued until the sequence of the N-terminal five peralkylated residues is known. Individual peralkylated oligopeptides are then usually used to complete the determination of the overall preferential, specific binding sequence by determining preferential, specific binding for the last position of this exemplary 6-mer.

Also preferred are sets and set libraries that are 5–10 peralkylated residues in length whose corresponding C-terminal four positions are occupied by peralkylated amino acid residue side chain mixtures, and whose corresponding amino-terminal positions are occupied by predetermined peralkylated residues. Each above set can be prepared from a single preparation of solid support-coupled 4-mer oligopeptide mixtures to which one or more predetermined acid residues is coupled, then peralkylated and cleaved following each acceptor binding assay.

For example, starting with a batch of support-coupled 4-mer oligopeptide mixtures whose positions are all equimolar mixtures, twenty mixtures can be prepared by separately coupling each of the twenty natural amino acids to a separate portion of the batch. After peralkylation of the precursor solid support-coupled mixture pool so prepared and cleavage, a binding assay is run as with a monoclonal antibody to determine preferential binding. Another library of twenty sets is then prepared using the same 4-mer batch with an optimal binding residue (after peralkylation) at position 2 in the sequence from the corresponding N-terminus and each of the twenty residues at position 1. The binding assay is run again after peralkylation and cleavage, and optimal binding is determined. This process is continued until a predetermined peralkylated oligopeptide sequence of desired length is completed. The use of C-terminal mixture positions that remain mixtures throughout helps improve the solubility of the set.

Another particularly preferred assay process utilizes library sets prepared from precursor positional oligopeptide sets, such as the library of 120 precursor 6-mer sets discussed before. Here, (a) a library of sets of linear peralkylated amino acid residue-containing oligopeptides in which each library comprises a mixture of equimolar amounts of $C_1$–$C_7$-alkyl linear peralkylated oligopeptide chains containing the same number of two to ten peralkylated residues in each peralkylated oligopeptide chain is provided. As discussed previously, the members of each set of the library have one of at least six different predetermined peralkylated amino acid residues at a single predetermined repeating unit position of the peralkylated oligopeptide chain, and N- and C-termini as discussed before. Each peralkylated amino acid residue except proline has its peptidyl amido nitrogen atom alkylated with a $C_1$–$C_7$-alkyl group. Each set has equimolar amounts of those same at least six different peralkylated amino acid residues at the same other positions of the peralkylated oligopeptide chain. As is the case with all of the sets discussed herein, it is preferred to use about 10 or more and more preferable to use about 15 to about 20 different peralkylated amino acid residues. A $C_1$–$C_7$-alkyl group at the N- or C-terminus is a $C_1$–$C_7$-alkyl group that can be the same or different from the other $C_1$–$C_7$-alkyl groups present in each molecule. The sets of the library differ in that the single predetermined peralkylated amino acid residue present at a single predetermined chain position within each set is different between the sets.

(b) Each set from the library of sets is separately admixed with the acceptor in an aqueous medium at a set concentration of about 0.1 milligrams per liter to about 100 grams per liter, and preferably about 1 milligram per liter to about 100 grams per liter. The binding of each set to the acceptor is separately assayed, and the one or more sets of the library of sets that exhibits preferential, specific binding compared to the other sets assayed is determined, thereby identifying the one or more peralkylated residues that provide preferential binding at that single, predetermined position.

(c) A second library of sets of linear peralkylated oligopeptides is provided in which each set comprises a mixture of equimolar amounts of linear $C_1$–$C_7$-alkyl peralkylated oligopeptide chains containing the same number of two to ten peralkylated residues in each peralkylated oligopeptide chain (having the same chain length) as the first-named library of sets. Each peralkylated amino acid residue except proline has its peptidyl amido nitrogen atom alkylated with a $C_1$–$C_7$-alkyl group. The members of each second library set have the same N- and C-termini as the first library set member chains, and have one of the same at least six different predetermined peralkylated amino acid residues of the first-named sets at another single predetermined position of the peralkylated oligopeptide chain different from the position of the first-named library of sets, and each of these sets has equimolar amounts of the same at least six different peralkylated amino acid residues at the same other positions of the peralkylated oligopeptide chain. The second library of sets differs from the first library of sets in that the single predetermined chain position within each set that contains the one of at least six different peralkylated residues is different between the libraries.

Put differently, the second library of sets has the same length and termini as the first-named library, and has equimolar amounts of the at least six peralkylated residues at the peralkylated oligopeptide chain position occupied by the single peralkylated residue in the first-named set library, and a single peralkylated residue in a position occupied by equimolar amounts of peralkylated residues in the first-named library sets. For example, the first named library of sets can have its single one of at least six different predetermined peralkylated amino acid residues at position 1 with the other positions occupied by mixtures, whereas this second library of sets has its single predetermined peralkylated amino acid residues at any of positions 2–10, and equimolar amounts of at least six different peralkylated residues at position 1, and the remaining chain positions other than that occupied by the single peralkylated residue.

(d) Each set from the second library of sets (of step c) is separately admixed with the acceptor in an aqueous medium at a concentration of about 0.1 milligrams per liter to about 100 grams per liter and preferably about 1 milligram per liter to about 100 grams per liter. The binding of each second set to the acceptor is separately assayed and the one or more sets of this second library of sets that exhibits preferential, specific binding compared to the other sets assayed is determined, thereby identifying a peralkylated amino acid residue that provides preferential binding at that predetermined position in the peralkylated oligopeptide chain.

(e) Steps (c) and (d) are repeated with third, fourth, fifth, etc. up to the number of residues in the chain length, libraries of sets until the desired number of set libraries have been assayed, each of those set libraries differing from the other libraries by the position that contains the one of at least six different peralkylated amino acid residues. It should also be apparent that where peralkylated dipeptides are used, the process is stopped so that steps (c) and (d) can be repeated zero times.

The identity and position of the $C_1$–$C_7$-alkyl peralkylated amino acid residue of each one or more sets that provided preferential or optimal, specific binding so determined for each library of sets provides the identity of a peralkylated residue sequence for the ligand that preferentially, specifically binds to the acceptor. Thus, because each of the libraries of positional sets assayed provides the identity of a peralkylated residue(s) that provide(s) enhanced binding for that position, and because there is equimolar representation of all the other peralkylated residues at the mixture positions, knowledge of the identity and position of peralkylated residues that provide enhanced binding for the utilized positions provides a sequence for a ligand or donor-peralkylated oligopeptide that provides enhanced binding.

It should be understood that determining the identity and position of two peralkylated residues that each provide greatly enhanced binding can be extremely useful when preparing completed peralkylated peptides because several fewer such peralkylated peptides need be prepared. Of course, knowledge of three identities and positions is more preferred, and knowledge of four is more preferred still, etc.

The above process is referred to as a scanning process in that peralkylated residues at each position of a sequence are individually scanned.

It is preferred that, as a group, the single, predetermined repeating unit positions be adjacent to each other. Thus, exemplary sets for positions 1–3 of a trimer, or positions 2–6 of a hexamer are used or 1–6 of a decamer peralkylated oligopeptide are used, as compared to positions 1, 2 and 4–8 of an octamer.

It should be understood that although it is preferred to scan adjacent repeating unit positions, one need not utilize the pluralities of sets in any order by position. Thus, although convenient, one need not use the libraries of sets that contain the one of at least six different predetermined peralkylated residues at position 1 followed by the libraries having the one of at least six different predetermined side chains at position 2, and so on.

In addition to there being no need to utilize the libraries of positional sets in any order, it is also not necessary to utilize a single library of positional sets followed by another and another, etc. Rather, one can utilize the individual sets in any order because the position and identity of the single one of at least six different predetermined peralkylated amino acid residues of each library is known. This is in contrast to the previously discussed process where it is preferred to use a predetermined peralkylated residue adjacent to an identified peralkylated residue.

Thus, a more general scanning process is also contemplated. Here, (a) a library or plurality of sets of linear peralkylated oligopeptides is provided. Each set of that library or plurality of sets comprises a mixture of equimolar amounts of linear $C_1$–$C_7$-alkyl peralkylated oligopeptide chains containing the same number of two to about ten peralkylated residues in each chain, and having N- and C-termini as discussed before. Each peralkylated amino acid residue except proline has its peptidyl amido nitrogen atom alkylated with a $C_1$–$C_7$-alkyl group. Each set has a single one of at least six different predetermined peralkylated amino acid residues at a single, predetermined position of the peralkylated oligopeptide chain, and has equimolar amounts of each of the same at least six different peralkylated amino acid residues at the same other positions of the peralkylated oligopeptide chain. A $C_1$–$C_7$-alkyl group at the N- or C-terminus is a $C_1$–$C_7$-alkyl group that can be the same or different from the other $C_1$–$C_7$-alkyl groups present in each molecule. Each set differs from the other sets in that the identity and chain position of the one of at least six different predetermined peralkylated amino acid residues present at the single predetermined chain position within each set is different between the sets. The maximum number of sets provided is equal to the product of the number of different amino acid residues present at the predetermined chain positions containing the one of at least six different residues times the number of different chain positions containing the one of at least six different predetermined peralkylated amino acid residues.

(b) Each set is separately admixed with the acceptor in an aqueous medium at a set concentration of about 0.1 milligrams per liter to about 100 grams per liter and preferably about 1 milligram per liter to about 100 grams per liter. The binding of each set to the acceptor is separately assayed for each set. The one or more sets that provide preferential, specific binding for each different chain position is determined.

The identity and position of the $C_1$–$C_7$-alkyl peralkylated residue of each one or more sets that exhibited preferential, specific binding provides the peralkylated residue sequence for the ligand that preferentially binds to the acceptor.

Although an above process can be carried out with peralkylated dipeptide sets, it is preferred to use sets of at least pentamers. Thus, at least five libraries of positional sets are typically utilized (scanned). It is preferred, but not necessary, that those five libraries of sets, as a group, contain single, predetermined peralkylated residues at adjacent positions in the sequence. For example, in a 5-mer, those positions would be 1–5 of the sequence. However, in a 10-mer, those positions could be positions 6–10, 5–9, 3–7 or the like. Of course, one obtains more precise sequence identification information if adjacent positions of the peralkylated oligopeptide chain are determined, and if the identity of the peralkylated residue exhibiting enhanced binding for each chain position is determined.

Those identified $C_1$–$C_7$-alkyl peralkylated residues that exhibit preferential binding within about a factor of two of a best binding side chain at that position are typically considered to exhibit preferential or optimal, specific binding and are used to prepare one or more peralkylated oligopeptides using the other identified peralkylated residues at the other positions to determine which combination provides optimal or preferential overall properties. Thus, using a 6-mer as exemplary, although one may not be able to determine a single optimal sequence out of the 64,000,000, the field is typically cut down to about 5–50 or sometimes thousands of sequences, which because of their sequential similarity, can be readily prepared by the SMPS method discussed in U.S. Pat. No. 4,631,211, followed by reduction. Even where the scanning process narrows the possible optimal binding linear peralkylated oligopeptide sequences to several thousand, the worker's knowledge has been advanced, and he or she can use a peptide synthesis method described in WO 92/09300, or Houghten et al., *Nature*, 354:84 (1991), in U.S. Pat. Nos. 5,010,175, 5,182,366 or 5,144,392 followed by peralkylation to complete the sequence or obtain new optimal binding sequences.

In any assay discussed herein, all of the at least six different predetermined peralkylated residues at a predetermined position can provide similar specific binding. That phenomenon is referred to as positional redundancy or redundancy, and any convenient peralkylated residue is utilized at that position when a peralkylated oligopeptide ligand is synthesized.

The aqueous medium used in an assay can be extremely varied and includes tap water, distilled or deionized water, as well as a buffer solution as is used for antibody binding studies or a cell growth medium as is useful for culturing bacteria, yeast, fungi, plant or animal cells, all of which are well known to skilled workers.

The concentration of a linear peralkylated oligopeptide set in the aqueous medium is selected so that the peralkylated oligopeptide set is present at concentrations of about 0.1 milligrams per liter to about 100 grams per liter, preferably about 1.0 µg/ml to about 100 mg/ml, and more preferably about 0.1 mg/ml to about 20 mg/ml. Thus, when each peralkylated oligopeptide mixture is made up of 3.2 million individual peralkylated oligopeptides; e.g. a permethylated C—N-methylamide 6-mer oligopeptide using the 20 natural amino acid residues, then each 6-mer peralkylated oligopeptide within each mixture is present in a preferred concentration of about 1.0 µg/ml/3,200,000=0.31 pg/ml, to about 100 mg/ml/3,200,000=31.25 ng/ml. Presuming an average molecular weight of a permethylated C-terminal N-methylamide 6-mer peralkylated peptide to be about 800 g/mole, then at 1.0 µg/ml, the individual hexamers are present at a concentration of about 0.4 pmolar and at 100 mg/ml the individual hexamers are present at about 40 nmolar. Most preferably, concentrations of about 0.5 mg/ml to about 10 mg/ml are used.

It is preferred, although not required, that a peralkylated oligopeptide mixture set be soluble in the aqueous medium utilized. Thus, the permethylated N-terminal quaternized oligopeptide sets are typically soluble in most aqueous media, whereas sets alkylated with more hydrophobic alkyl groups form milky dispersions. Such dispersions are nonetheless useful. For example, the free N-terminal amino perbenzylated single peptide GlyGlyPheLeu SEQ ID NO:36 formed an opaque dispersion in water containing 10 volume percent DMSO at 1 mg/ml. Similar dispersions were prepared from peralkylations with ethyl and allyl groups.

As is well known, complete water-solubility is not required for a drug, as many commonly used drugs such as steroids are substantially insoluble in water, aqueous assay media or body fluids, but are nonetheless extremely valued medicaments. For example, the *Merck Index*, 10th ed., lists both progesterone and testosterone as being insoluble in water and estradiol as being almost insoluble in water.

It is to be understood that the wide breadth of concentrations specified above is intended to take into account the contemplated range of peralkylated oligopeptide sets that can have up to nine positions as mixtures, one to about four alkyl groups per residue, alkyl groups of varying molecular weight and the fact that wide ranges of concentrations are often used for determining $IC_{50}$ and $K_i$ values.

A peralkylated oligopeptide set and its individual members can be looked at as donor (ligand) in donor-acceptor (receptor) binding complex formation. Exemplary acceptor molecules are antibody combining site-containing molecules such as whole antibodies, F(ab), F(ab')$_2$ and Fv antibody portions, solubilized or non-solubilized cell surface receptor molecules, such as the solubilized CD4 receptor, internal cellular receptors and viral protein receptors, all but the antibody combining site-containing molecules being collectively referred to as "cellular receptors". "Cellular receptors" also include living cells that contain receptors that interact with a peralkylated oligopeptide library as ligand (donor).

The binding interactions assayed for here are specific binding interactions such as those between antibody and antigen. Such specific binding interactions are to be compared to the non-specific binding that is observed between most proteins and the plastics used in microtiter plates.

Any well known binding or binding inhibition assay format can be used. For example, a solid phase assay using a solid phase-bound antibody binding site and a radiolabeled peralkylated oligopeptide set is contemplated. Also contemplated is a competitive binding assay in which a protein or polypeptide is bound to a solid phase as an antigen and a monoclonal antibody binding to that antigen is admixed with a peralkylated oligopeptide set. Inhibition of binding of the monoclonal antibody by the peralkylated oligopeptide set provides a measure of the binding between the peralkylated oligopeptides and monoclonal antibody. Monoclonal antibody binding inhibition and the inhibition of other acceptors' binding can be assayed using enzyme or radiolabels as is well known.

It is often the case that one has receptors (acceptors) such as antibodies to a particular ligand such as an antigen, but the specific ligand (antigen) that binds those antibodies is unknown. Under these circumstances, usual solid phase assays in which the ligand is affixed to a plate or other solid phase matrix cannot be carried out because the relatively short peralkylated oligopeptide sets contemplated herein do not bind well to microtiter plate walls and similar solid phase matrices.

Avidin binds well to microtiter plate walls and similar matrices. Use of that fact and its well known binding partner, biotin, can be made for those assays in which the ligand bond by the receptor is unknown or is otherwise unavailable.

Thus, avidin is coated on a solid phase matrix such as microtiter plate walls using standard, well known techniques such as adsorption. Biotin, which contains a free carboxyl group, is coupled to the N-terminal amine of a before-described peralkylated oligopeptide set via the biotin carboxyl group, using usual coupling chemistry as described herein for coupling amino acids. The biotinylated set is dissolved in an aqueous medium and admixed with the avidin-coated solid phase matrix to form a solid/liquid phase admixture. That admixture is maintained for a time period sufficient for the avidin and biotinylated peralkylated oligopeptide set complex, typically five minutes to about five hours, and form a biotinylated peralkylated oligopeptide set-containing solid support and a liquid phase depleted of biotinylated peralkylated oligopeptide. The solid and liquid phases are then separated, and the solid support is typically washed.

The thus prepared solid support that contains an affixed peralkylated oligopeptide set, is then utilized with the receptor (acceptor) in standard solid phase assays. Where the receptor is an antibody, usual detecting systems such as the use of radiolabeled or enzyme-linked anti-antibodies such as goat anti-mouse antibodies where the receptors are mouse antibodies are utilized to detect binding. Where the receptor is a cellular receptor, radiolabels incorporated into the receptor by culture of the cells in a medium containing radioactive amino acids are typical detecting means of choice.

It is frequently convenient to provide a spacer group between the peralkylated oligopeptides of a set and the biotin. Exemplary spacers include one to about five glycine, $C_2-C_6$ straight chain ω-amino acids such as glycine, α-alanine, 4-aminobutyric acid (GABA) or 4-aminocaproic acid.

Thus, a N-terminal biotinylated peralkylated oligopeptide set as otherwise described before is also contemplated. That biotinylated peralkylated oligopeptide set can further include one to about five $C_2-C_6$ straight chain ω-amino acid residues between the N-terminal amine of the peralkylated oligopeptides and the biotin group.

For a before-discussed chromophore- or fluorescent-labeled peralkylated oligopeptide set, contact between the acceptor and peralkylated oligopeptide set can be carried out with the acceptor linked to a solid support such as sepharose or agarose.

The non-binding and poorer binding sets can be separated from the solid support-bound acceptor molecules by washing at increasingly higher salt concentrations until a predetermined concentration is reached that is used to define a better or preferential binding peralkylated oligopeptide. The choromophoric or fluorescent label can be used to follow the elution. Using the 2,4-dinitrophenyl chromophore as exemplary, the presence of a yellow to yellow/orange color on the solid support for a given set after washing indicates an optimal binding set.

An exemplary assay using a photoreactive label can be carried out with an enzyme having a known substrate. Here, the enzyme as acceptor and photoreactive labeled, peralkylated oligopeptide set are admixed and the admixture maintained so that binding can occur. The admixture is then irradiated using sufficient quanta of light at an appropriate wavelength, as are well known, to cause the decomposition of the photoreactive group such as an azide group and the insertion of the resulting peralkylated oligopeptide containing radical into the enzyme polypeptide backbone. That insertion links the peralkylated oligopeptide to the enzyme and blocks reaction with the enzyme's substrate. Thus, an assay of enzymic activity after irradiation provides a determination of which peralkylated oligopeptide set bound optimally, with a diminished activity indicating enhanced binding.

Cellular receptor molecules are also particularly contemplated as useful in this assay system. The cellular receptor whose binding is contemplated for assay need not be isolated, but can be part of an intact, living cell such as bacterial, yeast, fungal, mammalian or plant cells, or viruses. When such intact, living cells are utilized, relative binding amounts can be determined by the growth or inhibition of growth of the admixed, assayed cells. The aqueous medium here is a growth or culture medium, known to promote growth of the assayed cells.

The concentration of free acceptor molecules, including those obtained from cell preparations or those present in intact, living cells used for such binding assays is an assay-effective amount such as is normally used for such assays, and is well known in the art. It is to be understood that different concentrations of free acceptor molecules or those present in intact, living cells can vary with each acceptor studied.

A before-described assay can be carried out in vitro as well as being carried out in vivo. For in vivo assays, living plants such as tobacco, alfalfa, corn (maize), zinnias and the like are contemplated hosts, whereas small laboratory mammals such as rats, mice, guinea pigs, rabbits and dogs are contemplated hosts for animal assays.

A $C_1-C_7$-alkyl peralkylated oligopeptide set-containing composition can be administered and a $C_1-C_7$-alkyl peralkylated oligopeptide contacted with the acceptors internally or externally in plants through watering, misting of foliage, or injection. For the animals, a composition can be administered internally, orally or by injection such as intraperitoneally, subcutaneously or intramuscularly or topically as by application to skin for the contact between donor and acceptor to take place.

Binding here can be assessed by relative growth rate (positive or negative) or by the affect of the composition on one or more tissues, as through microscopic examination, by body temperature where pathogen-infected animals are used, and the like as are well known.

Peralkylated Oligopeptides

Several peralkylated individual oligopeptides were prepared based on the studies discussed hereinafter. Ten permethylated hexamers, a pentamer, heptamer and octamer were found to be particularly and selectively active against Gram-positive bacteria [Staphylococcus (S.) aureus, a methicillin-resistant strain of S. Aureus, and Streptoccus (S.) sanquis], while having substantially no activity against E. coli, Gram-negative bacteria, or Candida albicans, a yeast; $IC_{50}$, >600 µg/ml. These permethylated oligopeptides also exhibited substantially no lysis of human red blood cells at concentrations equal to their $IC_{50}$ values, and no to minor amounts of lysis at a concentration about 10- to about 100-fold greater than their $IC_{50}$ values; i.e., at 350 µg/ml. An absence of in vitro toxicity toward McCoy cells (ATCC 1696-CRL) using an MTT [3-(4,5-dimethylthiazol-2-yl)-2,5-diphenyltetrazolium bromide; Mosmann, J. Immunol. Methods, 65:55–63 (1983)] assay was also noted for these materials. These facts, coupled with the observed stability of permethylated peptides to proteolytic enzymes, the excellent water-solubility exhibited by the peptides and the favorable aqueous/organic solvent partitioning enhance the value of these permethylated oligopeptides as Gram-positive antibacterial agents.

These particularly preferred permethylated oligopeptides are listed below using the prefix "PerM-" to indicate permethylation. Each permethylated oligopeptide contains a C-terminal N-methylamide, that is not shown and an N-terminal trimethylammonium group that is also not shown.

| | |
|---|---|
| PerM-LeuPheIlePhePhePhe | (SEQ ID NO:26); |
| PerM-PhePheIlePhePhePhe | (SEQ ID NO:27); |
| PerM-PhePhePhePhePhePhe | (SEQ ID NO:23); |
| PerM-LeuPhePhePhePhePhe | (SEQ ID NO:28); |
| PerM-PhePhePhePheHisPhe | (SEQ ID NO:29); |
| PerM-LeuPheIlePhePheHis | (SEQ ID NO:30); |
| PerM-LeuPhePhePheHisPhe | (SEQ ID NO:31); |
| PerM-LeuPheIlePheHisPhe | (SEQ ID NO:32); |
| PerM-LeuPhePhePhePheHis | (SEQ ID NO:33); |
| PerM-PhePheIlePhePheHis | (SEQ ID NO:34); |
| PerM-PhePhePhePhePhe | (SEQ ID NO:22) |
| PerM-PhePhePhePhePhePhePhe | (SEQ ID NO:24); | and

| | |
|---|---|
| PerM-PhePhePhePhePhePhePhePhe | (SEQ ID NO:25). |

The first ten permethylated oligopeptides correspond to the formula

Xaa$_1$PheXaa$_3$PheXaa$_5$Xaa$_6$,     (SEQ ID NO:35)

wherein Xaa$_1$ at the first position is a N-trimethylammonium Leu or Phe residue;

Xaa$_3$ at the third position is Ile or Phe;

Xaa$_5$ at the fifth position is His or Phe; and

Xaa$_6$ at the sixth position is a C-terminal N-methylcarboxamido His or Phe residue, with the proviso that at least one of Xaa$_5$ and Xaa$_6$ is Phe. When each of Xaa$_1$, Xaa$_3$Xaa$_5$ and Xaa$_6$ is Phe, a permethylated peptide of SEQ ID NO:23 results.

The above list also illustrates that permethylated C-terminal N-methylamido oligophenylalanine (oligophe) having 5 through 8 Phe residues are contemplated. These permethylated oligopeptides also have an α-N-terminal trimethylammonium group. Of these permethylated oligophe C-terminal N-methylamido peptides, compounds having 6, 7 or 8 Phe residues are most preferred; i.e., SEQ ID NO's: 23, 24 and 25.

The following examples are intended to illustrate, but not limit, the invention.

EXAMPLE 1

Exemplary Synthesis of a Set of Mixed Oligopeptides having Equimolar Amounts of the Twenty Natural Amino Acid Residues

Aliquots of five grams (4.65 mmols) of p-methylbenzhydrylamine hydrochloride resin (MBHA) are placed into twenty porous polypropylene bags. These bags are placed into a common container and washed with 1.0 liter of $CH_2Cl_2$ three times (three minutes each time), then again washed three times (three minutes each time) with 1.0 liter of 5 percent $DIEA/CH_2Cl_2$ (DIEA=diisopropylethylamine; $CH_2Cl_2$=DCM). The bags are then rinsed with DCM and placed into separate reaction vessels each containing 50 ml (0.56M) of the respective t-BOC-amino acid/DCM. N,N-Diisopropylcarbodiimide (DIPCDI; 25 ml; 1.12M) is added to each container, as a coupling agent.

Twenty amino acid derivatives are separately coupled to the resin in 50/50 (v/v) DMF/DCM. After one hour of vigorous shaking, Gisen's picric acid test [Gisen, *Anal. Chem. Acta*, 58:248–249 (1972)] is performed to determine the completeness of the coupling reaction. On confirming completeness of reaction, all of the resin packets are then washed with 1.5 liters of DMF and washed two more times with 1.5 liters of $CH_2Cl_2$.

After rinsing, the resins are removed from their separate packets and admixed together to form a pool in a common bag. The resulting resin mixture is then dried and weighed, divided again into 20 equal portions (aliquots), and placed into 20 further polypropylene bags (enclosed). In a common reaction vessel the following steps are carried out: (1) deprotection is carried out on the enclosed aliquots for thirty minutes with 1.5 liters of 55 percent TFA/DCM; and 2) neutralization is carried out with three washes of 1.5 liters each of 5 percent DIEA/DCM.

Each bag is placed in a separate solution of activated t-BOC-amino acid derivative and the coupling reaction carried out to completion as before. All coupling reactions are monitored using the above quantitative picric acid assay. Next, the bags are opened and the resulting t-BOC-protected dipeptide resins are mixed together to form a pool, aliquots are made from the pool, the aliquots are enclosed, deprotected and further reactions are carried out.

This process can be repeated any number of times yielding at each step an equimolar representation of the desired number of amino acid residues in the peptide chain. The principal process steps are conveniently referred to as a divide-couple-recombine (DCR) synthesis.

After a desired number of such couplings and mixtures are carried out, the polypropylene bags are kept separated to here provide the twenty sets having the amino-terminal residue as the single, predetermined residue, with, for example, positions 2–4 being occupied by equimolar amounts of the twenty residues. To prepare sets having the single, predetermined amino acid residue at other than the amino-terminus, the contents of the bags are not mixed after adding a residue at the desired, predetermined position. Rather, the contents of each of the twenty bags are separated into 20 aliquots, deprotected and then separately reacted with the twenty amino acid derivatives. The contents of each set of twenty bags thus produced are thereafter mixed and treated as before-described until the desired oligopeptide length is achieved.

The side chain protecting groups used with a-amino-terminal t-BOC and Fmoc protecting groups are usually different. The side chain protecting groups utilized for one type of synthesis or the other are as shown in the table below. Other usually used side chain protecting groups are also utilized for both types of syntheses.

| Amino Acid Derivative | Side Chain Protecting Group | |
|---|---|---|
| | N-t-BOC Protected | N-Fmoc Protected |
| Arginine | Toluenesulfonyl* | Mtr** |
| Cysteine | p-Methoxybenzyl | t-Butyl ether |
| Glutamic acid | O-Benzyl | t-Butyl ester |
| Histidine | N-im-dinitrophenyl* | Trityl |
| Lysine | N-(o-chlorobenzyl-oxycarbonyl) | t-BOC |
| Serine | O-Benzyl | t-Butyl ether |
| Threonine | O-Benzyl | t-Butyl ether |
| Tyrosine | O-(m-bromobenzenyl-oxycarbonyl) | t-Butyl ether |
| Aspartic acid | O-Benzyl | t-Butyl ester |

*Arginine and histidine are coupled in the presence of N-hydroxylbenztriazole [Hruby et al., Angew. Chem. Int. Ed. Engl., 10:336–339 (1971)].
**Mtr = 4-Methoxy-2,3,6-trimethylbenzenesulfonyl.

For precursor oligopeptide mixture sets not having an N-terminal $C_1$–$C_{18}$ acyl (e.g. acetyl) group, the following procedure is used for side chain deprotection of N-t-BOC-protected oligopeptide chains. The fully protected solid support-coupled oligopeptide mixtures are treated with 55 percent trifluoroacetic acid in methylene chloride prior to the HF treatment to remove the final t-BOC-protecting group. Then the protected solid support-coupled oligopeptide mixtures, in polypropylene mesh packets [Houghten, Proc. Natl. Acad. Sci., USA, 82:5131–5135 (1985)] are rinsed with alternating washes of DCM and isopropanol, and dried under reduced pressure for twenty-four hours.

Where cleavage from the solid support is carried out prior to alkylation, the low HF step [Tam et al., J. Am. Chem. Soc., 195:6442–6455 (1983)] is carried out in a two liter polypropylene reaction vessel, using a solution of 60 percent dimethylsulfide, 25 percent HF, 10 percent p-cresol and 5 percent ethylenedithiol. The ethanedithiol is used to cleave the N-formyl groups from tryptophan residues. Where it is desired not to cleave the N-formyl groups, ethanedithiol is omitted from the mixture and its amount is replaced by HF. $N_\alpha$-t-BOC-N-formyl tryptophan is available from Bachem, Inc., Torrence, Calif.

HF is condensed at −78° C. After condensation, the HF-scavenger solution is carefully transferred to the reaction vessel that contained the resin-containing packets. The low HF solution is made to give 5 ml per 0.1 mmol of oligopeptide. After the reagents are added, the reaction vessel is placed in an ice water bath and shaken for two hours. The low HF solution is removed and the packets containing the deprotected peptide resins are quickly washed with chilled DCM. The DCM wash is repeated nine times (one minute each) followed by ten alternating washes of isopropanol and DCM. Finally, the resin is washed five times with DMF, then twice more with DCM. Deprotected peptide resin packets are dried under reduced pressure. After this process is completed, the unprotected peptides are ready to be cleaved by anhydrous HF.

The N-terminal Fmoc protecting groups of enclosed, protected solid support-coupled oligopeptide mixtures are removed by treatment with twenty percent piperidine in DMF for ten minutes. Then the resulting N-deprotected, side chain-protected peptide resins in polypropylene packets are washed with DMF twice (five minutes each) followed by two rinses with DCM (one minute each) and dried in a vacuum for twenty-four hours.

The side chain deprotection is carried out in a two liter polypropylene reaction vessel, using a solution of 85 percent TFA, 5 percent phenol, 4 percent thioanisole, 4 percent deionized $H_2O$ and 2 percent ethanedithiol. The resins are shaken for 3.5 hours at room temperature. The reaction solution is removed, and the packets containing the completely deprotected solid support-coupled oligopeptide mixtures are quickly washed with chilled ether. The ether wash is repeated nine times (one minute each) followed by ten alternating washes of isopropanol and DCM. Finally, the solid support-coupled oligopeptide mixtures are washed five times with DMF, then twice more with DCM. Deprotected solid support-coupled oligopeptide mixtures and their enclosing packets are dried under reduced pressure. After this process is completed, the unprotected peptides are ready to be cleaved by anhydrous HF.

Where an N-acyl group such as an acetyl group is to be present on an oligopeptide mixture set, the final t-BOC or Fmoc protecting group is removed as above, an excess of acetic anhydride is added and the reaction is maintained until there are no more free amino groups present as discussed elsewhere herein. The above rinsing and drying steps are then carried out, followed by deprotection and cleavage of the oligopeptide mixture set from the solid support.

As noted earlier for post cleavage peralkylations, use of a benzhydrylamine resin as a solid support and anhydrous HF/anisole for cleavage of the oligopeptide mixture set provides a C-terminal amido group for the oligopeptide mixture set produced. Use of an ester-linked resin solid support and that cleavage procedure provides a C-terminal carboxylic acid. Use of a disulfide-containing linking group between the solid support and oligopeptide chains as discussed in U.S. Pat. No. 4,031,211 and cleavage with a disulfide bond breaking agent as discussed provides a C-terminal mercaptan linking group amide-bonded to the oligopeptide chains. Subsequent peralkylation provides dialkylamido, alkyl ester and alkyl thioether C-terminal groups.

In an exemplary preferred peralkylation, more than one peptide-coupled solid support (resin) is permethylated at one time by enclosing each peptide-coupled resin in separate polypropylene mesh packets. The amounts of various reagents and solvent are used based upon the total amount of active hydrogen present. An exemplary synthesis for a single peralkylated peptide is discussed below.

This synthesis is for the permethylated peptide PerA-AGGFL, whose N-terminal α-amine became a quaternary trimethylammonium group and whose C-terminal carboxyl became an N-methyl-carboxamide. Thus, 0.60 g of 60 percent NaH/oil [about 25 milliequivalents (meq)] were added to 100 ml of DMSO in a 250 ml polypropylene bottle with a ventilated screw cap to provide a final concentration of 0.25M of NaH. After shaking for about 30 minutes for the NaH to dissolve, 500 mg of the precursor peptide-coupled resin (about 2.5 meq of active hydrogen) within a polypropylene mesh packet were added to the bottle.

The bottle and its contents were shaken on a reciprocal shaker for 14 hours. At that time, 4.66 ml of $CH_3I$ (about 30 meq) were added directly to the bottle and its reaction mixture. The resulting reaction mixture was shaken for another 15 minutes.

The solution was poured off, and the packet and its contents were washed with aliquots of 100 ml of each of DMSO, DMF, isopropanol, twice with dichloromethane and then methanol. The thus peralkylated resin-coupled peptide was then dried under high vacuum and the peralkylated peptide cleaved using the standard high HF procedure discussed before.

Results for a similar peralkylation of this peptide-coupled resin are discussed in Example 4 along with results for nineteen similar peralkylations.

EXAMPLE 2

Chemical Mixture Synthesis

These syntheses using 18 of the 20 naturally occurring amino acid derivatives (Cys and Trp omitted) are carried out substantially as described in U.S. Pat. No. 4,631,211 and Example 1.

A cross-linked polystyrene resin is used as solid support that also included 0.93 milliequivalents (meq) of benzhydrylamine groups per gram. The solid support resin is typically utilized in an amount of 300 milligrams (mg) so that 2.79 meq of resin-amine are initially provided in each reaction.

The mixture of amino acid derivatives noted in Table 2, below, at 0.5M in 4 ml of dimethylformamide (DMF) is used for each coupling, as about a 7-fold molar excess over the amount of amine present, as resin-amine or after deprotection to provide N-terminal amine (free amine) groups. One equivalent of DIPCDI as coupling agent and one equivalent of N-hydroxylbenztriazole-$H_2O$ are used per equivalent of mixed amino acid derivative, so both are also present in about a 7-fold excess over the free amine groups present.

TABLE 2[1]

| Amino Acid | Weight[2] |
|---|---|
| Ala | 19 mg |
| Asp(Bn) | 33 mg |
| Glu(Bn) | 36 mg |
| Phe | 20 mg |
| Gly | 15 mg |
| His(DNP) | 50 mg |
| Ile | 123 mg |
| Lys(Cl—CBZ) | 76 mg |
| Leu | 36 mg |
| Met | 18 mg |
| Asn | 37 mg |
| Pro | 27 mg |
| Gln | 39 mg |
| Arg(Tsl) | 82 mg |
| Ser(Bn) | 24 mg |
| Thr(Bn) | 44 mg |
| Val | 72 mg |
| Tyr(Br—CBZ) | 60 mg |

[1]Parenthesized designations in the left column are used by each unless another parenthesized protecting group is shown. Bn = benzyl; DNP = dinitrophenyl; Tsl = toluenesulfonyl; CBZ = benzyloxy carbonyl; Cl—CBZ = o-chlorobenzyloxy carbonyl; Br—CBZ = o-bromobenzyloxy carbonyl.
[2]Milligrams (mg) of each protected amino acid derivative present in a chemical mixture per 1 milliequivalent of resin —$NH_2$ group. Diisopropyl-carbodiimide (DIPCD) used as coupling agent.

Each coupling is carried out at room temperature until there is no remaining free amine groups as in Example 1; about one hour. Deprotection and neutralizations are also carried out as in Example 1.

Each position of the precursor oligopeptide containing equimolar amounts of amino acid residues is added as described above. Using a 6-mer whose fifth position is occupied by one of eighteen predetermined amino acid side chains as exemplary, the above coupling provides a support-coupled one-mer peptide product of the formula X—B.

That support-coupled product is then divided into at least 18 aliquots of equal weight, small portions of the preparation often being retained for analytical purposes. Those aliquots are enclosed in labeled porous packets, as discussed in Example 1, and the 18 individual amino acid derivatives are reacted separately with those aliquots after deprotection and neutralization to form 18 support-coupled products of the formula $O_5$X—B.

Those 18 labeled porous packets containing the $O_5$X—B support-coupled product are then deprotected and neutralized together, and those products are together reacted again as discussed before with the mixed amino acid derivatives, while being maintained in their packets, to form 18 sets of support-coupled products of the formula $XO_5$X—B. This procedure is repeated three more times to form the 18 support-coupled 6-mer sets whose fifth position from the N-terminus is occupied by each of the 18 different predetermined amino acid residues and whose other positions are occupied by equimolar amounts of the 18 amino acid residues present in the reaction mixtures.

Where N-terminal acetyl groups are to be used, the N-terminal t-BOC groups are removed, the resulting free amines neutralized and the support-coupled 6-mers are reacted with acetic anhydride to form N-acetyl (Ac) groups. The N-acetyl coupled peptides are then peralkylated and cleaved from the solid support to form a plurality (18) of peralkylated 6-mer oligopeptide sets.

The above procedures are similarly used, as appropriate, to prepare the remaining five libraries of 18 sets (another 90 sets) having one of eighteen predetermined peralkylated amino acid residues at predetermined positions 1–4 and 6, and mixtures of equal molar amounts of the 18 peralkylated amino acid residues at the other peralkylated oligopeptide chain positions.

The relative equimolarity of coupling using the above procedure as compared to the physical mixture methods in precursor oligopeptide sets was determined by amino acid analysis of support-coupled products from a single coupling reaction. A commercial amino acid analyzer was utilized for these assays. The specific manipulations utilized are discussed hereinafter.

As is well known, even commercially available amino acid analyzers do not provide precise determinations because of several factors including decomposition of the amino acids, and the various reactions and responses the machines must carry out and make. On the other hand, the physical mixture method provides equimolar mixtures to a precision that is much greater than that obtained by the machine alone.

Thus, a physical mixture process solid support-coupled product (X—B) of one coupling reaction was prepared as in Example 1, deprotected, cleaved from the solid support resin and collected. A similar X—B solid support-coupled product was prepared by the chemical mixture method of this example. That X—B product was similarly deprotected, cleaved from the solid support resin and collected. Those samples were then sent amino acid analysis.

More specifically, after each of the above t-BOC, side chain-protected mixtures was prepared, the t-BOC groups were removed, and the side chains deprotected. Each of the two mixed amino acid-coupled solid supports (X—B) was dried, and 20 mg of each resin-linked product was placed into 5 ml glass ampules. One milliliter of propionic acid:HCl (50:50, V/V) was added to each ampule. Air was removed from the ampules with a vacuum pump with care being taken not to aspirate the contents of the ampules. Each ampule was then sealed using a propane flame, while under vacuum. The sealed ampules were placed in a dry block heater and maintained at 130° C. for two hours to cleave the reacted amino acids from the solid support resin and form hydrolyzate solutions.

Thereafter, upon cooling to room temperature, the ampules were broken open and their contents filtered into separate 12–75 mm culture tubes. Aliquots (20 μl) of the hydrolyzate solution were placed into 5–50 mm culture tubes in duplicate. Those samples were coded, dried and sealed.

The sealed, coded samples were sent to Core Laboratories, New Orleans, La. for amino acid analysis. The results of that analysis are shown below, for each sample. In addition, because it is known that the physical mixture method provides more precise results than does amino acid analysis, the percentage of deviation from equimolarity for the chemical mixture method was determined by presuming that the value obtained for the individual amino acid residues obtained from the physical mixture method was the correct value of one-eighteenth mole percent (5.56 percent). It is noted that Glu and Gln analyze together as do Asp and Asn because the resin-cleaving step also destroys the Gln and Asn amide bonds, forming Glu and Asp, respectively.

| Amino Acid | Mole Percent | | Deviation from Equimolarity (Percent) |
|---|---|---|---|
| | Physical Mixture | Chemical Mixture | |
| Asp,Asn | 13.84 | 16.73 | +21 |
| Glu,Gln | 10.87 | 11.99 | +10 |
| Ser | 4.11 | 4.14 | −1 |
| Gly | 5.13 | 5.04 | −2 |
| His | 4.84 | 3.16 | −35 |
| Arg | 6.57 | 5.03 | −23 |
| Thr | 5.48 | 6.10 | +11 |
| Ala | 6.36 | 6.48 | +2 |
| Pro | 7.22 | 7.28 | +1 |
| Tyr | 4.31 | 3.53 | −18 |
| Val | 6.08 | 6.76 | +11 |
| Met | 3.38 | 4.13 | +22 |
| Ile | 5.08 | 4.07 | −20 |
| Leu | 6.58 | 5.95 | −10 |
| Phe | 5.17 | 3.78 | −27 |
| Lys | 4.96 | 5.85 | +18 |

EXAMPLE 3

Synthesis of Peptide Mixtures on Cotton Carriers

Twenty discs cut out of commercially available cotton fabric (diameter 4.7 cm) are shaken for 15 minutes in 50 ml of dichloromethane (DCM) containing 25 percent trifluoroacetic acid (TFA). The discs are then taken out and placed into a flat ceramic funnel with the same diameter as the cotton discs. The funnel is placed on top of an 1000 ml suction flask with an outlet to a vacuum pump. The 25 percent TFA/DCM is removed from the cotton discs into the suction flask under reduced pressure. The cotton discs are then washed with DCM (2×10 ml), DCM containing 5 percent DIEA (2×10 ml) and DCM (2×10 ml) again. The washings are done by adding the wash solution to the funnel holding the cotton discs and removal of the solvent with a vacuum pump. After the last wash the cotton discs are removed and air dried. All manipulations are at room temperature unless otherwise stated.

A. Manual Synthesis

Fmoc-Glycine (1.118 g, 4 mmol), N-hydroxybenztriazole (HOBt) (540 mg, 4 mmol), N-methylimidazole (NMI) (656 μl, 8 mmol) and DIPCDI (626 μ, 4 mmol) are dissolved in 6.7 ml DMF. This corresponds to a 0.5 M Fmoc-Gly/HOBt/DIPCDI, 1M NMI solution. The cotton discs are soaked with this solution in a 20 ml scintillation vial and maintained for three hours. After transferring the discs to the ceramic funnel, the cotton carriers are washed with DMF (3×10 ml) and DCM (2×10 ml) as described above. This procedure is repeated once more identically.

The general peptide mixture and single, predetermined peptide coupling procedure is as follows:

1. Fmoc-deprotection: 20 percent piperidine/DMF, 15 minutes.
2. Wash: 3×DMF, 3×DCM.
3. Coupling: 0.3M Fmoc-amino acid/HOBt/DIC in DMF, 90 minutes - two hours.
4. Wash: 3×DMF, 2×DCM.

More specifically, the twenty cotton discs, placed into the ceramic funnel, are soaked with 10 ml 20 percent piperidine/ DMF, and maintained for 15 minutes. After removing the 20 percent piperidine/DMF, the cotton discs are washed with DMF (3×10 ml) and DCM (2×10 ml) as described above.

(a) Coupling of the same amino acid to all cotton discs

The Fmoc-amino acid to be coupled (2.4 mmol), HOBt (324 mg, 2.4 mmol) and DIPCDI (380 μl, 2.4 mmol) are dissolved in 7.6 ml DMF. This corresponds to a 0.3 M Fmoc-amino acid/HOBt/DIC solution. The cotton discs are soaked with this solution in a 20 ml scintillation vial and maintained for 90 minutes. After transferring the discs to the ceramic funnel, the coupling solution is removed, and the cotton carriers are washed with DMF and DCM, as before.

(b) Coupling of another amino acid to each cotton disc (O-coupling)

The 20 natural amino acids (0.12 mmol each) are separately dissolved in 0.4 ml of a 0.3M solution of HOBt and DIPCDI in DMF (324 mg HOBt and 380 μl DIPCDI dissolved in 7.6 ml DMF). The cotton discs are labeled as to amino acid identify with the letters A through Y, soaked with the amino acid solution, labeled with the letter of the amino acid of the solution, and maintained for 90 minutes. After transferring the discs to the ceramic funnel, the cotton discs are washed with DMF and DCM, as before.

(c) Coupling of the amino acid mixture (X-coupling)

A 0.3M solution of the 20 natural amino acids except Cys in the molar ratio of Table 2 and HOBt in DMF is prepared and aliquoted. The aliquots (7.6 ml each) are stored at −20° C. Before the coupling, the mixture aliquot is warmed up to room temperature, followed by addition of 380 μl DIPCDI. After 20 minutes (preactivation), the 19 cotton discs are soaked with this solution and maintained for two hours. After transferring them to the ceramic funnel, the cotton discs are washed with DMF and DCM, as before.

After coupling of the last (N-terminal) amino acid or mixture, the cotton discs are Fmoc-deprotected and washed. The deprotected cotton discs are soaked with 8 ml of a mixture of acetic anhydride/pyridine/DMF 1:2:3 (v/v/v) and maintained for 60 minutes. After transferring them to the ceramic funnel, the cotton discs are washed with DMF and DCM.

The acetylated cotton discs are placed into a bottle containing 30 ml 50 percent TFA, 5 percent triisobutylsilane in DCM and maintained for two hours. After pouring off the solution, 100 ml DCM are added and the bottle shaken for two minutes. This wash is repeated twice with DCM, then three times with 5 percent DIEA/DCM and again three times with DCM. The cotton discs are taken out, blotted between layers of filter paper and air dried. The dry cotton discs are cut into small discs (diameter 7 mm) with an ordinary hole puncher, labeled and refrigerated.

Peralkylation is then carried out as discussed before.

B. Machine Synthesis

The synthesis is done as described in allowed U.S. Pat. No. 5,202,418 to Lebl et al., whose disclosures are incorporated by reference, and above. The essential difference between the manual synthesis of peptide mixtures and the synthesis of individual peptides on the synthesizer machine is the following: The manually prepared mixtures are synthesized directly on the glycine-cotton. Upon alkaline hydrolysis of the glycine-cotton ester, the cotton-cleaved peptides therefore contain an additional C-terminal Gly residue. In case of the synthesis of individual peptides on the machine synthesizer, a TFA-cleavable linker, in this case N-f-Moc-2,4-dimethoxy-4'-(carboxymethyloxy)-benzhydrylamine for the synthesis of peptide amides, is coupled onto the amino group of the glycine-cotton ester. After Fmoc-deprotection of the linker, the first amino acid of the peptide is coupled to the amino group of the linker. Upon cleavage of the peptides with TFA, simultaneously with the deprotection of side chains, the set of oligopeptide amides is formed, with the linker and the glycine remaining bound to the cotton. Peralkylation of the cleaved sets is then carried out. Peralkylation can also be carried out while the precursor peptide is bound to the solid support.

EXAMPLE 4

Pentamer Permethylation

Twenty model pentameric solid support-bound oligopeptides were prepared as described in U.S. Pat. No. 4,631,211. The C-terminal four positions were identical for each, with the N-terminal residue being varied among the twenty naturally occurring amino acid residues. The support-bound precursor pentamers were peralkylated as discussed before.

Briefly, the support-bound pentamers (50 mg each), each in their own polypropylene mesh containers, were shaken for 16 hours at room temperature in a DMSO solution of 0.25 molar sodium hydride (24 ml, 8 meq.). Methyl iodide (neat 1.1 ml, 24 meq.)was then added to the solution at an 4-fold excess over the moles of base. The peralkylation reaction was permitted to continue for 15 minutes or until the reaction mixture came to room temperature. Following washes with DMF (3×5 ml), isopropanol (IPA; 2×5 ml), DCM (3×5 ml) and methanol (1×5 ml), the peralkylated support-bound peptides were dried under high vacuum. The peralkylated oligopeptides were cleaved from the support resin using 7.5 percent anisole in HF (5 ml) for one and one-half hours at zero degrees C, dried under a high vacuum, extracted with 10 ml of water and lyophilized. Use of 10 volume percent acetic acid in water for the extraction provides an enhanced result with more hydrophobic alkyl groups.

The individual peralkylated oligopeptides were recovered and subjected to reversed phase high performance liquid chromatograph (RP-HPLC) and identified by laser-desorption mass spectral analysis (Kratos). Analytical RP-HPLC was performed on a Bydac $C_{18}$ column (Hesperia, Calif.) using a Beekman System Gold™ HPLC system monitored at 215 nm; Solvents A, 0.05 percent TFA/$H_2O$; Solvent B, 0.05 percent TFA/$CH_3CN$; gradient, 5–65 percent B. Preparative RP-HPLC was performed on a Waters $C_{18}$ column (5 cm×25 cm) on a Waters Delta Prep™ HPLC System monitored at 215 nm; Solvents A and B as above. The results of those analyses are shown in Table 3, below, using single letter code of unalkylated amino acids for the peralkylated (permethylated) residue.

TABLE 3

Model Peptide Side Chain Modifications

| Peralkylated Sequence[1] | Post Methylation Molecular Weight | Added Number of Methyls | HPLC Purity (Percent)[3] |
|---|---|---|---|
| PerA-AGGFL (SEQ ID NO: 1) | 575.3 | 8 | 91 |
| PerA-CGGFL (SEQ ID NO: 2) | 620.8 | 9 | 50 |
| PerA-DGGFL (SEQ ID NO: 3) | 633.6 | 9 | 60 |
| PerA-EGGFL (SEQ ID NO: 4) | 647.8 | 9 | 75 |
| PerA-FGGFL (SEQ ID NO: 5) | 650.9 | 8 | 91 |
| PerA-GGGFL (SEQ ID NO: 6) | 661.0 | 8 | 92 |
| PerA-HGGFL (SEQ ID NO: 7) | 655.8 | 9 | 40 |
| PerA-IGGFL (SEQ ID NO: 8) | 617.2 | 8 | 90 |
| PerA-KGGFL (SEQ ID NO: 9) | 673.0 | 11 | 30 |
| PerA-LGGFL (SEQ ID NO: 10) | 617.2 | 8 | 81 |
| PerA-MGGFL[2] (SEQ ID NO: 11) | 651.8 | 8 | 70 |
| PerA-NGGFL (SEQ ID NO: 12) | 649.9 | 10 | 86 |
| PerA-PGGFL (SEQ ID NO: 13) | 588.0 | 7 | 90 |
| PerA-QGGFL (SEQ ID NO: 14) | 660.0 | 10 | 80 |
| PerA-RGGFL (SEQ ID NO: 15) | 547.8 | 11 | 75 |
| PerA-SGGFL (SEQ ID NO: 16) | 591.7 | 8 | 95 |
| PerA-TGGFL (SEQ ID NO: 17) | 604.9 | 8 | 95 |
| PerA-VGGFL (SEQ ID NO: 18) | 603.2 | 8 | 95 |
| PerA-WGGFL (SEQ ID NO: 19) | 704.8 | 9 | 70 |
| PerA-YGGFL (SEQ ID NO: 20) | 681.5 | 9 | 81 |

[1]Each peralkylated oligopeptide contained a trimethylammonium N-terminal nitrogen atom, a methyl group on each amido nitrogen of the backbone, appropriately methylated side chains and a C-terminal N-methylcarboxamide group that are not shown in the peralkylated sequences above.
[2]The methionine was present as methionine sulfoxide.
[3]Purities of the crude compounds were determined by analytical RP-HPLC.

EXAMPLE 5

Binding to Opioid Receptors

The enkephalins were the first natural ligands found for the opioid receptors. These molecules bind to three known receptor subclasses (mu, delta and kappa) with differing affinities [reviewed in Schiller, *Progress in Medicinal Chemistry*, Ellis et al. eds., Elsevier Science Publishers, U.K. (1990) pages 301–340]. The competitive binding studies herein utilized a radiolabeled analog of met-enkephalin, [$^3$H] -[D-Ala$^2$,MePhe$^4$,Gly-Ol$^5$]enkephalin (DAGO) that is known to bind specifically to the mu receptor in competitive binding studies with positional libraries of peralkylated hexamer sets; i.e., peralkylated 5×sets.

Two libraries of libraries of sets were used for these assays. The first contained an N-terminal pyroglutamoyl group (from pyrrolidone carboxylic acid), and the second library contained an a-quaternary trimethylammonium group. Both libraries were permethylated and contained each of the 20 natural amino acids with Met present as the sulfoxide and N-methyl caboxamido C-termini. These libraries were prepared as discussed in Example 1 and were permethylated as discussed before.

A. N-Pyroglutamoyl-Terminated Libraries

Scanning the first or N-terminal position (the 1-position) showed that permethylated Asp, Glu, Gly, Lys, Met, Asn, Pro, Gln, Ser, Thr and Val provided the greatest inhibition, between 50 and 60 percents, with permethylated Thr and Glu providing the greatest inhibition.

Scanning the 2-position showed that permethylated Asp, Glu, Gly, Ile, Asn, Pro, Gln and Thr provided the greatest inhibition, between 50 and 60 percents, with permethylated Asn being best.

Scanning the 3-position showed that only permethylated Glu provided an inhibition greater than 60 percent, with nine other residues permethylated Ala, Asp, Gly, Met, Asn, Pro, Gln, Ser and Thr providing inhibitions between 50 and 60 percents.

The 4-position scan showed that permethylated Asp, Glu and Met provided about 60 percent binding inhibition and eight more permethylated residues exhibition inhibitions between 50 and 60 percents; i.e., Ala, Gly, Asn, Pro, Gln, Ser, Thr and Val.

The 5-position scan showed permethylated Glu to provide an inhibition of more than 60 percent, with permethylated Met, Ser and Thr exhibiting an almost 60 percent inhibition.

Scanning of the 6-position, the C-terminus, showed that permethylated Glu provided almost 100 percent inhibition of binding, with no other permethylated residue providing more than 70 percent inhibition.

Permethylated His exhibited an inhibition of 20 percent or less at each position. Permethylated Trp, Phe and Arg were also uniformly poor inhibitors at each scanned position.

The enkephalins and DAGO both contain two aromatic residues. The above results thus indicate that peralkylated aromatic residues are not important to binding here, thus opening the way to new relatively hydrolytically stable enkephalin inhibitors.

B. Trimethylammonium-Terminated Libraries

The same precursor support-coupled peptides used in A, above, but lacking the N-pyroglutamoyl group were permethylated as discussed before and cleaved from the resin support to provide six libraries of 20 library sets of 5×oligopeptides. The N-terminal residues here had α-trimethylammonium groups.

Scanning of the 1-position showed that only permethylated Glu exhibited a binding inhibition of greater than 40 percent. Permethylated Met, Pro, Gln and Ser exhibited inhibitions of between 30 and 40 percent.

Scanning the 2-position again showed permethylated Glu to be alone at more than 40 percent inhibition. Permethylated Asp, Gly, Met, Asn, Pro, Gln and Thr exhibited inhibitions of between about 30 and 40 percents.

Position 3 again showed permethylated Glu to provide the best inhibition at between about 30 and 35 percents, with permethylated Met and Gln also exhibiting greater than about 30 percent inhibition.

Permethylated Met provided the best inhibition at position 4, followed by permethylated Asn, Glu, Gln and Gly. Each inhibition was about 30 percent or greater, but less than 40 percent.

The scan of the 5-position showed that only permethylated Gln exhibited inhibition greater than 40 percent. Permethylated Ala, Asp, Met, Asn, Ser and Thr exhibited inhibitions between 30 and 40 percent.

The scan of the 6-position showed permethylated Gly, Met and Thr to exhibit inhibitions of between about 40 percent and about 50 percent.

Permethylated His, the aromatics, Cys, Arg and Lys all exhibited poor binding inhibition at each position in these assays.

Binding inhibitions exhibited by these libraries were generally lower than those illustrated before. These libraries exhibited somewhat greater differences in binding inhibitions.

The above assays were carried out using opioid receptors from rat brains prepared as follows. Particulate membranes were prepared using a modification of the method described by Pasternak et al., *Mol. Pharm.*, 11:340–351 (1975). Rat brains frozen in liquid nitrogen were obtained from Rockland Inc. (Gilbertsville, Pa.). The brains were thawed, the cerebella were removed, and the remaining tissue was weighed. Each brain was individually homogenized in 40ml Tris-HCl buffer (50mM, pH 7.4, 4° C.) and centrifuged (Sorvall RC5C SA-600 16000 rpm) for ten minutes. The pellets were resuspended in fresh Tris-HCl Buffer and incubated at 37° C. for 40 minutes. Following incubation, the suspensions were centrifuged as before, the resulting pellets were resuspended in 100 volumes of Tris buffer, and the suspensions combined. Membrane suspensions were prepared and used in the same day. Protein content of the crude homogenates ranged from 0.15–0.2 mg/ml as determined using the method described by Bradford, *Anal. Biochem.*, 72:248–254 (1976).

Binding assays were carried out in polypropylene tubes. Each tube contained 0.5 ml of membrane suspension, 8 nM of [$^3$H]-[D-Ala$^2$,MePhe$^4$,Gly-Ol$^5$]enkephalin (DAGO) (specific activity=36 Ci/mmole, 160,000 cpm/tube; obtained from Multiple Peptide Systems, Inc., San Diego, Calif. through NIDA drug distribution program 271-90-7302), and 2 mg/ml of permethylated peptide mixture and Tris-HCl buffer in a total volume of 0.65 ml. Assay tubes were incubated for 60 minutes at 25° C. The reaction was terminated by filtration through GF-B filters on a Tomtec harvester (Orange, Conn.). The filters were subsequently washed with 6 ml of Tris-HCl buffer, 4° C. Bound radioactivity was counted on an LKB Beta-plate Liquid Scintillation Counter and expressed in counts per minute (cpm). To determine inter- and intra-assay variation, standard curves in which [$^3$H]-DAGO was incubated in the presence of a range of concentrations of unlabeled DAGO (0.13–3900 nM) were included in each plate of each assay (a 96-well format was used).

EXAMPLE 6

Antimicrobial Activity Against *S. aureus*

The two types of libraries of positional libraries of Example 5 were also scanned against *Staphylococcus aureus* a Gram-positive bacterium. Concentrations of those 5×permethylated peptide mixtures that inhibited cellular growth by 50 percent (IC$_{50}$) values were determined.

Residues of each library type and set member are provided below whose IC$_{50}$ values were within a factor of about two of the most potent residues. IC$_{50}$ values are in mg/ml.

| A. N-Pyroglutamoyl-Terminated Libraries[1] | | | |
|---|---|---|---|
| Position 1 | | Position 2 | |
| Residue | Average IC$_{50}$ | Residue | Average IC$_{50}$ |
| Tyr | 500.57 | Tyr | 597.67 |
| Trp | 792.61 | Ile | 781.86 |
| Ile | 871.18 | Trp | 995.69 |
|  |  | Leu | 1031.02 |
| Position 3 | | Position 4 | |
| Residue | Average IC$_{50}$ | Residue | Average IC$_{50}$ |
| His | 394.85 | His | 321.62[2] |
| Tyr | 519.62 | Tyr | 538.86 |
| Trp | 639.02 | Leu | 640.90 |
| Val | 797.33 |  |  |
| Position 5 | | Position 6 | |
| Residue | Average IC$_{50}$ | Residue | Average IC$_{50}$ |
| His | 217.222 | His | 152.41[2] |

[1] Starting concentrations of 2500 μg/ml of permethylated sets were used. Each IC$_{50}$ value is an average of two assay results.
[2] Only one assay was conducted.

The above results indicate that the permethylated aromatic residues Tyr and Trp that were unimportant in the assays of Example 5 are quite important near the N-terminus in these assays. Similarly, His, which was always the worst residue in inhibiting binding in Example 5 is important near or at the C-terminus. Similarly, permethylated Asp, Glu, Asn, Gin, Ser, Thr and Gly that were important in the assays of Example 5 typically provided the highest $IC_{50}$ values.

B. N-Trimethylammonium-Terminated Libraries[1]

| Position 1 | | Position 2 | |
|---|---|---|---|
| Residue | Average $IC_{50}$ | Residue | Average $IC_{50}$ |
| Tyr | 94.41 | Phe | 93.96 |
| Trp | 103.35 | Tyr | 131.54 |
| Phe | 115.49 | Ile | 141.56 |
| Ile | 138.92 | Trp | 167.46 |
| His | 157.67 | His | 192.85 |
| Leu | 188.85 | | |

| Position 3 | | Position 4 | |
|---|---|---|---|
| Residue | Average $IC_{50}$ | Residue | Average $IC_{50}$ |
| Phe | 89.93 | Trp | 93.29 |
| Ile | 93.01 | Phe | 93.50 |
| Trp | 100.14 | Ile | 108.05 |
| Leu | 135.07 | His | 121.91 |
| Tyr | 136.15 | Tyr | 161.67 |
| Cys | 146.89 | Leu | 183.48 |
| Val | 187.18 | | |

| Position 5 | | Position 6 | |
|---|---|---|---|
| Residue | Average $IC_{50}$ | Residue | Average $IC_{50}$ |
| Phe | 95.72 | His | 91.37 |
| His | 101.57 | Phe | 93.77 |
| Trp | 121.21 | Trp | 93.78 |
| Ile | 126.18 | Tyr | 145.18 |
| Tyr | 156.50 | Ile | 154.41 |
| Leu | 171.34 | | |

| Positive Controls | |
|---|---|
| Drug | Average $IC_{50}$ |
| Oxacillin | 0.106 |
| Erythromycin | 0.184 |

[1]Starting concentrations of 2500 µg/ml for the less active permethylated sets were used, with starting concentrations of 1250 µg/ml for the more active sets. $IC_{50}$ Values are an average of two assay results.

The most active of these latter, N-trimethylammonium-terminated, sets were about two- to about five-fold more active than the prior sets in inhibiting growth of this bacterium. These latter sets also showed an importance of permethylated aromatic residues, particularly phenylalanine (Phe), near the N-terminus that continued through each position. Histidine was also important near the C-terminus of these sets, but in a less clear-cut way than noted in the first sets assayed. The same residues found important in Example 5 but unimportant against *S. aureus* in the first assays of this example were also found unimportant here. Methionine sulfoxide that was also important in Example 5 was relatively unimportant here.

EXAMPLE 7

Permethylated Oligo-Phe Peptides

In view of the apparent importance of permethylated Phe residues at each position in the scans of Example 6, a series of permethylated homoPhe C-terminal N-methylamide peptides was prepared, as was permethylated Phe N-methylamide itself. Each permethylated peptide and the permethylated amino acid contained an N-terminal trimethylammonium group and a C-terminal N-methylamide group.

It was thought that the observed preference for peralkylated Phe residues may have been due to a real preference for one or two such residues that was evidenced as a frame shift in the positional scans. Thus, an individual peralkylated amino acid and individual peralkylated peptides, rather than sets or libraries of sets were prepared and assayed as illustrative and to examine the possibility of the results being due to a frame shift.

The permethylated amino acid and peptides were screened against *S. aureus* and *Streptoccus sanguis*, as described below, and $IC_{50}$ and MIC (minimum inhibitory concentration; minimum concentration needed to inhibit about 100 percent bacterial growth) values were determined. Average results from those studies are shown below in Tables 4 and 5, along with results for the antibiotics oxacillin and erythromycin and N-acetyl hexaPhe amide (N-Ac-hexaPhe) as controls in the *S. aureus* study.

TABLE 4

Assays Against *S. aureus*

| Peralkylated Sequence[1] | | $IC_{50}$ Value (µM) | MIC Value (µM) |
|---|---|---|---|
| PerA-F | | >500 | >500 |
| PerA-FF | | >500 | >500 |
| PerA-FFF | | 288 | >500 |
| PerA-FFFF | SEQ ID NO: 21 | 116 | 250–500 |
| PerA-FFFFF | SEQ ID NO: 22 | 19 | 21–31 |
| PerA-FFFFFF | SEQ ID NO: 23 | 7 | 11–15 |
| PerA-FFFFFFF | SEQ ID NO: 24 | 2.5 | 3–4 |
| PerA-FFFFFFFF | SEQ ID NO: 25 | 5 | 6–8 |
| Controls | | | |
| N—Ac-hexaPhe | | >500 | >500 |
| Oxacillin | | 0.042 | 0.125 |
| Erythromycin | | 0.184 | 0.5 |

[1]Each peralkylated oligopeptide contained a trimethylammonium N-terminal nitrogen atom, a methyl group on each amido nitrogen of the backbone, appropriately methylated side chains and a C-terminal N-methylcarboxamide group that are not shown in the peralkylated sequences above.

TABLE 5

Assays Against *S. sanguis*

| Peralkylated Sequence[1] | | $IC_{50}$ Value (µM) | MIC Value (µM) |
|---|---|---|---|
| PerA-F | | >500 | >500 |
| PerA-FF | | >500 | >500 |
| PerA-FFF | | 446 | >500 |
| PerA-FFFF | SEQ ID NO: 21 | 85 | 125–250 |
| PerA-FFFFF | SEQ ID NO: 22 | 20 | 25–30 |
| PerA-FFFFFF | SEQ ID NO: 23 | 5 | 7–8 |
| PerA-FFFFFFF | SEQ ID NO: 24 | 2.3 | 3–4 |
| PerA-FFFFFFFF | SEQ ID NO: 25 | 7 | 8–9 |

[1]Each peralkylated oligopeptide contained a trimethylammonium N-terminal nitrogen atom, a methyl group on each amido nitrogen of the backbone, appropriately methylated side chains and a C-terminal N-methylcarboxamide group that are not shown in the peralkylated sequences above.

As can be seen from the above data, the positional scanning process provided a basis for obtaining a permethylated oligopeptide whose potency was less, but similar to those of recognized antibiotics. The above results also indicate that the scanning results were correct and not due to a frame shift. These results were obtained using an unoptomized sequence in that Phe was not the optimal residue at each position in the positional scans of Example 6, but was near optimal and use of a homoPhe permethylated heptapeptide was convenient for illustration. Even though the homoPhe permethylated heptapeptide was used illustratively, the potency of the permethylated peptide was shown to increase as each residue was added, with an overall potency increase of over 2 orders of magnitude being shown.

Staphylococcus aureus (ATCC 29213) were grown overnight (about 18 hours) at 37° C. in cation-adjusted Mueller-Hinton (CAMH) broth. This culture was reinoculated and incubated at 37° C. to reach the exponential phase of bacterial growth; i.e., a final bacterial suspension containing about $10^5$ to $5\times10^5$ colony-forming units (CFU)/ml. The concentration of cells was established by plating 100 µl of different dilutions of the culture solution (e.g., $10^{-2}$, $10^{-3}$ and $10^{-4}$) onto solid agar plates. Following an overnight (about 18 hours) incubation at 37° C., the CFU thus formed were counted on each agar plate.

96-Well tissue culture plates were utilized, with eight wells per plate containing only medium as control blanks, whereas eight other wells contained medium plus cells as a positive growth control. These controls were used to detect possible medium contamination and to provide a measure of uninhibited growth of the microorganisms.

For determination of $IC_{50}$ values (concentrations necessary to inhibit 50 percent growth of bacteria), peralkylated oligopeptide sets were added to the bacterial suspension at concentrations noted before. The plates were incubated overnight (about 18 hours) at 37° C., and the optical density (OD) determined at 620 nm after different times of incubation. $IC_{50}$ Values were then determined from the OD data.

EXAMPLE 8

Single Permethylated Oligopeptides

Based on the results shown in Example 6 against S. aureus using the 120 scanning N-trimethylammonium-terminated permethylated C-terminal methylamido oligopeptide sets, individual peptides were synthesized representing all combinations of the six amino acids chosen for the first position (Trp, Phe, Tyr, His, Ile and Leu); Phe for the second position; Trp, Ile and Phe for the third position; Trp and Phe for the fourth position; and Phe and His for both the fifth and sixth positions. Following their synthesis, the resultant 144 individual, permethylated peptides (6×1×3×2×2×2) were assayed for their antimicrobial activity. Of the 144 peptides prepared, 41 had $IC_{50's}<50$ µg/ml, while 51 had $IC_{50's}\geq 250$ µg/ml against S. aureus. Table 6 lists the 10 most active sequences and data from their use.

The permethylated forms of FFIFFF-NH$_2$, FFFFFF-NH$_2$ and LFIFFF-NH$_2$ (SEQ ID NO's:27, 23 and 26) were found to exhibit the greatest activity of the series, with each having an MIC lower than 15 µg/ml. The permethylated hepta- and octa-Phe peptides (SEQ ID NO's:24 and 25) of Example 7 exhibited similar activities against MRSA. In contrast, the quaternary ammonium salt of non-permethylated FFFFFF-NH$_2$ (SEQ ID NO:35) showed no activity ($IC_{50}$>250 µg/ml). Similar activities were found against MRSA and S. Sanquis (Table 6), whereas none of the permethylated peptides or peptide mixtures exhibited activity against E. coli or C. albicans ($IC_{50's}$>600 µg/ml). Also, none of the mixtures, nor any of the individual permethylated peptides, had significant toxicity as evidence by lysis of human red blood cells (RBC's) (Table 6). The activity of these new compounds therefore appears to be highly specific for Gram-positive bacteria.

These compounds showed activities similar to a range of previously described peptides made up of L-amino acids [Houghten et al., Nature, 354:84-86 (1991); Houghten et al., Biotechniques, 13:412-421 (1992); and Houghten et al., in Innovation and Perspectives in Solid Phase Synthesis, Epton ed., Solid Phase Conference Coordination, Andover, UK (1992), pp. 237-239], and, in contrast to these L-amino acid peptides, they appear to be completely stable to proteolytic enzymes (as indicated hereinafter). The physical-chemical properties of these compounds (enhanced resistance to proteolytic enzymes, excellent water solubility, favorable aqueous/organic partitioning characteristics) add value to their potential as therapeutic leads. Surprisingly, only a small number of the permethylated peptides having either Trp or Tyr in their sequences were found to be active. In experience with the L-amino acid library, it is consistently found that Trp- and Tyr-containing peptides to have antimicrobial activity, which has not been the case when the peptides are permethylated [Houghten et al., Nature, 354:84-86 (1991); Houghten et al., Biotechniues, 13:412-421 (1992); and Houghten et al., in Innovation and Perspectives in Solid Phase Synthesis, Epton ed., Solid Phase Conference Coordination, Andover, UK (1992), pp. 237-239]. This is being investigated separately using the same iterative approach that was used to identify the activity L-amino acid peptides.

Assays using S. aureus were carried out as described before. Methicillin-resistant Staphylococcus aureus (MRSA) ATCC 33591, Streptococcus sanquis ATCC 10566,

TABLE 6

Antimicrobial and Hemolytic Activities of Permethylated Peptides[1]

| µg/ml | Sequence[2] | S. aureus | | MRSA | | S. sanguis | | % hemolysis |
|---|---|---|---|---|---|---|---|---|
| | | $IC_{50}$ | MIC | $IC_{50}$ | MIC | $IC_{50}$ | MIC | at 350 |
| SEQ ID NO: 26 | PerM-LFIFFF | 6 | 11–15 | 7 | 8–10 | 1.7 | 3–5 | 12 |
| SEQ ID NO: 27 | PerM-FFIFFF | 6 | 11–15 | 7 | 8–10 | 14 | 20–40 | 0 |
| SEQ ID NO: 23 | PerM-FFFFFF | 7 | 11–15 | 7 | 8–10 | 9 | 15–20 | 16 |
| SEQ ID NO: 28 | PerM-LFFFFF | 10 | 21–31 | 8 | 9–10 | 14 | 20–40 | 10 |
| SEQ ID NO: 29 | PerM-FFFFHF | 11 | 15–21 | 18 | 21–42 | 19 | 30–40 | 3 |
| SEQ ID NO: 30 | PerM-LFIFFH | 12 | 21–31 | 20 | 25–42 | 19 | 30–40 | 1 |
| SEQ ID NO: 31 | PerM-LFFFHF | 12 | 21–31 | 13 | 15–21 | 19 | 30–40 | 4 |
| SEQ ID NO: 32 | PerM-LFIFHF | 12 | 21–31 | 14 | 15–21 | 13 | 20–40 | 7 |
| SEQ ID NO: 33 | PerM-LFFFFH | 13 | 21–42 | 16 | 21–42 | 22 | 30–40 | 3 |
| SEQ ID NO: 34 | PerM-FFIFFH | 14 | 31–42 | 19 | 21–42 | 18 | 30–40 | 0 |

[1] All numerical data are in µg/ml.
[2] Each peralkylated oligopeptide contained a trimethylammonium N-terminal nitrogen atom, a methyl group on each amido nitrogen of the backbone, appropriately methylated side chains and a C-terminal N-methylcarboxamide group that are not shown in the peralkylated sequences above.

*Escherichia coli* ATCC 25922 and *Candida albicans* ATCC 10231 were used in the bioassays (ATCC, Rockville, Md.). To initiate the exponential phase of bacterial growth prior to the assay, a sample of bacteria grown overnight (about 18 hours) at 37° C. in cation-adjusted Mueller Hinton broth (CAMH, for *E. coli* and *S. aureus*—Becton Dickinson Microbiology Systems, Cockeysville, Md.), or Brain Heart Infusion broth (BHI, for *S. sanguis*), was reinoculated in a 2×broth and incubated at 37° C. MRSA was grown at 35° C. in cation-adjusted MH broth in a similar manner. Prior to the assay, two colonies of newly grown *C. albicans* culture were inoculated in 5ml of phosphate buffer saline (PBS-35mM phosphate buffer, 0.15M NaCl-pH 7.0), and diluted in yeast medium broth. The bacteria and yeast suspensions were adjusted turbidimetrically so that a final concentration of $10^5$ to $5 \times 10^5$ colony-forming units (CFU)/ml was used in all assays.

The assays were carried out in 96-well tissue culture plates (Costar, Pleasanton, Calif.) as described in Blondelle et al., *Biochemistry*, 31:12688–12694 (1992), incorporated herein by reference. In brief, the bacterial suspension was added to an equal volume of the mixture of permeythylated compounds diluted in $H_2O$ at concentrations derived from serial two-fold dilutions varying from 2500 μg/ml to 1 μg/ml. The plates were then incubated overnight at 37° C. The relative percent growth found for each compound (or mixture of compounds) was then determined by the optical density at 620 nm ($OD_{620}$) using a Titertek Multiskan Plus apparatus (Flow Laboratories, McLean, Va.). The concentration necessary to inhibit 50 percent bacterial growth ($IC_{50}$) was then calculated using the software program GRAPHPAD (ISI, San Diego, Calif.). The minimum inhibitory concentrations (MIC's) were defined as the minimum concentration of peptide at which there was no change in $OD_{620}$ between time 0 and 21 hours. In a similar manner, the plates containing *C. albicans* suspension were incubated for 48 hours at 30° C.

Hemolytic activities of the peptides were determined using human red blood cells (RBC's). The assays were carried out in 96-well tissue culture plates against a 0.25 percent RBC suspension as described in Blondelle et al., *Biochim. Biophys. Acta*, 1202:331–336 (1993), incorporated herein by reference. Briefly, individual permethylated peptides or peptide mixtures were added to the RBC solution at concentrations derived from serial two-fold dilutions varying from 650 to 64 μg/ml. Following a one hour incubation at 37° C., the plates were centrifuged at 2800 rpm for 5 minutes. The supernatant was separated from the pellet and its OD measured at 414 nm. Triton (1 percent) and PBS were used as 100 percent and 0 percent hemolysis controls, respectively.

EXAMPLE 9

Racemization Study

From the literature, is was anticipated that the conditions used here for permethylation would result in minimal racemization or $C_\alpha$-methylation [Challis et al., *The Chemistry of Amides*, Zabicky ed., Interscience, New York (1970) pp. 731–857; Coggins et al., *Can J. Chem.*, 49:1968–1971 (1971)]. Because the increased acidity of the C-hydrogen of aromatic amino acids such as Phe [Challis et al., *The Chemistry of Amides*, Zabicky ed., Interscience, New York (1970) pp. 731–857; Coggins et al., *Can J. Chem.*, 49:1968–1971 (1971)] makes them more prone to racemization and/or $C_\alpha$-methylation, a test series was devised in which the four possible stereoisomers of GlyGlyPheLeu-$NH_2$ (SEQ ID NO:36) were synthesized and analyzed by RP-HPLC.

Each peptide was found to coelute with its enantiomer, as expected, but each enantiomeric pair was shown to have baseline separation (>2.0 minutes) from the other enantiomer pair. Therefore, an aliquot of the GGFL-$NH_2$-resin was treated with sodium hydride in dimethylsulfoxide to form the amide anions, and then quenched by washing with 1 percent water/dimethylsulfoxide. Following cleavage from the resin, the maximum percentage of the D/L, L/D enantiomeric pair, as seen by RP-HPLC, was less than 0.75 percent, establishing that the extent of racemization, and therefore potential $C_\alpha$-methylation, was less than 1 percent.

EXAMPLE 10

Enzymatic Susceptibility

The stability of N-permethylated compounds to proteolysis was examined for two permethylated sequences, AlaGlyGlyPheLeu-$NH_2$ (SEQ ID NO:37) and ArgGlyGlyPheLeu-$NH_2$ (SEQ ID NO:38) with their non-permethylated equivalents used as controls. Treatment of these found compounds by trypsin and chymotrypsin was monitored by RP-HPLC and mass spectral analysis. Rapid cleavage of AGGFL-$NH_2$ (SEQ ID NO:37) by chymotrypsin and RGGFL-$NH_2$ (SEQ ID NO:38) by trypsin was observed (<1 hour), whereas less than 1 percent cleavage of the equivalent permethylated peptides was seen following overnight enzyme exposure. These results confirmed the expectation that N-alkylated amides would be much less prone to enzymatic degradation [Simon et al., *Proc Natl. Acad. Sci. USA*, 89:9367–9371 (1992)].

The assays were performed in 1 ml 0.1M $NH_4HCO_3$, pH 7.8, at room temperature for 16 hours at a peptide concentration of 1.0 mg/ml. Enzyme to peptide concentration was 1:50.

EXAMPLE 11

Use of a Trityl Chloride N-Terminal Blocking Group

The syntheses of this and the following examples utilize a dipeptide for simplicity and ease of understanding. It should be understood, however, that the reactions disclosed are similarly useful on oligopeptide mixture sets, and particularly oligopeptide mixture sets of a length greater than two residues.

A polypropylene mash packet containing 100 mg of Phe-Leu-solid support [methylbenzhydralamine (MBHA) resin; 0.7202 mmol/g primary amino groups] was washed with DGM (1×1 minute×5 ml), 5 percent DIEA/DCM (3×2 minutes×5 ml) and DCM (2×1 minute×5 ml). Thereafter, 3.6 ml DCM and 0.364 ml DIEA (2.0886 mmol) were added to the peptide-resin, followed by addition of 100.4 mg trityl chloride (TrtCl) (0.3601 mmol). The reaction mixture was shaken for one hour. The peptide-resin was washed with DMF (2×1 minute×5 ml), 5 percent DIEA/DCM (1×2 minute×5 ml), DCM (3×1 minute×5 ml) and MeOH (1×1 minute×5 ml). A small sample of peptide-resin was assayed for remaining free amino groups using the bromophenol blue test [Krchnak et al., *Collect. Czech. Chem. Commun.*, 53:2542–2548 (1988)]. If further TrtCl coupling was necessary, a solvent mixture of DCM/DMF 9:1 or 8:2 was used. The formed Trt-Phe-Leu-MBHA resin was dried under high vacuum (lyophilizer).

All manipulations were performed under nitrogen atmosphere and anhydrous conditions. Lithium tertbutoxide in THF (5.76 m. 0.5M; 2.8808 mmol) was added to Trt-Phe- Leu-MBHA resin contained in a polypropylene mash packet (0.07202 mmol peptide, 0.14404 mmol amide groups) and shaken at room temperature for 15 minutes. The base solution was removed by syringe. 5.76 ml DMSO and the alkylation reagent, here 0.538 ml iodomethane (8.6424 mmol), were added. The reaction mixture was shaken at room temperature for 15 minutes. Using alkylation reagents such as allyl bromide or benzyl bromide, reaction time was two hours. The peptide-resin was washed with DMF (3×1 minute×5 ml), IPA (2×1 minute×5 ml), DCM (3×1 minute×5 ml) and MeOH (1×1 minute×5 ml) and dried under high vacuum (lyophilizer). The whole alkylation procedure was repeated.

The alkylated N-trityl-blocked peptide-resin was washed with DCM (1×1 minute×5 ml) and then treated with 2 percent TFA in DCM (1×2 minutes×5 ml and 1×30 minutes×5 ml), followed by the 1 minute washing steps DCM (1×5 ml), IPA (2×5 ml), DCM (2×5 ml) and MeOH (1×5 ml). The resulting, deblocked peptide was then ready for N-terminal alkylation or for use as a free amine. The resulting support-linked peptide can be referred to as Phe-(NMe)Leu-(NMe)-MBHA resin.

EXAMPLE 12

N-Terminal Reductive Alkylation

The Phe-(NMe)Leu-(NMe)-MBHA resin (0.07202 mmol primary amine) prepared in Example 11 was in a polypropylene mash packet and washed with DCM (1×1 minute×5 ml), 5 percent DIEA/DCM (3×2 minutes x 5 ml) and DCM (2×1 minute×5 ml). Thereafter, 8.6 DCM and 0.1455 ml DIEA (0.835 mmol) were added to the peptide-resin, followed by addition of 37.825 mg of 4,4'-dimethoxydiphenylmethyl chloride (DodCl) (0.14404 mmol). The mixture was shaken for 30 minutes. The peptide-resin was washed with DMF (2×1 minute×5 ml), 5 percent DIEA/DCM (1×2 minutes×5 ml) and DCM (3×1 minute×5 ml). A sample of peptide-resin was tested for remaining free amino groups using the bromophenol blue test. If necessary the reaction was repeated with prolonged coupling (1 hour). The blocked, support-linked peptide so prepared can be referred to as Dod-Phe-(NMe)Leu(NMe)-MBHA resin.

Formaldehyde (10 ml, 37 percent wt. solution in water), 90 ml DMF and 30 g of anhydrous magnesium sulfate were mixed and shaken overnight, centrifuged, and the supernatant used for the reductive methylation as follows. The thus prepared formaldehyde solution (8.5 ml) was added to Dod-Phe-(NMe)Leu-(NMe)-MBHA resin (0.07202 mmol peptide), contained in a polypropylene mesh packet, and shaken for 5 minutes. The solution was poured off. Additional 8.5 ml formaldehyde solution with 0.085 ml acetic acid were added and shaken. After 5 minutes, 85 mg of sodium cyanoborohydride were added and the mixture shaken for one hour. The peptide-resin was washed with DMF (3×1 minute×5 ml), IPA (2×1 minute×5 ml), DCM (3×1 minute×5 ml) and MeOH (1×1 minute×5 ml). The blocked, N-alkylated (N-methylated) support-linked peptide so prepared can be referred to as Me-Dod-Phe-(NMe)Leu-(NMe)-MBHA resin.

The peptide-resin was washed with DCM (1×1 minute×5 ml), then treated with 55 percent TFA in DCM (1×5 minutes×5 ml and 1×30 minutes×5 ml), followed by the 1 minute washing steps DCM (1×5 ml), IPA (2×5 ml) and DCM (2×1 ml). The peptide resin so formed can be referred to as Me-Phe-(NMe)Leu-(NMe)-MBHA resin.

It should be apparent that any of the other contemplated $C_2$–$C_7$-alkyl groups could replace methyl in the above reductive alkylation by use of the appropriate aldehyde or ketone. The N-terminal monoalkylated peptide or library of peptides that results from the above procedures can be used individually as is, used as mixtures when so prepared, or can be linked to another amino acid residue, and the chain elongated.

The foregoing is intended as illustrative of the present invention but not limiting. Numerous variations and modifications may be effected without departing from the true spirit and scope of the novel concepts of the invention.

---

We claim:

1. A process for determining the sequence of a linear peralkylated oligopeptide that preferentially binds to an acceptor that comprises the steps of:

(a) providing a library of sets of linear peralkylated oligopeptides in which each set comprises a mixture of equimolar amounts of linear $C_1$–$C_7$-alkyl peralkylated oligopeptide member chains containing the same number of two to about ten peralkylated amino acid residues in lack peralkylated oligopeptide chain, each peralkylated amino acid residue except proline having its peptidyl amido nitrogen atom alkylated with a $C_1$–$C_7$-alkyl group, the member chains of each set having one or more of at least six different predetermined peralkylated amino acid residues at the same one or more predetermined positions of the peralkylated oligopeptide chain, and each set having an equimolar amount of at least six different peralkylated amino acid residues at the same one or more other positions of the peralkylated oligopeptide chain, the amino-terminus of each peralkylated oligopeptide being selected from the group consisting of a quaternary $C_1$–$C_7$-alkylammonium group, an amino group, an N—$C_1$–$C_7$-alkylamino, an N—$C_1$–$C_7$-alkyl-N—$C_1$–$C_{18}$ hydrocarboyl and a pyroglutamoyl group, and the carboxy-terminus being selected from the group consisting of a $C_1$–$C_7$-alkyl carboxylic ester, mono- or di-N—$C_1$–$C_7$-alkylcarboxamide and a carboxyl group, the sets differing in that the one or more predetermined peralkylated amino acid residue present at the same one or more predetermined chain positions within each set are different between the sets;

(b) separately admixing each set from said library of sets with said acceptor in an aqueous medium at a set concentration of about 0.1 milligrams per liter to about 100 grams per liter, separately assaying the binding of each set to the acceptor, and determining a set exhibiting preferential, specific binding relative to the other sets, thereby identifying a peralkylated amino acid residue that provided preferential binding at said one or more predetermined positions;

(c) providing a second library of sets of linear $C_1$–$C_7$-alkyl peralkylated oligopeptides in which each set comprises a mixture of equimolar amounts of member linear peralkylated oligopeptide chains containing the same number of two to about ten peralkylated amino acid residues in each peralkylated oligopeptide chain as the chains of the first-named library of sets, each peralkylated amino acid residue except proline having its peptidyl amido nitrogen atom alkylated with a $C_1$–$C_7$-alkyl group, the member chains of each second library of sets containing the one or more peralkylated amino acid residues of the first-named set identified as exhibiting preferential, specific binding in the same one or more predetermined chain positions in said first-named sets, the member chains of said second sets having a predetermined one of said at least six different peralkylated amino acid side chains at another predetermined position of the peralkylated oligopeptide chain different from said one or more positions of the identified peralkylated amino acid residue of the first-named library of sets, each of said second library of sets having equimolar amounts of said at least six different peralkylated amino acid residues of said first-named sets at the same one or more positions of the peralkylated oligopeptide chain not occupied by said one or more identified peralkylated amino acid residue or the predetermined peralkylated amino acid residues, having one fewer peralkylated oligopeptide positions occupied by equimolar amounts of at least six different peralkylated amino acid residues, and having the same amino- and carboxy-termini as the peralkylated oligopeptides of said first-named set;

(d) separately admixing each set of said second library of sets with said acceptor in an aqueous medium at a set concentration of about 0.1 milligrams per liter to about 100 grams per liter, separately assaying the binding of each set to the acceptor, and determining a second set exhibiting preferential, specific binding, thereby identifying a peralkylated amino acid side chain that provides preferential binding at said other predetermined position in the peralkylated oligopeptide chain;

(e) repeating steps (c) and (d) using zero through seven further libraries of sets of linear peralkylated oligopeptides instead of said second plurality of sets or until preferential, specific binding does not increase when a further library is assayed, each further library of sets of linear $C_1$–$C_7$-alkyl peralkylated oligopeptides comprising a mixture of equimolar amounts of member linear peralkylated oligopeptide chains containing the same number of two to about ten peralkylated amino acid residues in each peralkylated oligopeptide chain as the chains of the first-named plurality of sets, the member chains of the sets of each further library containing the peralkylated amino acid residues in the peralkylated oligopeptide chain positions that exhibited preferential binding in a library of sets used immediately before, and a predetermined one of said at least six different peralkylated amino acid residues at another predetermined position of the peralkylated oligopeptide chain different from the positions of the identified peralkylated amino acid residues of the library of sets used immediately before, each of said further library of sets having equimolar amounts of said at least six different peralkylated amino acid residues of said first-named sets at the same one or more positions of the peralkylated oligopeptide chain not occupied by the identified peralkylated amino acid residues or the predetermined peralkylated amino acid residues, and having the same amino- and carboxy-termini as the peralkylated oligopeptides of said first-named set;

(f) where the last-assayed library of sets exhibits increased preferential, specific binding compared to the library used immediately before and one position of the peralkylated oligopeptide chain that provides preferential, specific binding is not identified, providing at least six peralkylated oligopeptide chains in which each chain contains the same number of two to about ten peralkylated amino acid residues in each peralkylated oligopeptide chain as the chains of the first-named plurality of sets, each peralkylated oligopeptide chain containing the identified peralkylated amino acid residues in the peralkylated oligopeptide chain positions that exhibited increased preferential, specific binding in the immediately preceding assay of step (e) and a predetermined one of said at least six different peralkylated amino acid residues at another predetermined position in the peralkylated oligopeptide chain different from the positions of the identified peralkylated amino acid residues used in the immediately preceding assay of step (e), and having the same amino- and carboxy-termini as the peralkylated oligopeptides of said first-named set; and (g) separately admixing each of said at least six peralkylated oligopeptides of step (f) with said acceptor in an aqueous medium at a peralkylated oligopeptide concentration of about 0.1 milligrams to about 100 grams per liter, separately assaying the binding of each peralkylated oligopeptide, and determining the peralkylated oligopeptide exhibiting preferential, specific binding, thereby determining the sequence of a linear peralkylated oligopeptide that preferentially binds to said acceptor.

2. The process according to claim 1 wherein said identified and predetermined peralkylated amino acid residues are adjacent peralkylated residues.

3. The process according to claim 2 wherein said predetermined one or more of said at least six peralkylated amino acid residues at one or more predetermined positions of (a) include a terminal position of the peralkylated oligopeptide chain.

4. The process according to claim 2 wherein said first-named peralkylated oligopeptide chains contain about five to about eight peralkylated amino acid residues.

5. The process according to claim 2 wherein at least ten different peralkylated amino acid residues are utilized instead of at least six.

6. The process according to claim 2 wherein said predetermined one or more of at least six different peralkylated amino acid residues at one or more predetermined positions of the sets of (a) are the same as said at least six different peralkylated amino acid residues present in equimolar amounts.

7. The process according to claim 1 wherein said acceptor is a cellular receptor.

8. The process according to claim 7 wherein said cellular receptor is present in a bacterium or yeast cell cultured in a growth medium.

9. The process according to claim 7 wherein each peralkylated oligopeptide set is provided coupled to a solid support.

10. A process for determining the sequence of a linear peralkylated oligopeptide that preferentially binds to an acceptor that comprises the steps of:

(a) providing separate pluralities of sets of linear peralkylated oligopeptides, each set of those pluralities comprising a mixture of equimolar amounts of linear $C_1$–$C_7$-alkyl peralkylated linear oligopeptide chains containing the same number of two to about ten peralkylated amino acid residues in each chain, each peralkylated amino acid residue except proline having its peptidyl amido nitrogen atom alkylated with a $C_1$–$C_7$-alkyl group, each set of peralkylated oligopeptide chains having a single one of at least six different predetermined peralkylated amino acid residues at a single predetermined position of the peralkylated oligopeptide chain, and each set having equimolar amounts of each of said at least six different peralkylated amino acid residues at the other positions of the peralkylated oligopeptide chain, each set differing from the other sets in the identity and chain position of said single predetermined peralkylated amino acid residue present at the predetermined repeating unit position within the set, the amino-terminus of each oligopeptide being selected from the group consisting of a quaternary $C_1$–$C_7$-alkylammonium group, an amino group, an N—$C_1$–$C_7$-alkylamino, an N—$C_1$–$C_7$-alkyl-N—$C_1$–$C_{18}$ hydrocarboyl and a pyroglutamoyl group, and the carboxy-terminus being selected from the group consisting of a $C_1$–$C_7$-alkyl carboxylic ester, mono- or di-N—$C_1$–$C_7$-alkylcarboxamide and a carboxyl group;

(b) separately admixing each set with said acceptor in an aqueous medium at a set concentration of about 0.1 milligrams per liter to about 100 grams per liter, and separately assaying the binding of each set to the acceptor;

a peralkylated amino acid residue that exhibited preferential, specific binding at each peralkylated position of the peralkylated oligopeptide chain of each set providing a sequence of a peralkylated linear oligopeptide that preferentially binds to said acceptor.

11. The process according to claim 10 wherein the single, predetermined positions of the plurality of sets, taken as a group, are adjacent to each other in the peralkylated oligopeptide chain.

12. The process according to claim 10 wherein each peralkylated oligopeptide chain contains about five to about eight peralkylated amino acid residues.

13. The process according to claim 10 wherein said single predetermined peralkylated amino acid residue of each peralkylated oligopeptide chain is one of at least ten different peralkylated amino acid residues, and the same at least ten different peralkylated amino acid residues are present in equimolar amounts at the other peralkylated oligopeptide positions of each set.

14. The process according to claim 10 wherein each of said sets is provided not coupled to a solid support used for synthesis.

* * * * *